(12) United States Patent
Howard et al.

(10) Patent No.: US 12,209,099 B2
(45) Date of Patent: Jan. 28, 2025

(54) AZETIDOBENZODIAZEPINE DIMERS AND CONJUGATES COMPRISING THEM FOR USE IN THE TREATMENT OF CANCER

(71) Applicant: MEDIMMUNE LIMITED, Cambridge (GB)

(72) Inventors: Philip Wilson Howard, Cambridge (GB); Thais Cailleau, Cambridge (GB)

(73) Assignee: MEDIMMUNE LIMITED, Cambridge (GB)

( * ) Notice: Subject to any disclaimer, the term of this patent is extended or adjusted under 35 U.S.C. 154(b) by 757 days.

(21) Appl. No.: 17/439,639

(22) PCT Filed: Mar. 13, 2020

(86) PCT No.: PCT/EP2020/056761
§ 371 (c)(1),
(2) Date: Sep. 15, 2021

(87) PCT Pub. No.: WO2020/187721
PCT Pub. Date: Sep. 24, 2020

(65) Prior Publication Data
US 2022/0160881 A1    May 26, 2022

(30) Foreign Application Priority Data

Mar. 15, 2019 (GB) .................................. 1903541
Jan. 6, 2020 (GB) .................................. 2000121

(51) Int. Cl.
| | | |
|---|---|---|
| C07D 519/00 | (2006.01) |
| A61K 31/5513 | (2006.01) |
| A61K 47/54 | (2017.01) |
| A61K 47/55 | (2017.01) |
| A61K 47/68 | (2017.01) |
| A61P 35/00 | (2006.01) |
| C07K 5/06 | (2006.01) |

(52) U.S. Cl.
CPC .......... *C07D 519/00* (2013.01); *A61K 47/542* (2017.08); *A61K 47/55* (2017.08); *A61K 47/6803* (2017.08); *A61P 35/00* (2018.01)

(58) Field of Classification Search
CPC ......... C07D 519/00; C07K 5/06; A61P 35/00; A61K 31/5513; A61K 47/68
See application file for complete search history.

(56) References Cited

U.S. PATENT DOCUMENTS

| | | |
|---|---|---|
| 3,361,742 A | 1/1968 | Julius et al. |
| 3,523,941 A | 8/1970 | Leimgruber et al. |
| 3,524,849 A | 8/1970 | Batcho et al. |
| 3,794,644 A | 2/1974 | Karlyone et al. |
| 4,185,016 A | 1/1980 | Takanabe et al. |
| 4,239,683 A | 12/1980 | Takanabe et al. |
| 4,309,437 A | 1/1982 | Ueda et al. |
| 4,353,827 A | 10/1982 | Hunkeler et al. |
| 4,382,032 A | 5/1983 | Hunkeler et al. |
| 4,386,028 A | 5/1983 | Hunkeler et al. |
| 4,405,516 A | 9/1983 | Hunkeler et al. |
| 4,405,517 A | 9/1983 | Hunkeler et al. |
| 4,407,752 A | 10/1983 | Hunkeler et al. |
| 4,427,587 A | 1/1984 | Kaneko et al. |
| 4,427,588 A | 1/1984 | Kaneko et al. |
| 4,701,325 A | 10/1987 | Ueda et al. |
| 4,816,567 A | 3/1989 | Cabilly et al. |
| 4,923,984 A | 5/1990 | Matsumura et al. |
| 5,362,852 A | 11/1994 | Geoghegan |
| 5,418,241 A | 5/1995 | Jegham et al. |
| 5,440,021 A | 8/1995 | Chuntharapai et al. |
| 5,561,119 A | 10/1996 | Jacquesy et al. |
| 5,583,024 A | 12/1996 | McElroy et al. |
| 5,621,002 A | 4/1997 | Bosslet et al. |
| 5,644,033 A | 7/1997 | Seon |
| 5,674,713 A | 10/1997 | McElroy et al. |
| 5,700,670 A | 12/1997 | Yamagishi et al. |
| 5,773,223 A | 6/1998 | Shyamala et al. |
| 5,792,616 A | 8/1998 | Persico et al. |
| 5,854,399 A | 12/1998 | Salomon et al. |
| 5,869,445 A | 2/1999 | Cheever et al. |

(Continued)

FOREIGN PATENT DOCUMENTS

| | | |
|---|---|---|
| CN | 101171257 | 4/2008 |
| EP | 0522868 | 1/1993 |

(Continued)

OTHER PUBLICATIONS

Adair et al., "Antibody-drug conjugates—a perfect synergy," Exp. Opin. Biol. Ther. (2012), pp. 1-16.
Adams et al., "Molecular modelling of a sequence-specific DNA-binding agent based on the pyrrolo[2,1-c][1,4]benzodiazepines," Pharm. Pharmacol. Commun. (1999) 5:555-560.
Aird et al., "ABCB1 genetic polymorphism influences the pharmacology of the new pyrrolobenzodiazepine derivative SJG-136," Pharmacogenomics Journal (2008) 8(4):289-296.
Alley et al., "SJG-136 (NSC 694501), a novel rationally designed DNA minor groove interstrand cross-linking agent with potent and broad spectrum antitumor activity. Part 2: Efficacy evaluations," Cancer Res. (2004) 64:6700-6706.

(Continued)

*Primary Examiner* — Bruck Kifle
(74) *Attorney, Agent, or Firm* — Lisa Mueller; Casimir Jones SC

(57) ABSTRACT

A compound of formula IV: as well as drug-linkers and conjugates comprising this compound, and the use of the conjugates in treating cancer.

IV

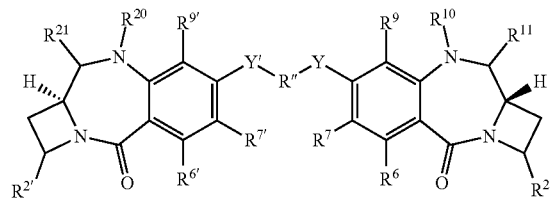

19 Claims, 1 Drawing Sheet

(56) References Cited

U.S. PATENT DOCUMENTS

| | | |
|---|---|---|
| 5,976,551 A | 11/1999 | Mottez et al. |
| 6,011,146 A | 1/2000 | Mottez et al. |
| 6,153,408 A | 11/2000 | Abastado et al. |
| 6,214,345 B1 | 4/2001 | Firestone et al. |
| 6,218,519 B1 | 4/2001 | Kenten et al. |
| 6,268,488 B1 | 7/2001 | Barbas, III et al. |
| 6,362,331 B1 | 3/2002 | Kamal et al. |
| 6,518,404 B1 | 2/2003 | Li et al. |
| 6,534,482 B1 | 3/2003 | Fikes et al. |
| 6,555,339 B1 | 4/2003 | Liaw et al. |
| 6,562,806 B1 | 5/2003 | Thurston et al. |
| 6,602,677 B1 | 8/2003 | Wood et al. |
| 6,608,192 B1 | 8/2003 | Thurston et al. |
| 6,660,742 B2 | 12/2003 | Lee |
| 6,660,856 B2 | 12/2003 | Wang |
| 6,677,435 B2 | 1/2004 | Barbas, III et al. |
| 6,747,144 B1 | 6/2004 | Thurston et al. |
| 6,759,509 B1 | 7/2004 | King et al. |
| 6,835,807 B1 | 12/2004 | Sasaki et al. |
| 6,884,799 B2 | 4/2005 | Kamal et al. |
| 6,909,006 B1 | 6/2005 | Thurston et al. |
| 7,049,311 B1 | 5/2006 | Thurston et al. |
| 7,067,511 B2 | 6/2006 | Thurston et al. |
| 7,223,837 B2 | 5/2007 | De Groot et al. |
| 7,244,724 B2 | 7/2007 | Liu et al. |
| 7,265,105 B2 | 9/2007 | Thurston et al. |
| 7,375,078 B2 | 5/2008 | Feng |
| 7,407,951 B2 | 8/2008 | Thurston et al. |
| 7,429,658 B2 | 9/2008 | Howard et al. |
| 7,498,298 B2 | 3/2009 | Doronina et al. |
| 7,511,032 B2 | 3/2009 | Liu et al. |
| 7,521,541 B2 | 4/2009 | Eigenbrot et al. |
| 7,528,126 B2 | 5/2009 | Howard et al. |
| 7,557,099 B2 | 7/2009 | Howard et al. |
| 7,612,062 B2 | 11/2009 | Gregson et al. |
| 7,704,924 B2 | 4/2010 | Thurston et al. |
| 7,723,485 B2 | 5/2010 | Junutula et al. |
| 7,741,319 B2 | 6/2010 | Howard et al. |
| 8,034,808 B2 | 11/2011 | Delavault et al. |
| 8,163,736 B2 | 4/2012 | Gauzy et al. |
| 8,321,774 B2 | 11/2012 | Barthal et al. |
| 8,487,092 B2 | 7/2013 | Howard et al. |
| 8,501,934 B2 | 8/2013 | Howard et al. |
| 8,592,576 B2 | 11/2013 | Howard et al. |
| 8,633,185 B2 | 1/2014 | Howard et al. |
| 8,637,664 B2 | 1/2014 | Howard et al. |
| 8,697,688 B2 | 4/2014 | Howard et al. |
| 8,829,184 B2 | 9/2014 | Howard et al. |
| 8,940,733 B2 | 1/2015 | Howard et al. |
| 9,102,704 B2 | 8/2015 | Howard |
| 9,242,013 B2 | 1/2016 | Howard et al. |
| 9,321,774 B2 | 4/2016 | Howard et al. |
| 9,376,440 B2 | 6/2016 | Howard et al. |
| 9,387,259 B2 | 7/2016 | Jeffrey et al. |
| 9,388,187 B2 | 7/2016 | Howard et al. |
| 9,399,073 B2 | 7/2016 | Howard et al. |
| 9,399,641 B2 | 7/2016 | Howard et al. |
| 9,415,117 B2 | 8/2016 | Howard |
| 9,464,141 B2 | 10/2016 | Asundi et al. |
| 9,526,798 B2 | 12/2016 | Jeffrey et al. |
| 9,562,049 B2 | 2/2017 | Howard |
| 9,592,240 B2 | 3/2017 | Howard et al. |
| 9,624,227 B2 | 4/2017 | Howard et al. |
| 9,649,390 B2 | 5/2017 | Howard et al. |
| 9,707,301 B2 | 7/2017 | Jeffrey et al. |
| 9,713,647 B2 | 7/2017 | Jeffrey et al. |
| 9,732,084 B2 | 8/2017 | Howard et al. |
| 9,745,303 B2 | 8/2017 | Howard et al. |
| 9,889,207 B2 | 2/2018 | Howard |
| 9,956,298 B2 | 5/2018 | Howard et al. |
| 2001/0055751 A1 | 12/2001 | Reiter et al. |
| 2002/0034749 A1 | 3/2002 | Billing-Medel et al. |
| 2002/0042366 A1 | 4/2002 | Thompson et al. |
| 2002/0150573 A1 | 10/2002 | Nussenzweig |
| 2002/0193567 A1 | 12/2002 | Jacobs et al. |
| 2003/0060612 A1 | 3/2003 | Goddard et al. |
| 2003/0062401 A1 | 4/2003 | Hasz et al. |
| 2003/0064397 A1 | 4/2003 | Spancake et al. |
| 2003/0065143 A1 | 4/2003 | Eaton et al. |
| 2003/0091580 A1 | 5/2003 | Mitcham et al. |
| 2003/0096743 A1 | 5/2003 | Senter et al. |
| 2003/0096961 A1 | 5/2003 | Baker et al. |
| 2003/0105292 A1 | 6/2003 | Liaw et al. |
| 2003/0109676 A1 | 6/2003 | Li et al. |
| 2003/0118592 A1 | 6/2003 | Ledbetter et al. |
| 2003/0119121 A1 | 6/2003 | Baker et al. |
| 2003/0119122 A1 | 6/2003 | Baker et al. |
| 2003/0119125 A1 | 6/2003 | Baker et al. |
| 2003/0119126 A1 | 6/2003 | Baker et al. |
| 2003/0119128 A1 | 6/2003 | Baker et al. |
| 2003/0119129 A1 | 6/2003 | Baker et al. |
| 2003/0119130 A1 | 6/2003 | Baker et al. |
| 2003/0119131 A1 | 6/2003 | Baker et al. |
| 2003/0124140 A1 | 7/2003 | Bangur et al. |
| 2003/0124579 A1 | 7/2003 | Mack et al. |
| 2003/0129192 A1 | 7/2003 | Chenault et al. |
| 2003/0130189 A1 | 7/2003 | Senter et al. |
| 2003/0134790 A1 | 7/2003 | Langenfeld |
| 2003/0143557 A1 | 7/2003 | Penner |
| 2003/0157089 A1 | 8/2003 | Xu et al. |
| 2003/0165504 A1 | 9/2003 | Retter et al. |
| 2003/0175775 A1 | 9/2003 | Lepoul et al. |
| 2003/0185830 A1 | 10/2003 | Xu et al. |
| 2003/0186372 A1 | 10/2003 | Baker et al. |
| 2003/0186373 A1 | 10/2003 | Baker et al. |
| 2003/0194704 A1 | 10/2003 | Penn et al. |
| 2003/0195196 A1 | 10/2003 | Thurston et al. |
| 2003/0206918 A1 | 11/2003 | Fanger et al. |
| 2003/0219806 A1 | 11/2003 | Glucksmann et al. |
| 2003/0224411 A1 | 12/2003 | Stanton et al. |
| 2003/0224454 A1 | 12/2003 | Ryseck et al. |
| 2003/0228319 A1 | 12/2003 | Frantz et al. |
| 2003/0232056 A1 | 12/2003 | Fanger et al. |
| 2003/0232350 A1 | 12/2003 | Afar et al. |
| 2004/0001827 A1 | 1/2004 | Dennis |
| 2004/0005320 A1 | 1/2004 | Thompson et al. |
| 2004/0005538 A1 | 1/2004 | Chen et al. |
| 2004/0005563 A1 | 1/2004 | Mack et al. |
| 2004/0005598 A1 | 1/2004 | Devaux et al. |
| 2004/0018194 A1 | 1/2004 | Francisco et al. |
| 2004/0018553 A1 | 1/2004 | Billing-Medel et al. |
| 2004/0022727 A1 | 2/2004 | Stanton et al. |
| 2004/0044179 A1 | 3/2004 | Baker et al. |
| 2004/0044180 A1 | 3/2004 | Baker et al. |
| 2004/0052793 A1 | 3/2004 | Carter et al. |
| 2004/0101874 A1 | 5/2004 | Ghosh et al. |
| 2004/0101899 A1 | 5/2004 | Dillon et al. |
| 2004/0121940 A1 | 6/2004 | De Groot et al. |
| 2004/0138269 A1 | 7/2004 | Sun et al. |
| 2004/0197325 A1 | 10/2004 | Law et al. |
| 2004/0198722 A1 | 10/2004 | Thurston et al. |
| 2004/0249130 A1 | 12/2004 | Stanton et al. |
| 2005/0271615 A1 | 12/2005 | Shabat et al. |
| 2006/0116422 A1 | 6/2006 | De Groot et al. |
| 2007/0072846 A1 | 3/2007 | Vishnuvajjala et al. |
| 2007/0092940 A1 | 4/2007 | Eigenbrot et al. |
| 2007/0154906 A1 | 7/2007 | Martin et al. |
| 2007/0185336 A1 | 8/2007 | Rossen et al. |
| 2007/0191349 A1 | 8/2007 | Howard et al. |
| 2007/0232592 A1 | 10/2007 | Delavault et al. |
| 2007/0249591 A1 | 10/2007 | Howard et al. |
| 2008/0090812 A1 | 4/2008 | Pepper et al. |
| 2008/0092940 A1 | 4/2008 | Nakajima |
| 2008/0112961 A1 | 5/2008 | Stavenhagen et al. |
| 2008/0206239 A1 | 8/2008 | Jones et al. |
| 2008/0213289 A1 | 9/2008 | Francisco et al. |
| 2008/0214525 A1 | 9/2008 | Howard et al. |
| 2009/0036431 A1 | 2/2009 | Gauzy et al. |
| 2009/0148942 A1 | 6/2009 | McDonagh et al. |
| 2009/0149449 A1 | 6/2009 | Liu et al. |
| 2009/0274713 A1 | 11/2009 | Chari et al. |
| 2009/0304710 A1 | 12/2009 | Park et al. |
| 2010/0028346 A1 | 2/2010 | Lutz et al. |
| 2010/0047257 A1 | 2/2010 | Blanc et al. |

(56) References Cited

U.S. PATENT DOCUMENTS

| | | |
|---|---|---|
| 2010/0113425 A1 | 5/2010 | Howard et al. |
| 2010/0203007 A1 | 8/2010 | Li et al. |
| 2010/0316656 A1 | 12/2010 | Bouchard et al. |
| 2011/0039969 A1 | 2/2011 | Muratoglu et al. |
| 2011/0070227 A1 | 3/2011 | Novotney-Barry et al. |
| 2011/0091372 A1 | 4/2011 | Ghayur et al. |
| 2011/0160192 A1 | 6/2011 | Howard et al. |
| 2011/0195021 A1 | 8/2011 | Deckert et al. |
| 2011/0195022 A1 | 8/2011 | Deckert et al. |
| 2011/0196148 A1 | 8/2011 | Howard et al. |
| 2011/0201803 A1 | 8/2011 | Howard et al. |
| 2011/0256157 A1 | 10/2011 | Howard et al. |
| 2012/0233172 A1 | 9/2012 | Skillcorn et al. |
| 2012/0238731 A1 | 9/2012 | Fishkin et al. |
| 2013/0028917 A1 | 1/2013 | Howard et al. |
| 2013/0028919 A1 | 1/2013 | Howard et al. |
| 2013/0137659 A1 | 5/2013 | Commercon et al. |
| 2013/0244171 A1 | 9/2013 | Yamasaki et al. |
| 2013/0266595 A1 | 10/2013 | Flygare et al. |
| 2013/0266596 A1 | 10/2013 | Li et al. |
| 2013/0302359 A1 | 11/2013 | Li et al. |
| 2013/0304357 A1 | 11/2013 | Koci et al. |
| 2014/0030279 A1 | 1/2014 | Polakis et al. |
| 2014/0030280 A1 | 1/2014 | Polakis |
| 2014/0066435 A1 | 3/2014 | Howard et al. |
| 2014/0088089 A1 | 3/2014 | Chari |
| 2014/0120118 A1 | 5/2014 | Howard |
| 2014/0121126 A1 | 5/2014 | Bivona et al. |
| 2014/0127239 A1 | 5/2014 | Howard |
| 2014/0155590 A1 | 6/2014 | Commercon et al. |
| 2014/0234346 A1 | 8/2014 | Howard |
| 2014/0274907 A1 | 9/2014 | Howard et al. |
| 2014/0275522 A1 | 9/2014 | Howard et al. |
| 2014/0286970 A1 | 9/2014 | Jeffrey et al. |
| 2014/0294868 A1 | 10/2014 | Howard et al. |
| 2014/0302066 A1 | 10/2014 | Jeffrey et al. |
| 2015/0111880 A1 | 4/2015 | Howard et al. |
| 2015/0126495 A1 | 5/2015 | Howard et al. |
| 2015/0133435 A1 | 5/2015 | Howard et al. |
| 2015/0158869 A1 | 6/2015 | Howard |
| 2015/0183883 A1 | 7/2015 | Asundi |
| 2015/0265722 A1 | 9/2015 | Van Berkel |
| 2015/0273077 A1 | 10/2015 | Van Berkel |
| 2015/0273078 A1 | 10/2015 | Van Berkel |
| 2015/0274737 A1 | 10/2015 | Howard et al. |
| 2015/0283258 A1 | 10/2015 | Van Berkel |
| 2015/0283262 A1 | 10/2015 | Van Berkel |
| 2015/0283263 A1 | 10/2015 | Van Berkel |
| 2015/0297746 A1 | 10/2015 | Van Berkel |
| 2015/0315196 A1 | 11/2015 | Howard et al. |
| 2015/0344482 A1 | 12/2015 | Howard et al. |
| 2016/0015828 A1 | 1/2016 | Torgor |
| 2016/0031887 A1 | 2/2016 | Howard et al. |
| 2016/0075787 A1 | 3/2016 | Zheng et al. |
| 2016/0144052 A1 | 5/2016 | Howard et al. |
| 2016/0074527 A1 | 7/2016 | Flygare et al. |
| 2016/0250344 A1 | 9/2016 | Howard et al. |
| 2016/0250345 A1 | 9/2016 | Howard et al. |
| 2016/0250346 A1 | 9/2016 | Howard et al. |
| 2016/0256561 A1 | 9/2016 | Howard et al. |
| 2016/0263242 A1 | 9/2016 | Howard et al. |
| 2016/0310611 A1 | 10/2016 | Flygare et al. |
| 2017/0239365 A1 | 8/2017 | Howard et al. |
| 2017/0290924 A1 | 10/2017 | Jeffrey et al. |
| 2017/0298137 A1 | 10/2017 | Jeffrey et al. |
| 2017/0340752 A1 | 11/2017 | Howard |
| 2018/0125997 A1 | 5/2018 | Howard et al. |
| 2018/0134717 A1 | 5/2018 | Howard et al. |

FOREIGN PATENT DOCUMENTS

| | | |
|---|---|---|
| EP | 0875569 | 11/1998 |
| EP | 1295944 | 3/2003 |
| EP | 1347046 | 9/2003 |
| EP | 1394274 | 3/2004 |
| EP | 1439393 | 7/2004 |
| EP | 1813614 | 8/2007 |
| EP | 2019104 | 1/2009 |
| EP | 2298817 | 3/2011 |
| EP | 2528625 | 7/2013 |
| EP | 3690038 A1 | 8/2020 |
| FR | 2027356 | 12/1969 |
| FR | 2586683 | 3/1987 |
| GB | 1299198 | 12/1972 |
| GB | 2053894 | 2/1981 |
| JP | 5382792 | 7/1978 |
| JP | 57131791 | 8/1982 |
| JP | 58180487 | 10/1983 |
| JP | 05003790 | 1/1993 |
| JP | 2004113151 | 4/2004 |
| WO | WO 199102536 | 3/1991 |
| WO | WO 199207574 | 5/1992 |
| WO | WO 199217497 | 10/1992 |
| WO | WO 199219620 | 11/1992 |
| WO | WO 199318045 | 9/1993 |
| WO | WO 199410312 | 5/1994 |
| WO | WO 199428931 | 12/1994 |
| WO | WO 199504718 | 2/1995 |
| WO | WO 199630514 | 10/1996 |
| WO | WO 199707198 | 2/1997 |
| WO | WO 199744452 | 11/1997 |
| WO | WO 199813059 | 4/1998 |
| WO | WO 199837193 | 8/1998 |
| WO | WO 199840403 | 9/1998 |
| WO | WO 199851805 | 11/1998 |
| WO | WO 199851824 | 11/1998 |
| WO | WO 199928468 | 6/1999 |
| WO | WO 199946284 | 9/1999 |
| WO | WO 199958658 | 11/1999 |
| WO | WO 200003291 | 1/2000 |
| WO | WO 200012506 | 3/2000 |
| WO | WO 200012507 | 3/2000 |
| WO | WO 200012508 | 3/2000 |
| WO | WO 200012509 | 3/2000 |
| WO | WO 200014228 | 3/2000 |
| WO | WO 200020579 | 4/2000 |
| WO | WO 200022129 | 4/2000 |
| WO | WO 200032752 | 6/2000 |
| WO | WO 200036107 | 6/2000 |
| WO | WO 200040614 | 7/2000 |
| WO | WO 200044899 | 8/2000 |
| WO | WO 200012130 | 9/2000 |
| WO | WO 200053216 | 9/2000 |
| WO | WO 200055351 | 9/2000 |
| WO | WO 200075655 | 12/2000 |
| WO | WO 200100244 | 1/2001 |
| WO | WO 200116104 | 3/2001 |
| WO | WO 200116318 | 3/2001 |
| WO | WO 200138490 | 5/2001 |
| WO | WO 200140269 | 6/2001 |
| WO | WO 200140309 | 6/2001 |
| WO | WO 200141787 | 6/2001 |
| WO | WO 200145746 | 6/2001 |
| WO | WO 200146232 | 6/2001 |
| WO | WO 200146261 | 6/2001 |
| WO | WO 200148204 | 7/2001 |
| WO | WO 200153463 | 7/2001 |
| WO | WO 200157188 | 8/2001 |
| WO | WO 200162794 | 8/2001 |
| WO | WO 200166689 | 9/2001 |
| WO | WO 200172830 | 10/2001 |
| WO | WO 200172962 | 10/2001 |
| WO | WO 200175177 | 10/2001 |
| WO | WO 200177172 | 10/2001 |
| WO | WO 200188133 | 11/2001 |
| WO | WO 200190304 | 11/2001 |
| WO | WO 200194641 | 12/2001 |
| WO | WO 200198351 | 12/2001 |
| WO | WO 200202587 | 1/2002 |
| WO | WO 200202624 | 1/2002 |
| WO | WO 200202634 | 1/2002 |
| WO | WO 200206317 | 1/2002 |
| WO | WO 200206339 | 1/2002 |
| WO | WO 200210187 | 2/2002 |

(56) References Cited

FOREIGN PATENT DOCUMENTS

| | | |
|---|---|---|
| WO | WO 200210382 | 2/2002 |
| WO | WO 200212341 | 2/2002 |
| WO | WO 200213847 | 2/2002 |
| WO | WO 200214503 | 2/2002 |
| WO | WO 200216413 | 2/2002 |
| WO | WO 200222153 | 3/2002 |
| WO | WO 200222636 | 3/2002 |
| WO | WO 200222660 | 3/2002 |
| WO | WO 200222808 | 3/2002 |
| WO | WO 200224909 | 3/2002 |
| WO | WO 200226822 | 4/2002 |
| WO | WO 200230268 | 4/2002 |
| WO | WO 200238766 | 5/2002 |
| WO | WO 200254940 | 7/2002 |
| WO | WO 200259377 | 8/2002 |
| WO | WO 200260317 | 8/2002 |
| WO | WO 200261087 | 8/2002 |
| WO | WO 200264798 | 8/2002 |
| WO | WO 200271928 | 9/2002 |
| WO | WO 200272596 | 9/2002 |
| WO | WO 200278524 | 10/2002 |
| WO | WO 200281646 | 10/2002 |
| WO | WO 200283866 | 10/2002 |
| WO | WO 200286443 | 10/2002 |
| WO | WO 200288170 | 11/2002 |
| WO | WO 200288172 | 11/2002 |
| WO | WO 200289747 | 11/2002 |
| WO | WO 200292836 | 11/2002 |
| WO | WO 200294852 | 11/2002 |
| WO | WO 200298358 | 12/2002 |
| WO | WO 200299074 | 12/2002 |
| WO | WO 200299122 | 12/2002 |
| WO | WO 2002101075 | 12/2002 |
| WO | WO 2002102235 | 12/2002 |
| WO | WO 200216429 | 1/2003 |
| WO | WO 2003000842 | 1/2003 |
| WO | WO 2003002717 | 1/2003 |
| WO | WO 2003003906 | 1/2003 |
| WO | WO 2003003984 | 1/2003 |
| WO | WO 2003004529 | 1/2003 |
| WO | WO 2003004989 | 1/2003 |
| WO | WO 2003008537 | 1/2003 |
| WO | WO 2003009814 | 2/2003 |
| WO | WO 2003014294 | 2/2003 |
| WO | WO 2003016475 | 2/2003 |
| WO | WO 2003016494 | 2/2003 |
| WO | WO 2003018621 | 3/2003 |
| WO | WO 2003022995 | 3/2003 |
| WO | WO 2003023013 | 3/2003 |
| WO | WO 2003024392 | 3/2003 |
| WO | WO 2003025138 | 3/2003 |
| WO | WO 2003025148 | 3/2003 |
| WO | WO 2003025228 | 3/2003 |
| WO | WO 2003026493 | 4/2003 |
| WO | WO 2003026577 | 4/2003 |
| WO | WO 2003029262 | 4/2003 |
| WO | WO 2003029277 | 4/2003 |
| WO | WO 2003029421 | 4/2003 |
| WO | WO 2003034984 | 5/2003 |
| WO | WO 2003035846 | 5/2003 |
| WO | WO 2003042661 | 5/2003 |
| WO | WO 2003043583 | 5/2003 |
| WO | WO 2003045422 | 6/2003 |
| WO | WO 2003048202 | 6/2003 |
| WO | WO 2003054152 | 7/2003 |
| WO | WO 2003055439 | 7/2003 |
| WO | WO 2003055443 | 7/2003 |
| WO | WO 2003060612 | 7/2003 |
| WO | WO 2003062401 | 7/2003 |
| WO | WO 2003072035 | 9/2003 |
| WO | WO 2003072036 | 9/2003 |
| WO | WO 2003077836 | 9/2003 |
| WO | WO 2003081210 | 10/2003 |
| WO | WO 2003083041 | 10/2003 |
| WO | WO 2003083047 | 10/2003 |
| WO | WO 2003083074 | 10/2003 |
| WO | WO 2003087306 | 10/2003 |
| WO | WO 2003087768 | 10/2003 |
| WO | WO 2003088808 | 10/2003 |
| WO | WO 2003089624 | 10/2003 |
| WO | WO 2003089904 | 10/2003 |
| WO | WO 2003093444 | 11/2003 |
| WO | WO 2003097803 | 11/2003 |
| WO | WO 2003101283 | 12/2003 |
| WO | WO 2003101400 | 12/2003 |
| WO | WO 2003104270 | 12/2003 |
| WO | WO 2003104275 | 12/2003 |
| WO | WO 2003104399 | 12/2003 |
| WO | WO 2003105758 | 12/2003 |
| WO | WO 2004000221 | 12/2003 |
| WO | WO 2004000997 | 12/2003 |
| WO | WO 2004001004 | 12/2003 |
| WO | WO 2004005598 | 1/2004 |
| WO | WO 2004009622 | 1/2004 |
| WO | WO 2004011611 | 2/2004 |
| WO | WO 2004015426 | 2/2004 |
| WO | WO 2004016225 | 2/2004 |
| WO | WO 2004020583 | 3/2004 |
| WO | WO 2004020595 | 3/2004 |
| WO | WO 2004022709 | 3/2004 |
| WO | WO 2004022778 | 3/2004 |
| WO | WO 2004027049 | 4/2004 |
| WO | WO 2004031238 | 4/2004 |
| WO | WO 2004032828 | 4/2004 |
| WO | WO 2004032842 | 4/2004 |
| WO | WO 2004040000 | 5/2004 |
| WO | WO 2004042346 | 5/2004 |
| WO | WO 2004043361 | 5/2004 |
| WO | WO 2004043963 | 5/2004 |
| WO | WO 2004044178 | 5/2004 |
| WO | WO 2004045516 | 6/2004 |
| WO | WO 2004045520 | 6/2004 |
| WO | WO 2004045553 | 6/2004 |
| WO | WO 2004046342 | 6/2004 |
| WO | WO 2004047749 | 6/2004 |
| WO | WO 2004048938 | 6/2004 |
| WO | WO 2004053079 | 6/2004 |
| WO | WO 2004058309 | 7/2004 |
| WO | WO 2004063355 | 7/2004 |
| WO | WO 2004063362 | 7/2004 |
| WO | WO 2004063709 | 7/2004 |
| WO | WO 2004065576 | 8/2004 |
| WO | WO 2004065577 | 8/2004 |
| WO | WO 2004074320 | 9/2004 |
| WO | WO 2005023814 | 3/2005 |
| WO | WO 2005040170 | 5/2005 |
| WO | WO 2005042535 | 5/2005 |
| WO | WO 2005079479 | 9/2005 |
| WO | WO 2005082023 | 9/2005 |
| WO | WO 2005085177 | 9/2005 |
| WO | WO 2005085250 | 9/2005 |
| WO | WO 2005085251 | 9/2005 |
| WO | WO 2005085259 | 9/2005 |
| WO | WO 2005085260 | 9/2005 |
| WO | WO 2005105113 | 11/2005 |
| WO | WO 2005110423 | 11/2005 |
| WO | WO 2006065533 A2 | 6/2006 |
| WO | WO 2006111759 | 10/2006 |
| WO | WO 2007039752 | 4/2007 |
| WO | WO 2007044515 | 4/2007 |
| WO | WO 2007085930 | 8/2007 |
| WO | WO 2008010101 | 1/2008 |
| WO | WO 2008022152 | 2/2008 |
| WO | WO 2008047242 | 4/2008 |
| WO | WO 2008050140 | 5/2008 |
| WO | WO 2008070593 | 6/2008 |
| WO | WO 2009016516 | 2/2009 |
| WO | WO 2009052249 | 4/2009 |
| WO | WO 2009060208 | 5/2009 |
| WO | WO 2009060215 | 5/2009 |
| WO | WO 2009117531 | 9/2009 |
| WO | WO 2010010347 | 1/2010 |
| WO | WO 2010043877 | 4/2010 |
| WO | WO 2010043880 | 4/2010 |

(56) References Cited

FOREIGN PATENT DOCUMENTS

| | | |
|---|---|---|
| WO | WO 2010091150 | 8/2010 |
| WO | WO 2010095031 | 8/2010 |
| WO | WO 2011023883 | 3/2011 |
| WO | WO 2011038159 | 3/2011 |
| WO | WO 2011059850 | 5/2011 |
| WO | WO 2011100227 | 8/2011 |
| WO | WO 2011128650 | 10/2011 |
| WO | WO 2011130598 | 10/2011 |
| WO | WO 2011130613 | 10/2011 |
| WO | WO 2011130615 | 10/2011 |
| WO | WO 2011130616 | 10/2011 |
| WO | WO 2011133039 | 10/2011 |
| WO | WO 2012014147 | 2/2012 |
| WO | WO 2012018325 | 2/2012 |
| WO | WO 2012039717 | 3/2012 |
| WO | WO 2012064733 | 5/2012 |
| WO | WO 2012112687 | 8/2012 |
| WO | WO 2012112708 | 8/2012 |
| WO | WO 2012128868 | 9/2012 |
| WO | WO 2013041606 | 3/2013 |
| WO | WO 2013053871 | 4/2013 |
| WO | WO 2013053872 | 4/2013 |
| WO | WO 2013053873 | 4/2013 |
| WO | WO 2013055987 | 4/2013 |
| WO | WO 2013055990 | 4/2013 |
| WO | WO 2013055993 | 4/2013 |
| WO | WO 2013164592 | 11/2013 |
| WO | WO 2013164593 | 11/2013 |
| WO | WO 2013177481 | 11/2013 |
| WO | WO 2014011518 | 1/2014 |
| WO | WO 2014011519 | 1/2014 |
| WO | WO 2014022679 | 2/2014 |
| WO | WO 2014031566 | 2/2014 |
| WO | WO 2014057072 | 4/2014 |
| WO | WO 2014057073 | 4/2014 |
| WO | WO 2014057074 | 4/2014 |
| WO | WO 2014057113 | 4/2014 |
| WO | WO 2014057114 | 4/2014 |
| WO | WO 2014057115 | 4/2014 |
| WO | WO 2014057117 | 4/2014 |
| WO | WO 2014057118 | 4/2014 |
| WO | WO 2014057119 | 4/2014 |
| WO | WO 2014057120 | 4/2014 |
| WO | WO 2014057122 | 4/2014 |
| WO | WO 2014080251 | 5/2014 |
| WO | WO 2014096365 | 6/2014 |
| WO | WO 2014096368 | 6/2014 |
| WO | WO 2014130879 | 8/2014 |
| WO | WO 2014140174 | 9/2014 |
| WO | WO 2014140862 | 9/2014 |
| WO | WO 2014159981 | 10/2014 |
| WO | WO 2014174111 | 10/2014 |
| WO | WO 2015028850 | 3/2015 |
| WO | WO 2015031693 | 3/2015 |
| WO | WO 2015052321 | 4/2015 |
| WO | WO 2015052322 | 4/2015 |
| WO | WO 2015052332 | 4/2015 |
| WO | WO 2015052333 | 4/2015 |
| WO | WO 2015052334 | 4/2015 |
| WO | WO 2015052335 | 4/2015 |
| WO | WO 2015052532 | 4/2015 |
| WO | WO 2015052533 | 4/2015 |
| WO | WO 2015052534 | 4/2015 |
| WO | WO 2015052535 | 4/2015 |
| WO | WO 2015095124 | 6/2015 |
| WO | WO 2015112822 | 7/2015 |
| WO | WO 2015157595 | 10/2015 |
| WO | WO 2015159076 | 10/2015 |
| WO | WO 2016201065 | 12/2015 |
| WO | WO 2016037644 | 3/2016 |
| WO | WO 2016038383 | 3/2016 |
| WO | WO 2016040868 | 3/2016 |
| WO | WO 2016044396 | 3/2016 |
| WO | WO 2016044560 | 3/2016 |
| WO | WO 2016053107 | 4/2016 |
| WO | WO 2016166297 | 10/2016 |
| WO | WO 2016166298 | 10/2016 |
| WO | WO 2016166299 | 10/2016 |
| WO | WO 2016166300 | 10/2016 |
| WO | WO 2016166302 | 10/2016 |
| WO | WO 2016166305 | 10/2016 |
| WO | WO 2016166307 | 10/2016 |
| WO | WO 2016209951 | 12/2016 |
| WO | WO 2017035353 | 3/2017 |
| WO | WO 2017059289 | 4/2017 |
| WO | WO 2017137553 | 8/2017 |
| WO | WO 2017186894 | 11/2017 |
| WO | WO 2017201132 | 11/2017 |
| WO | WO 2018031662 | 2/2018 |
| WO | WO 2018069490 | 4/2018 |
| WO | WO 2018089393 | 5/2018 |
| WO | WO 2018146188 | 8/2018 |
| WO | WO 2018182341 | 10/2018 |
| WO | WO 2018192944 | 10/2018 |
| WO | WO 2018218093 | 11/2018 |
| WO | WO 2020006722 | 1/2020 |

OTHER PUBLICATIONS

Alley, M.C., "Efficacy evaluations of SJG-136 (NSC 694501), a novel pyrrolobenzodiazepine dimer with broad spectrum antitumor activity," Proceedings of the American Association for Cancer Research Annual Meeting (Mar. 2002) 43:63.

Alley, S. C., "Contribution of Linker Stability to the Activities of Anticancer Immunoconjugates" Bioconjugate Chem 2008, 19, 759-765.

Althius, T. H. and Hess, H. J., "Synthesis and Identification of the Major Metabolites of Prazosin Formed in Dog and Rat," J. Medicinal Chem. (1977) 20(1):146-148.

Altuvia et al., "Ranking potential binding peptides to MHC molecules by a computational threading approach." J. Mol. Biol., 249, 244-250 (1995).

Amiel J., et al., "Heterozygous endothelin receptor B {EDNRB) mutations in isolated Hirschsprung disease," Hum. Mol. Genet. 5, 355-357, 1996.

Amir et al., "Self-Immolative Dendrimers," (2003) Angew. Chem. Int. Ed. 42:4494-4499.

Amsberry, et al., "The Lactonization of 2'-Hydroxyhydrocinnamic Acid Amides: A Potential Prodrug for Amines," (1990) J. Org. Chem. 55:5867-5877.

Antonow, D. et al., "Structure-activity relationships of monomeric C2-aryl pyrrolo[2,1-c][1,4]benzodiazepine (PBD) antitumor agents." J Med Chem. Apr. 8, 2010;53(7):2927-41.

Antonow, D. et al., "Synthesis of DNA-Interactive Pyrrolo [2,1-c][1,4] benzodiazepines (PBDs)" Chemical Reviews, 2011, 111(4):2815-2864.

Antonow, D. et al., "Parallel synthesis of a novel C2-aryl pyrrolo[2,1-c][1,4]benzodiazepine (PBD) library," J. Comb. Chem. (2007) 9:437-445.

Arai H., et al., "Molecular cloning of human endothelin receptors and their expression in vascular endothelial cells and smooth muscle cells," Jpn. Circ. J. 56, 1303-1307, 1992.

Arai H., et al., "The Human Endotbelin-B Receptor Gene. Structural Organization and Chromosomal Assignment," J. Biol. Chem. 268, 3463-3470, 1993.

Arima et al., "Studies on Tomaymycin, a New Antibiotic. I. Isolation and Properties of Tomaymycin," J. Antibiotics (1972) 25:437-444.

Arnould, S., "Impact on the cell cycle and involvement of ATM, ATR, chk1 and chk2 kinases in the cytotoxicity of SJG-136, a new pyrrolobenzodiazepine dimer," Proceedings of the American Association for Cancer Research Annual Meeting (Mar. 2004) 45:1298, Abstract No. 5618.

Arnould, S., "Time-dependent cytotoxicity induced by SJG-136 (NSC 694501): influence of the rate of interstrand cross-link formation on DNA damage signaling," Mol. Canc. Therap. 5(6):1602-1609 (2006).

(56) References Cited

OTHER PUBLICATIONS

Attie T., et al., "Mutation of the endothelin-receptor B gene in Waardenburg-Hirschsprung disease," Hum. Mol. Genet. 4, 2407-2409, 1995.
Auricchio A., et al., "Endothelin-B receptor mutations in patients with isolated Hirschsprung disease from a non-inbred population," Hum. Mol. Genet. 5:351-354, 1996.
Axup et al., "Synthesis of site-specific antibody-drug conjugates using unnatural amino acids." Proc Natl Acad Sci U S A. Oct. 2, 2012; 109(40):16101-6.
Bahrenberg et al., "Reduced Expression of PSCA, a Member of the LY-6 Family of Cell Surface Antigens, in Bladder, Esophagus, and Stomach Tumors," Biochem. Biophys. Res. Commun. (2000) 275(3):783-788.
Banker, G.S. et al., "Modern Pharmaceutics", Third edition, Marcel Dekker, New York (1996) 451 and 596.
Barel M., et al., "Evidence for a new transcript of the Epstein-Barr virus/C3d receptor (CR2, CD21) which is due to alternative exon usage," Mol. Immunol. 35, 1025-1031, 1998.
Barella et al., "Sequence variation of a novel heptahelical leucocyte receptor through alternative transcript formation," (1995) Biochem. J. 309:773-779.
Barnett T., et al., "Carcinoembryonic Antigen Family: Characterization of cDNAs Coding for NCA and CEA and Suggestion of Nonrandom Sequence Variation in Their Conserved Loop-Domains," Genomics 3, 59-66, 1988.
Batisse, et al., "A new delivery system for Auristatin in STxB-drug conjugate therapy." European J. Medicinal Chemistry, 2015, 95: 483-491.
Beck et al., "DNA Sequence Analysis of 66 kb of the Human MHC Class II Region Encoding a Cluster of Genes for Antigen Processing," (1992) J. Mol. Biol. 228:433-441.
Beck et al., "Evolutionary Dynamics of Non-coding Sequences Within the Class II Region of the Human MHC," (1996) J. Mol. Biol. 25 255:1-13.
Beck et al., "Strategies and challenges for the next generation of antibody-drug conjugates." Nature Reviews Drug Discovery, 16, 315-337 (2017).
Berge et al., "Pharmaceutical Salts," J. Pharm. Sci. (1977) 66:1-19.
Berry, J. M. et al., "Solid-phase synthesis of DNA-interactive pyrrolo[2,1-c][1,4]benzodiazepines," Tetrahedron Letters (2000) 41:6171-6174.
Berry, J.M. et al., "Synthesis and biological evaluation of an N10-Psec substituted pyrrolo[2,1-c][1,4]benzodiazepine prodrug," Bioorg. Med. Chem. Lett. (2002) 12:1413-1416.
Bien & Balcerska, "Serum Soluble Interleukin 2 receptor in human cancer of adults and children: a review," Biomarkers, 2008, 13(1): 1-26.
Blanc et al., "SAR3419: an anti-CD19-Maytansinoid Immunoconjugate for the treatment of B-cell malignancies," Clin Cancer Res., 2011, 17(20):6448-58.
Blumberg H., et al., "Interleukin 20: Discovery, Receptor Identification, and Role in Epidermal Function," Cell 104, 9-19, 2001.
Bose et al., "New Approaches to Pyrrolo[2,1-c][1,4]benzodiazepines: Synthesis, DNA-binding and cytotoxicity of DC-81," Tetrahedron, 48, 751-758 (1992).
Bose et al., "Stereospecific Synthesis of a Novel Zetido[2,1-c][1,4]-benzodiazepine (ABD) Ring System with DNA Recognition Potential" Tetrahedron Letters 1997, 38(33): 5839-5842.
Bose, D.S. et al., "Effect of linker length on DNA-binding affinity, cross-linking efficiency and cytotoxicity of C8 linked pyrrolobenzodiazepine dimers," J. Chem. Soc. Chem. Commun. (1992) 20:1518-1520.
Bose, D.S. et al., "Rational Design of a Highly Efficient Irreversible DNA Interstrand Cross-Linking Agent Based on the Pyrrolobenzodiazepine Ring System," J. Am. Chem. Soc., 114, 4939-4941 (1992).
Bourgeois C., et al., "Endothelin-1 and ETA Receptor Expression in Vascular Smooth Muscle Cells from Human Placenta: A New ETA Receptor Messenger Ribonucleic Acid Is Generated by Alternative Splicing of Exon 3," J. Clin. Endocrinol. Metab. 82, 3116-3123, 1997.
Brand et al., Prospect for anti-HER2 receptor therapy in breast cancer. Anticancer Res. Jan.-Feb. 2006;26(1B):463-70.
Brinster et al., "Introits increase transcriptional efficiency in transgenic mice," (1988) Proc. Natl. Acad. Sci. USA 85:836-840.
Buchman et al., "Comparison of Intron-Dependent and Intron-Independent Gene Expression," (1988) Mol. Cell. Biol. 8:4395-4405.
Buhrow, S.A., "LC-MS/MS assay and dog pharmacokinetics of the dimeric pyrrolobenzodiazepine SJG-136 (NSC 694501)," J. Chromat. B: Anal. Tech. Biomed. Life Sci. (2006) 840(1):56-62.
Burke, P.J. et al., "Anti-CD70 antibody-drug conjugates containing pyrrolobenzodiazepine dimers demonstrate robust antitumor activity," AACR National Meeting, Apr. 2012, Chicago, Illinois, Abstract No. 4631.
Burke, P.J. et al., "Novel immunoconjugates comprised of streptonigrin and 17-amino-geldanamycin attached via a dipeptide-p-aminobenzyl-amine linker system," Bioorg. Med. Chem. Lett., Apr. 2009, 19(10):2650-2653.
Calcutt, M.W., "Determination of chemically reduced pyrrolobenzodiazepine SJG-136 in human plasma by HPLC-MS/MS: application to an anticancer phase I dose escalation study," J. Mass Spectrom. (2008) 43(1):42-52.
Carl et al., "A Novel Connector Linkage Applicable in Prodrug Design," (1981) J. Med. Chem. 24:479-480.
Carlsson et al., "Protein Thiolation and Reversible Protein-Protein Conjugation," (1978) Biochem. J. 173:723-737.
Carter, P., "Potent antibody therapeutics by design," (2006) Nature Reviews Immunology 6:343-357.
Casset et al., "A peptide mimetic of an anti-CD4 monoclonal antibody by rational design." Biochem Biophys Res Commun. Jul. 18, 2003; 307(1):198-205.
CellTiter-Glo Luminescent Cell Viability Assay, Promega Corp. Technical Bulletin TB288, dated Jan. 13, 2012 (14 pages).
Chakravarty et al., "Plasmin—Activated Prodrugs for Cancer Chemotherapy. 2. Synthesis and Biological Activity of Peptidyl Derivatives of Doxorubicin," (1983) J. Med. Chern. 26:638-644.
Chan, J. and Watt, V.M., "eek and erk, new members of the eph subclass of receptor protein-tyrosine kinases," Oncogene 6 (6), 1057-1061 (1991).
Chang et al., "Molecular cloning of mesothelin, a differentiation antigen present on mesothelium, mesotheliomas, and ovarian cancers," Proc. Natl. Acad. Sci. U.S.A. 93 (1):136-140 (1996).
Chen, Z. et al., "A novel approach to the synthesis of cytotoxic C2—C3 unsaturated pyrrolo[2,1-c][1,4]benzodiazepines (PBDs) with conjugated acrylyl C2-substituents," Biorg. Med. Chem. Lett. (2004) 14:1547-1549.
Cheung, A., "Direct liquid chromatography determination of the reactive imine SJG-136 (NSC 694501)," J. Chromat. B: Anal. Techn. Biomed. Life Sci. (2005) 822(1-2):10-20.
Child et al., "Translational Control by an Upstream Open Reading Frame in the HER-2/neu Transcript," (1999) J. Bioi. Chern. 274: 24335-24341.
Cho et al., "Structure of the extracellular region of HER2 alone and in complex with the Herceptin Fab," Nature 421, 756-760, 2003.
Ciccodicola, A., et al., "Molecular characterization of a gene of the 'EGF family' expressed in undifferentiated human NTERA2 teratocarcinoma cells," EMBO J. 8 (7):1987-1991 (1989).
Cipolla, L., "Pyrrolo[2,1-c][1,4]benzodiazepine as a scaffold for the design and synthesis of anti-tumour drugs," Anti-Cancer Agents in Medicinal Chemistry (Jan. 2009) 9(1):1-31.
Clackson et al., "Making antibody fragments using phage display libraries," (1991) Nature, 352:624-628.
Clark H.F., et al., "The Secreted Protein Discovery Initiative (SPDI], a Large-Scale Effort to Identify Novel Human Secreted and Transmembrane Proteins: A Bioinformatics Assessment," Genome Res. 13, 2265-2270, 2003.
Clingen, P.H., "The role of nucleotide excision repair and homologous recomination in the sensitivity of mammalian cells to the minor groove crosslinking pyrrolo[2,1-c][1,4]benzodiazepine dimer

(56) References Cited

OTHER PUBLICATIONS

SJG-136 (NSC694501)," Proceedings of the American Association for Cancer Research Annual Meeting (Jul. 2003) 44:524.

Clingen, P.H., "the XPF-ERCC1 endonuclease and homologous recombination contribute to the repair of minor groove DNA interstrand crosslinks in mammalian cells produced by the pyrrolo[2,1-c][1,4]benzodiazepine dimer SJG-136," Nucl. Acids Res. (2005) 33(10):3283-3291.

Clinical Trial, "Translational research: 4 ways to fix the clinical trial." 2011, http://www.nature.com/news/2011/110928/full/477526a.html.

Clinical Trials Identifier NCT02034227, Safety, Tolerability Study of SG2000 in the Treatment of Advanced Chronic Lymphocytic Leukemia and Acute Myeloid Leukemia [online] NIH U.S. National Library of Medicine 2014 [Retrieved on Nov. 4, 2020]. Retrieved from the Internet: <https://www.clinicaltrials.gov/ct2/show/NCT02034227>.

Collins, "Generation and initial analysis of more than 15,000 full-length human and mouse cDNA sequences," Proc. Natl. Acad. Sci. U.S.A. 99 (26):16899-16903 (2002).

Cooper, N. et al., "Synthesis of novel PBDs as anti-tumour agents," Chem. Commun. (2002) 16:1764-1765.

Cooper, N., "Design, Synthesis and Evaluation of Novel C2-Aryl Pyrrolobenzodiazepines as Potential Anticancer Agents," Thesis submitted to School of Pharmacy, University of London, Dated Oct. 5, 2006.

Corey et al., "LuCap35: a new model of prostate cancer progression to androgen independence." The Prostate 2003;55:239-46.

Courtney, S. M. et al., "A new convenient procedure for the synthesis of pyrrolo[2,1-c][1,4]benzodiazepines", Tetrahedron Letters, vol. 34, No. 33, 5327-28 (1993).

Coussens L., et al., "Tyrosine Kinase Receptor with Extensive Homology to EGF Receptor Shares Chromosomal Location With neu Oncogene," Science (1985) 230(4730):1132-1139.

Cragg et al., "The alternative transcript of CD79b is overexpressed in B-CLL and inhibits signaling for apoptosis," Blood (2002) 100 (9):3068-3076.

Cree et al., "Methotrexate chemosensitivity by ATP luminescence in human leukemia cell lines and in breast cancer primary cultures: comparison of the TCA-100 assay with a clonogenic assay," (1995) AntiCancer Drugs 6:398-404.

Crouch et al., "The use of ATP bioluminescence as a measure of cell proliferation and cytotoxicity," (1993) J. Immunol. Meth. 160:81-88.

Dall'Acqua, W. F et al., "Antibody humanization by framework shuffling" Methods, 36, 43-60 (2005).

Dattolo, G. et al., "Polycondensed nitrogen heterocycles. IX. 5,6-dihydro-7H-pyrrolo[1,2-d][1,4]benzodiazepin-6-one," J. Heterocyclic. Chem. (1980) 17:701-703.

Davis et al., "Identification of a family of Fe receptor homo logs with preferential B cell expression," (2001) Proc. Natl. Acad. Sci. USA 98(17):9772-9777.

De Groot et al., "Cascade-Release Dendrimers" Liberate All End Groups upon a Single Triggering Event in the Dendritic Core, (2003) Angew. Chem. Int. Ed. 42:4490-4494.

De Groot et al., "Elongated Multiple Electronic Cascade and Cyclization Spacer Systems in Activatible Anticancer Prodrug for Enhanced Drug Release," (2001) J. Org. Chern. 66:8815-8830.

De Pascalis et al., "Grafting of "abbreviated" complementarity-determining regions containing specificity-determining residues essential for ligand contact to engineer a less immunogenic humanized monoclonal antibody." J Immunol. Sep. 15, 2002;169(6):3076-84.

Dennis et al., (2002) "Albumin Binding as a General Strategy For Improving the Pharmacokinetics of Proteins" J Biol Chem. 277:35035-35043.

Dijke, P., et al., "Characterization of Type I Receptors for Transforming Growth Factor-beta and Activin," Science 264 (5155):101-104 (1994).

Dimasi et al., "Efficient preparation of site specific antibody drug conjugates using cysteine insertion," Mol. Pharmaceutics 14 1501-1516 (2017).

Dimasi et al., "The Design and Characterization of Oligospecific Antibodies for Simultaneous Targeting of Multiple Disease Mediators" Journal of Molecular Biology, 2009, 393, 672-692.

Dobner et al., "Differentiation-specific expression of a novel G protein-coupled receptor from Burkitt's lymphoma," (1992) Eur. J. Immunol. 22:2795-2799.

Dong, Q. et al., "Reductive cleavage of TROC groups under neutral conditions with cadmium-lead couple," Tetrahedron Lett. (1995) 36(32):5681-5682.

Donnell et al., "Macrocyclic pyrrolobenzodiazepine dimers as antibody-drug conjugate payloads" Bioorganic & Medicinal Chemistry Letters (2017), 27(23): 5267-5271.

Dono et al., "Isolation and Characterization of the CRI PTO Autosomal Gene and Its X-linked Related Sequence," Am. J. Hum. Genet. 49:555-565, 1991.

Dornan et al., "Therapeutic potential of an anti-CD79b antibody-drug conjugate, anti-CD79b-vc-MMAE, for the treatment of non-Hodgkin lymphoma," (2009) Blood 114(13):2721-2729.

Doronina et al., "Enhanced Activity of Monomethylauristatin F through Monoclonal Antibody Delivery: Effects of Linker Technology on Efficacy and Toxicity," (2006) Bioconj. Chem. 17:114-124.

Doronina, S.O. et al., "Development of potent monoclonal antibody auristatin conjugates for cancer therapy," Nature Biotech. (2003) 21 :778-784.

Dorwald, F.Z., Side Reactions in Organic Synthesis: a Guide to Successful Synthesis Design, Weinheim: Wiley-VCH Verlag GmbH & Co., KGaA (2005) Preface.

Doyle, M., "Response of staphylococcus aureus to subinhibitory concentrations of a sequence-selective, DNA minor groove cross-linking pyrrolobenzodiazepine dimer," J. Antimicrob. Chemo., Aug. 2009, 64(5):949-959.

Dubowchik et al., "Cathepsin B-sensitive dipeptide prodrugs. 1. A model study of structural requirements for efficient release of doxorubicin." Bioorg Med Chem Lett. Dec. 1, 1998; 8(23):3341-6.

Dubowchik et al., "Cathepsin B-sensitive dipeptide prodrugs. 2. Models of anticancer drugs paclitaxel (Taxol), mitomycin C and doxorubicin." Bioorganic & Medicinal Chemistry Letters, 8:3347-3352, (1998).

Dubowchik et al., "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity," Bioconjugate Chem. (2002) 13, 855-869.

Dubowchik et al., "Monomethoxytrityl (MMT) as a Versatile Amino Protecting Group for Complex Prodrugs of Anticancer Compounds Sensitive to Strong Acids, Bases and Nucleophiles," (1997) Tetrahedron Letters. 38:5257-5260.

Dumoutier L., et al., "Cutting Edge: STAT Activation By IL-19, IL-20 and mda-7 Through IL-20 Receptor Complexes of Two Types," J. Immunol. 167, 3545-3549, 2001.

Dupont, C. et al., "Synthesis of rhazinilam analogue acting as an inhibitor of tubulin assembly," Tetrahedron Lett. (2000) 41:5853-5856.

Ehsani A., et al., "Characterization of a New Allele of the Human ERBB2 Gene by Allele-Specific Competition Hybridization," (1993) Genomics 15, 426-429.

Eliel et al., Stereochemistry of Organic Compounds, John Wiley & Sons, Inc., New York (1994).

Elshourbagy N.A., et al., "Molecular Characterization and Regulation of the Human Endothelin Receptors," J. Biol. Chem. 268, 3873-3879, 1993.

Erickson et al., "Antibody-Maytansinoid Conjugates Are Activated in Targeted Cancer Cells by Lysosomal Degradation and Linker-Dependent Intracellular Processing," (2006) Cancer Res. 66(8): 4426-4433.

Farmer, J.D. et al., "Synthesis and DNA crosslinking ability of a dimeric anthramycin analog," Tetrahedron Letters (1988) 29(40):5105-5108, Abstract only.

Farmer, J.D. et al., "DNA binding properties of a new class of linked anthramycin analogs,", Chemical Abstracts, Abstract No. 239940r, vol. 114, No. 25, 25 899-903 (1991).

(56) References Cited

OTHER PUBLICATIONS

Feild, J.A., et al., "Cloning and Functional Characterization of a Sodium-Dependent Phosphate Transporter Expressed in Human Lung and Small Intestine, " (1999) Biochem. Biophys. Res. Commun. 258 (3):578-582.
Fey, T. et al., "Silica-supported TEMPO catalyst: synthesis and application in the anelli oxidation of alcohols," J. Org. Chem. (2001) 66:8154-8159.
Fields, G. and Noble, R. (1990) "Solid phase peptide synthesis utilizing 9-fluoroenylmethoxycarbonyl amino acids", Int. J. Peptide Protein Res. 35:161-214.
Firsching, A. et al., "Antiproliferative and angiostatic activity of suramin analogues," Cancer Res. (1995) 55:4957-4961.
Flanagan et al., "The ephrins and Eph receptors in neural development," Annu. Rev. Neurosci. 21:309-345 (1998).
Flygare, "Antibody-drug conjugates for the treatment of cancer," Chem. Biol. & Drug Design (2013) 81(1):113-121.
Flynn et al., "Pre-Clinical Activity of Adct-301, a Novel Pyrrolobenzodiazepine (PBD) Dimer-Containing Antibody Drug Conjugate (ADC) Targeting CD25-Expressing Hematological Malignancies," Dec. 2014, https://www.researchgate.net/publication/275520174.
Foloppe, M.P. et al., "DNA-binding properties of pyrrolo[2,1-c][1,4]benzodiazephine N10-C11 amidines," Eur. J. Med. Chem., 31, 407-410 (1996).
Fox et al., "cDNA cloning and tissue distribution of five human EPH-like receptor protein-tyrosine kinases," Oncogene 10 (5):897-905 (1995).
Fuchs S., et al., "Functional Characterization of Three Mutations of the Endothelin B Receptor Gene in Patients With Hirschsprung's Disease: Evidence for Selective Loss of Gi Coupling," Mol. Med. 7, 115-124, 2001.
Fujisaku et al., "Genomic Organization and Polymorphisms of the Human C3d/Epstein-Barr Virus Receptor," (1989) J. Biol. Chem. 264 (4):2118-2125.
Fujisawa Pharmaceutical Co. Ltd., "Benzodiazepine derivatives," SciFinder Scholar, 2-3 (2002).
Fujisawa Pharmaceutical Co., Ltd., Abstract No. 139983k, "Benzodiazepine derivatives", Chemical Abstracts, vol. 99, No. 17, 603 (1983).
Fujisawa Pharmaceutical Co., Ltd., Abstract No. 72145x, "Benzodiazepine derivatives", Chemical Abstracts, vol. 98, No. 9, 638 (1983).
Fukuyama, T. et al., "Total Synthesis of (+)-Porothramycin B," Tetrahedron Letters, vol. 34, 16, 2577-2580 (1993).
Gallmeier, E., "Targeted disruption of FANCC and FANCG in human cancer provides a preclinical model for specific therapeutic options," Gastroenterology (2006) 130(7):2145-2154.
Gary S.C., et al., "cDNA cloning chromosomal localization, and expression analysis of human BEHAB/brevican, a brain specific proteoglycan regulated during cortical development and in glioma," Gene 256, 139-147, 2000.
Gaugitsch, H.W., et al., "A novel transiently expressed, integral membrane protein linked to cell activation. Molecular cloning via the rapid degradation signal AUUUA.," (1992) J. Biol. Chem. 267 (16):11267-11273.
Gavezzotti, A., "Are crystal structures predictable?" Acc. Chem. Res. (1994) 27:309-314.
Geiser et al "Automation of solid-phase peptide synthesis" in Macromolecular Sequencing and Synthesis, Alan R. Liss, Inc., 1988, pp. 199-218.
Genbank accession No. 11038674 (2013).
Genbank accession No. 20 NM_006424 (2013).
Genbank accession No. AAH32229, version No. AAH32229.1 GI:21619004, record update: Mar. 6, 2012.
Genbank accession No. AB040878 (2001).
Genbank accession No. AF116456 (1999).
Genbank accession No. AF179274 (2001).
Genbank accession No. AF229053 (2000).
Genbank accession No. AF343662 (2001).
Genbank accession No. AF343663 (2001).
Genbank accession No. AF343664 (2001).
Genbank accession No. AF343665 (2001).
Genbank accession No. AF361486 (2003).
Genbank accession No. AF369794 (2001).
Genbank accession No. AF397453 (2001).
Genbank accession No. AF455138 (2003).
Genbank accession No. AJ297436 (2008).
Genbank accession No. AK026467 (2006).
Genbank accession No. AK089756 (2010).
Genbank accession No. AK090423 (2006).
Genbank accession No. AK090475 (2006).
Genbank accession No. AL834187 (2008).
Genbank accession No. AX092328 (2001).
Genbank accession No. AY158090 (2003).
Genbank accession No. AY260763 (2003).
Genbank accession No. AY275463 (2003).
Genbank accession No. AY358085 (2003).
Genbank accession No. AY358628 (2003).
Genbank accession No. AY358907 (2003).
Genbank accession No. AY506558 (2004).
Genbank accession No. BC017023 (2006).
Genbank accession No. CAA76847.1 (2001).
Genbank accession No. CAF85723 (2004).
Genbank accession No. CQ782436 (2004).
Genbank accession No. M11730 (1995).
Genbank accession No. M18728 (1995).
Genbank accession No. M26004 (1993).
Genbank accession No. M76125, version No. M76125.1 GI:292869, 1995.
Genbank accession No. NM_000626 (2013).
Genbank accession No. NM_001178098.1 (2012).
Genbank accession No. NM_001203 (2013).
Genbank accession No. NM_003212 (2013).
Genbank accession No. NM_003486 (2013).
Genbank accession No. NM_004442 (2013).
Genbank accession No. NM_005823 (2013).
Genbank accession No. NM_012449 (2013).
Genbank accession No. NM_017636 (2013).
Genbank accession No. NM_030764 (2013).
Genbank accession No. NP 002111.1 (2013).
Genbank accession No. NP_001171569.1 (1992).
Genbank accession No. NP_001194 (2013).
Genbank accession No. NP_001707.1 (2013).
Genbank accession No. NP_001773.1 (2013).
Genbank accession No. NP_001774.10 (2013).
Genbank accession No. NP_002552.2 (2013).
Genbank accession No. NP_003203 (2013).
Genbank accession No. NP_005573.1 (2007).
Genbank accession No. NP_112571.1 (2007).
Geoghegan & Stroh, "Site-Directed Conjugation of Nonpeptide Groups to Peptides and Proteins via Periodate Oxidation of a 2-Amino Alcohol. Application to Modification at N-Terminal Serine," (1992) Bioconjugate Chem. 3:138-146.
Getz et al., "A Comparison between the Sulfhydryl Reductants Tris(2-carboxyethyl)phosphine and Dithiothreitol for Use in Protein Biochemistry," (1999) Anal. Biochem. vol. 273:73-80.
Glynne-Jones et al., "TENB2, a proteoglycan identified in prostate cancer that is associated with disease progression and androgen independence," (2001) Int J Cancer. Oct. 15; 94(2): 178-184.
Gordon et al., "Somatic hypermutation of the B cell receptor genes B29 (Igβ, CD79b) and mb1 (Igα, CD79a)," PNAS, Apr. 11, 2003, vol. 100, No. 7, 4126-4131.
Greene, T.W. and Wuts, P.G.M., Protective Groups in Organic Synthesis, John Wiley & Sons, 2nd ed., Ch 7, 315-345 (1991).
Greene, T.W. et al., Protective Groups in Organic Synthesis, John Wiley & Sons (1999) 3rd Edition, 503-549.
Greene, T.W. et al., Protective Groups in Organic Synthesis, John Wiley & Sons (1999) 3rd Edition, 23-200.
Gregson, S. et al., "Synthesis of a novel C2/C2'-exo unsaturated pyrrolobenzodiazepine cross-linking agent with remarkable DNA binding affinity and cytotoxicity," Chemical Communications, 797-798 (1999).

(56) References Cited

OTHER PUBLICATIONS

Gregson, S.J. et al., "Effect of C2/C3-endo unsaturation on the cytotoxicity and DNA-binding reactivity of pyrrolo-[2,1-c][1,4]-benzodiazepines," Bioorg. Med. Chem. Lett. (2000) 10(16):1849-1851.
Gregson, S.J. et al., "Linker length modulates DNA cross-linking reactivity and cytotoxic potency of C8/C8' ether-linked C2-exo-unsaturated pyrrolo[2,1-c][1,4]benzodiazepine (PBD) dimers," J. Med. Chem. (2004) 1161-1174.
Gregson, S.J. et al., "Synthesis of the first example of a C2-C3/C2'-C3'-endo unsaturated pyrrolo[2,1- c][1,4]benzodiazepine dimer," Biorg. Med. Chem. Lett. (2001) 11:2859-2862.
Gregson, S.J. et al., "Synthesis of the first examples of A-C8/C-C2 amide-linked pyrrolo[2,1- c][1,4]benzodiazepine dimers," Biorg. Med. Chem. Lett. (2003) 13:2277-2280.
Gregson, S.J. et al., "Design, Synthesis and Evaluation of a Novel Pyrrolobenzodiazepine DNA-Interactive Agent with Highly Efficient Cross-Linking Ability and Potent Cytotoxicity", J. Med. Chem., 44: 737-748 (2001).
Gregson, S.J. et al., "Effect of C2-exo Unsaturation on the Cytotoxicity and DNA—Binding Reactivity of Pyrrolo[2,1-c]1,4]benzodiazepines", Bioorganic & Medicinal Chemistry Letters, 10: 1845-1847 (2000).
Gu, Z. et al., "Prostate stem cell antigen (PSCA) expression increases with high gleason score, advanced stage and bone metastasis in prostate cancer," Oncogene 19, 1288-1296, 2000.
Guichard, S.M., "Influence of P-glycoprotein expression on in vitro cytotoxicity and in vivo antitumour activity of the novel pyrrolobenzodiazepine dimer SJG-136," Eur. J. Cancer (2005) 41(12):1811-1818.
Guiotto, A. et al., "Synthesis of novel C7-aryl substituted pyrrolo[2,1-c][1,4]benzodiazepines (PBDs) via Pro-N10-troc protection and suzuki coupling," Bioorganic & Medicinal Chemistry Letters, 8, No. 21, 3017-3018 (1998).
Guselnikov et al., "A family of highly diverse human and mouse genes structurally links leukocyte FcR, gp42 and PECAM-1," Immunogenetics 54 (2):87-95 (2002).
Ha et al., "molecular cloning and expression pattern of a human gene homologous to the murine mb-1 gene," (1992) J. Immunol. 148(5):1526-1531.
Hadjivassileva, T., "Antibacterial activity of pyrrolobenzodiazepine dimers, a novel group of DNA-binding compounds," Abstracts of the Interscience Conference on Antimicrobial Agents and Chemotherapy (Oct.-Nov. 2004) 44:202.
Hadjivassileva, T., "Interactions of pyrrolobenzodiazepine dimers and duplex DNA from methicillin-resistant *Staphylococcus aureus*," Int. J. Antimicrob. Agents (2007) 29(6):672-678.
Hadjivassileva, T., "Pyrrolobenzodiazepine dimers: novel sequence-selective, DNA-interactive, cross-linking agents with activity against Gram-positive bacteria," J. Antimicrob. Chemo. (2005) 56(3):513-518.
Haendler B., et al., "Molecular Cloning of Human Endothelin (ET) Receptors ETA and ETB," J. Cardiovasc. Pharmacal. 20, s1-S4, 1992.
Haisma et al., "Comparison of two antracycline-based prodrugs for activation by a monoclonal antibody-β-glucuronidase conjugate in the specific treatment of cancer." Cell biophysics, Humana Press Inc. 1994, 24/25: 185-192.
Hamaguchi, A., "DNA cross-linking and in vivo antitumour activity of the extended pyrrolo[2,1-c][1,4]benzodiazepine dimer SG2057 (DRG-16)," EJC Supplements (Nov. 2006) 4(12):96.
Hamann P. "Monoclonal antibody-drug conjugates," (2005) Expert Opin. Ther. Patents 15(9):1087-1103.
Hamblett et al., "Effects of Drug Loading on the Antitumor Activity of a Monoclonal Antibody Drug Conjugate," (2004) Clin. Cancer Res. 10:7063-7070.
Handbook of Food Additives, 2nd Ed. (eds. M. Ash and I. Ash), Synapse Information Resources, Inc., Endicott, New York, USA (2001).
Handbook of Pharmaceutical Excipients, 2nd edition, 1994, Edited by Ainley Wade and Paul J. Weller.
Hara et al., "DC 102, a new glycosidic pyrrolo(1,4)benzodiazepine antibiotic produced by *Streptomyces* sp.", J. Antibiotics, 41, 702-704 (1988).
Hartley J A: "The development of pyrrolobenzodiazepines as antitumour agents", Expert Opinion on Investigational Drugs, Ashley Publications Ltd., vol. 28, No. 6, Jan. 1, 2011, pp. 733-744.
Hartley, J.A. et al., "Abstract 2856: pyrrolobenzodiazepine (PBD) dimers—potent next generation warheads in antibody drug conjugates (ADCs) targeted at both solid and haematological tumors," Cancer Res. (2013) 78(8)Supp 1:2856.
Hartley, J.A et al., "SG2285, a novel C2-aryl-substituted pyrrolobenzodiazepine dimer prodrug that cross-links DNA and exerts highly potent antitumor activity," Cancer Res., Sep. 2010, 70(17):6849-6858.
Hartley, J.A. et al., "SJG-136 (NSC 694501), a novel rationally designed DNA minor groove interstrand cross-linking agent with potent and broad spectrum antitumor activity. Part 1: Cellular pharmacology, in vitro and initial in vivo antitumor activity," Cancer Res. (2004) 64:6693-6699.
Hartley, J.A., "In vitro antitumor activity and in vivo DNA interstrand crosslinking by the novel pyrrolobenzodiazepine dimer SJG-136 (NSC 694501)," Proceedings of the American Association for Cancer Research Annual Meeting (Mar. 2002) 43:489.
Hartley, J.A., "SJG-136 (NSC-D694501)—a novel DNA sequence specific minor groove crosslinking agent with significant antitumor activity," Proceedings of the American Association for Cancer Research Annual Meeting (Mar. 2000) 41:425.
Hashimoto et al., "Chromosomal localization, genomic structure, and allelic polymorphism of the human CD79a (lg-alpha/mb-1) gene," (1994) Immunogenetics 40(4 ):287-295.
Hay et al., "A 2-nitroimidazole carbamate prodrug of 5-amin0-1-(chloromethyl)-3-[(5,6,7-trimethoxyindol-2-yl)carbonyl]-1,2-dihydr0-3h -benz[e]indole (amino-seco-cbi-tmi) for use with adept and gdept," (1999) Bioorg. Med. Chem. Lett. 9:2237-2242.
Herdwijn et al., "Synthesis of trans(+ )6-phenoxyacetamido-1-methylene-3,3-dicarboxymethyl-1-carbapenam," Canadian Journal of Chemistry. 1982, 60, 2903-2907.
Hermanson, G.T., "Heterobifunctional Cross-linkers," (1996) Bioconjugate Techniques; Academic Press: New York, p. 228-286.
Hochhauser, D., "Phase I study of sequence-selective minor groove DNA binding agent SJG-136 in patients with advanced solid tumors," Clin. Cancer Res., Mar. 2009, 15(6):2140-2147.
Hochlowski, J. et al., "Abbeymycin, a new anthramycin-type antibiotic produced by a streptomycete," J. Antibiotics, 40, 145-148 (1987).
Hofstra R.M.W., et al., "A homozygous mUtation in the endothelin-3 gene associated with a combined Waardenburg type 2 and Hirschsprung phenotype (Shah-Waardenburg syndrome)" Nat. Genet. 12, 445-447, 1996.
Hofstra R.M.W., et al., "Mutations in Hirschsprung Disease: When Does a Mutation Contribute to the Phenotype," Eur. J. Hum. Genet. 5, 180-185, 1997.
Horie et al., "Identification and Characterization of TMEFF2, a Novel Surviv Factor for Hippocampal and Mesencephalic Neurons," (2000) Genomics 67: 146-152.
Howard, P.W. et al., "Design, synthesis and biological evaluation of ZC-423, a novel C2-aryl substituted pyrrolobenzodiazepine (PBD) dimer," Clinical Cancer Research (2005) 11(23):9015S-9016S (A205).
Howard, P.W. et al., "Synthesis of a novel C2/C2'-aryl-substituted pyrrolo[2,1-c][1,4]benzodiazepine dimer prodrug with improved water solubility and reduced DNA reaction rate," Bioorg. Med. Chem., Sep. 2009, In Press, 4 pages now: Sep. 2009, 19:6463-6466.
Howard, P.W. et al., "The design, synthesis and biological evaluation of a set of C2-aryl substituted pyrrolo[2,1-c][1,4]benzodiazepine dimers," EJC Supplements (2006) 4(12):95—Poster Abstract 301.
Howard, P.W., "Design, synthesis and biological evaluation of novel C2-aryl-substituted pyrrolo[2,1-c][1,4]benzodiazepine monomers," Proceedings of the American Association for Cancer Research Annual Meeting (Apr. 2006) 47:132.

(56) References Cited

OTHER PUBLICATIONS

Hubert, R.S., et al., "STEAP: A prostate-specific cell-surface antigen highly expressed in human prostate tumors," (1999) Proc. Natl. Acad. Sci. U.S.A. 96 (25):14523-14528.
Hurley, L. and Needham-Vandevanter, D., "Covalent Binding of Antitumor Antibiotics in the Minor Groove of DNA. Mechanism of Action of CC-1065 and the pyrrolo(1,4)benzodiazepines," Acc. Chem. Res., 19, 230-237 (1986).
Ide et al., "Cloning of human bone morphogenetic protein type IB receptor (BMPRIB) and its expression in prostate cancer in comparison with other BMPRs," Oncogene (1997) 14, 1377-1382.
Iida, H. et al. "Design and synthesis of pyrrolo[2,1-c][1,4]benzodiazepine (PBD)—polyaminoalkyl conjugates by the use of SNA4 reaction 2-nitro-5-fluorobenzoate precursor as key reaction, " Heterocycles (2004) 62:693-711.
International Search Report and Written Opinion dated Dec. 21, 2012 for Int. Appl. No. PCT/US2012/059864 (7 pages).
International Search Report and Written Opinion for Application No. PCT/EP2012/070233 dated Jan. 28, 2013 (8 pages).
International Search Report and Written Opinion for Application No. PCT/EP2013/071346 dated Feb. 5, 2014 (11 pages).
International Search Report and Written Opinion for Application No. PCT/EP2013/071352 dated Feb. 5, 2014 (14 pages).
International Search Report and Written Opinion for Application No. PCT/EP2014/054958 dated Jul. 2, 2014 (13 pages).
International Search Report and Written Opinion for Application No. PCT/GB2015/052629 dated Nov. 2, 2015 (12 pages).
International Search Report and Written Opinion for Application No. PCT/US2011/032664 dated Aug. 19, 2011 (13 pages).
International Search Report and Written Opinion for Application No. PCT/US2011/032668 dated May 26, 2011 (12 pages).
International Search Report and Written Opinion for Application No. PCT/US2015/050634 dated Jan. 29, 2016 (14 pages).
International Search Report and Written Opinion for Application No. PCT/EP2018/053163 dated Apr. 4, 2018, 10 pages.
International Search Report and Written Opinion for Application No. PCT/EP2018/053162 dated Apr. 24, 2018 (9 pages).
International Search Report and Written Opinion for Application No. PCT/EP2018/081079 dated Feb. 19, 2019 (12 pages).
International Search Report and Written Opinion mailed Jan. 30, 2020, Int. Appl. No. PCT/EP2019/078383, 14 pages.
International Search Report and Written Opinion mailed Jan. 30, 2020, Int. Appl. No. PCT/EP2019/078402, 10 pages.
International Search Report and Written Opinion mailed Jun. 13, 2019, Int. Appl. No. PCT/EP2019/055116, 6 pages.
International Search Report and Written Opinion mailed May 6, 2020, Int. Appl. No. PCT/EP2020057837, 10 pages.
Iontcho R Vlahov et al., "Preparation of pyrrolobenzodiazepine peptide conjugates for treating cancer diseases." WO2017172930, Oct. 5, 2017 pp. 1-6.
Itoh et al., "Sibanomicin, a new pyrrolo(1,4)benzodiazepine antitumor antibiotic produced by a *Micromonospora* sp." J. Antibiotics, 41, 1281-1284 (1988).
Janjigian, Y.Y., "A phase I trial of SJG-136 (NSC#694501) in advanced solid tumors," Cancer Chemotherapy and Pharmacology, Aug. 2009, 65(5):833-838.
Jeffrey et al., "A Potent Anti-CD70 Antibody-Drug Conjugate Combining a Dimeric Pyrrolobenzodiazepine Drug with Site-Specific Conjugation Technology." Bioconj. Chem. 2013, 24, 1256-1263.
Jeffrey et al., "Development and properties of beta-glucuronide linkers for monoclonal antibody-drug conjugates." Bioconjugate Chemistry, 5, 2006, 17, 831-840. (Abstract).
Jeffrey, S.C. et al., "Development of Pyrrolobenzodiazepine-Based Antibody-Drug Conjugates for Cancer," AACR Annual Meeting 2013, Abstract No. 4321.
Jeffrey, S.C., "Design, synthesis, and in vitro evaluation of dipeptide-based antibody minor groove binder conjugates," J. Med. Chem. (2005) 48(5):1344-1358.

Jespers, L. S., "Guiding the Selection of Human Antibodies from Phage Display Repertoires to a Single Epitope of an Antigen" Nature Biotech., 12, 899-903 (1994).
Jia, L., "Interspecies differences in pharmacokinetics and time-dissociated toxicokinetics of SJG-136," Proceedings of the American Association for Cancer Research Annual Meeting (Mar. 2004) 45:487.
Jia, L., "Use of the comet assay as a surrogate biomarker for the in vivo measurement of DNA damage to lymphocytes," Proceedings of the American Association for Cancer Research Annual Meeting (Mar. 2004) 45:452-453.
Johnson & Goldin, "The clinical impact of screening and other experimental tumor studies." Cancer Treat Rev. Mar. 1975; 2(1):1-31.
Jones et al., "Releasable Luciferin—Transporter Conjugates: Tools for the Real-Time Analysis of Cellular Uptake and Release," J. Am. Chem. Soc., 2006, 128, 6526-6527.
Jonsson et al., "Human class II DNA and DOB genes display low sequence variability," (1989) Immunogenetics 29(6):411-413.
Jordan, V.C., "Tamoxifen: a most unlikely pioneering medicine," Nature Reviews: Drug Discovery (2003) 2:205-213.
Junutula et al., "Rapid identification of reactive cysteine residues for site-specific labeling of antibody-Fabs," (2008) Jour of Immun. Methods 332:41-52.
Junutula, et al., "Site-specific conjugation of a cytotoxic drug to an antibody improves the therapeutic index," 2008b Nature Biotech., 26(8):925-932.
Kamal et a., "Pyrrolo[2,1-c][1,4]benzodiazepine-β-glucuronide prodrugs with a potential for selective therapy of solid tumors by PMT and ADEPT strategies" Bioorganic & Medicinal Chemistry Letters 2008, 18:3769-3773.
Kamal et al., "Synthesis and DNA-binding affinity of A-C8/C-C2 alkoxyamido-linked pyrrolo[2,1-c][1,4]benzodiazepine dimers" Biorg. Med. Chem. Lett. (2003) 13(22):3955-3958.
Kamal, A. et al., "Design, synthesis and evaluation of new noncross-linking pyrrolobenzodiazepine dimers with efficient DNA binding ability and potent antitumor activity," J. Med. Chem. (2002) 45:4679-4688.
Kamal, A., "Development of pyrrolo[2,1-c][1,4]benzodiazepine beta-galactoside prodrugs for selective therapy of cancer by ADEPT and PMT," Chemmedchem (2008) 3:794-802.
Kamal, A., "Remarkable DNA binding affinity and potential anti-cancer activity of pyrrolo[2,1-c][1,4]benzodiazepine-naphthalamide conjugates linked through piperazine side-armed alkane spacers," Bioorg. Med. Chem. (2008) 16(15):7218-7224.
Kamal, A., "Remarkable enhancement in the DNA-binding ability of C2-fluoro substituted pyrrolo[2,1-c][1,4]benzodiazepines and their anticancer potential," Bioorg. Med. Chem., Jan. 2009, 17(4):1557-1572.
Kamal, A., "Synthesis of fluorinated analogues of SJG-136 and their DNA-binding potential," Bioorg. Med. Chem. Lett (2004) 14(22):5699-5702.
Kamal, A., et al., "An Efficient Synthesis of Pyrrolo[2,1-c][1,4] Benzodiazepine Antibiotics via Reductive Cyclization," Bioorg. Med. Chem. Ltrs, 7, No. 14, 1825-1828 (1997).
Kamal, A., et al., "Synthesis of Pyrrolo [2,1-c][1,4]-Benzodiazepene Antibiotics: Oxidation of Cyclic Secondary Amine with TPAP", Tetrahedron, v. 53, No. 9, 3223-3230 (1997).
Kamal, et al., "Synthesis of pyrrolo[2,1-c][1,4]benzodiazepines via reductive cyclization of w-azido carbonyl compounds by TMSI: an efficient preparation of antibiotic DC-81 and its dimers," Biorg. Med. Chem. Lett. (2000) 10:2311-2313.
Kaneko, T. et al., "Bicyclic and tricyclic analogues of anthramycin," J. Med. Chem. (1985) 28:388-392.
Kang, G.-D. et al., "Synthesis of a novel C2-aryl substituted 1,2-unsaturated pyrrolobenzodiazepine," Chem. Commun. (2003) 1680-1689.
Kasahara et al., "Nucleotide sequence of a chimpanzee DOB eDNA clone," (1989) Immunogenetics 30(1):66-68.
King et al., "Facile synthesis of maleimide bifunctional Jinkers," (2002) Tetrahedron Letters 43:1987-1990.
Kingsbury et al., "A Novel Peptide Delivery System Involving Peptidase Activated Prodrugs as Antimicrobial Agents. Synthesis

(56) References Cited

OTHER PUBLICATIONS and Biological Activity of Peptidyl Derivatives of 5 Fluorouracil," (1984) J. Med. Chem. 27:1447-1451.
Kitamura et al., "Synthetic study of (+)-anthramycin using ring-closing enyne metathesis and cross-metathesis," Tetrahedron 2004, 60, 9649-9657.
Kohler et al., "Continuous cultures of fused cells secreting antibody of predefined specificity," (1975) Nature 256:495-497.
Kohn, K., "Anthramycin," Antibiotics III, Springer-Verlag, NY, 3-11 (1975).
Kojima et al., "Molecular Cloning and Expression of Megakaryocyte Potentiating Factor cDNA," The Journal of Biological Chemistry, vol. 270, No. 37, Issue of Sep. 15, pp. 21984-21990, 1995.
Konishi, M. et al., "Chicamycin, a new antitumor antibiotic II. Structure determination of chicamycins A and B," J. Antibiotics, 37, 200-206 (1984).
Kovtun et al., "Antibody-Drug Conjugates Designed to Eradicate Tumors with Homogeneous and Heterogeneous Expression of the Target Antigen," (2006) Cancer Res. 66(6):3214-3121.
Kreitman et al., "Phase I Trial of Recombinant Immunotoxin Anti-Tac(Fv)-PE38 (LMB-2) in Patients with Hematologic Malignancies," J. Clin. Oncol., 2000, 18:1622-1636.
Kuhns J.J., et al., "Poor Binding of a HER-2/neu Epitope (GP2) to HLA-A2.1 is due to a Lack of Interactions with the Center of the Peptide," J. Biol. Chem. 274, 36422-36427, 1999.
Kumar et al., "Antibody drug conjugates," Annual Reports in Medicinal Chemistry 2017, 50 441-480.
Kuminoto, et al., "Mazethramycin, a new member of anthramycin group antibiotics" J Antibiot (Tokyo) Jun. 1980; 33(6):665-7.
Kurebayashi et al., "Isolation and characterization of a new human breast cancer cell line, KPL-4, expressing the Erb B family receptors and interleukin•6," (1999) Brit. Jour. Cancer 79(5-6):707-717.
Lambert, "Drug-conjugated monoclonal antibodies for the treatment of cancer," (2005) Current Opin.In Pharmacal. 5:543-549.
Langley, D.R. and Thurston, D.E., "A versatile and efficient synthesis of carbinolamine-containing pyrrolo[1,4]benzodiazepines via the cyclization of N-92-aminobenzoyl)pyrrolidine-2-carboxaldehyde diethyl thioacetals: total synthesis of prothracarcin," J. Org. Chem., 52, 91-97 (1987).
Langlois, N. et al., "Synthesis and cytotoxicity on sensitive and doxorubicin-resistant cell lines of new pyrrolo[2,1-c][1,4]benzodiazepines related to anthramycin," J. Med. Chem. (2001) 44:3754-3757.
Larhammar et al., "Sequence of Gene and cDNA Encoding Murine Major Histocompatibility Complex Class II Gene AP2*," (1985) J. Biol. Chem. 260(26):14111-14119.
Launay et al., "TRPM4 is a Ca2+-Activated Nonselective Cation Channel Mediating Cell Membrane Depolarization," Cell 109 (3):397-407 (2002).
Law et al., "Lymphocyte Activation Antigen CD70 Expressed by Renal Cell Carcinoma is a Potential Therapeutic Target for Anti-CD70 Antibody-Drug Conjugates," (2006) Cancer Res. 66(4):2328-2337.
Lazar et al., "A molecular immunology approach to antibody humanization and functional optimization" Molecular Immunology, 2007, 44(8), 1986-1998.
Le et al., "Primary structure and expression of a naturally truncated human P2X ATP receptor subunit from brain and immune system," (1997) FEBS Lett. 418(1-2):195-199.
Leabman; et al., "Effects of altered FcγR binding on antibody pharmacokinetics in cynomolgus monkeys." MAbs. Nov.-Dec. 2013; 5(6):896-903.
Leber, J.D. et al., "A revised structure for sibiromycin," J. Am. Chem. Soc., 110, 2992-2993 (1988).
Ledford et al., "Total Synthesis of (+)-Trehazolin: Optically Active Spirocycloheptadienes as Useful Precursors for the Synthesis of Amino Cyclopentitols." J. Am. Chem. Soc. 1995, 117, 47, 11811-11812.
Leimgruber, W. et al., "Isolation and characterization of anthramycin, a new antitumor antibiotic," J. Am. Chem. Soc., 87, 5791-5793 (1965).
Leimgruber, W. et al., "The structure of anthramycin," J. Am. Chem. Soc., 87, 5793-5795 (1965).
Leimgruber, W. et al., "Total synthesis of anthramycin," J. Am. Chem. Soc., 90, 5641-5643 (1968).
Leonard et al., "Phase I/II trial of epratuzumab (humanized anti-CD22 antibody) in indolent non-Hodgkin's lymphoma," J. Clin. Oncology (2003) 21(16):3051-3059.
Leonard et al., "Preclinical and clinical evaluation of epratuzumab (anti-CD22 IgG) in B-cell malignancies," Oncogene (2007) 26:3704-3713.
Leung et al., "Construction and characterization of a humanized, internalizing, B-cell (CD22)-specific, leukemia/lymphoma antibody, LL2," Mol. Immunol. (1995) 32(17-18):1413-1427.
Levenson et al., "MCF-7: The First Hormone-responsive Breast Cancer Cell Line," (1997) Cancer Res. 57(15):3071-3078.
Lewis Phillips et al., "Targeting HER2-Positive Breast Cancer with Trastuzumab-DM1, an Antibody—Cytotoxic Drug Conjugate," Cancer Res, 2008, 68: (22).
Liang et al., "The Gene for a Novel Transmembrane Protein Containing Epidermal Growth Factor and Follistatin Domains Is Frequently Hypermethylated in Human Tumor Cells," (2000) Cancer Res. 60:4907-4912.
Linden et al., "Dose-fractionated radioimmunotherapy in non-Hodgkin's lymphoma using DOTA-conjugated, 90Y-radiolabeled, humanized anti-CD22 monoclonal antibody, epratuzumab," J. Clin. Cancer Res. (2005) 11:5215-5222.
Lonberg, "Fully Human antibodies from transgenic mouse and phage display platforms" Curr. Opinion, 20(4), 450-459 (2008).
Lown et al., "Molecular Mechanism of Binding of Pyrrolo(1,4)benzodiazepine antitumour agents to deoxyribonucleic acid—anthramycin and tomaymycin," Biochem. Pharmacol. (1979), 28 (13), 2017-2026.
Manfre et al., "Syntheses of Proline Analogues as Potential Mechanism-Based Inhibitors of Proline Dehydrogenase:4-Methylene-L-, (E)- and (Z)-4-(Fluoromethylene)-L-, cis- and trans-5-Ethynyl-(±)-, and cis- and trans -5-Vinyl-L- proline," J. Org. Chem. 1992, 57, 2060-2065.
Mantaj et al., "From Anthramycin to Pyrrolobenzodiazepine (PBD)—Containing Antibody-Drug Conjugates (ADCs)" Angew. Chem. Int. Ed. 2017, 56, 462-488.
Marin, D., "Voltammetric studies of the interaction of pyrrolo[2,1-][1,4]benzodiazepine (PBD) monomers and dimers with DNA," J. Electroanal. Chem. (2006) 593(1-2):241-246.
Marks et al., "By-passing Immunization, Human Antibodies from V-gene Libraries Displayed on Phage," (1991) J. Mol. Biol., 222:581-597.
Martin, C. et al., "Sequence-selective interaction of the minor-groove interstrand cross-linking agent SJG-136 with naked and cellular DNA: footprinting and enzyme inhibition studies," Biochem. (2005) 44(11):4135-4147.
Masterson et al "Synthesis and biological evaluation of novel pyrrolo[2,1-c][1,4]benzodiazepine prodrugs for use in antibody-directed enzyme prodrug therapy.", Bioorganic & Medicinal Chemistry Letters, vol. 16., No. 2, Jan. 15, 2006, pp. 252-256.
Mastroberardino et al., "Amino-acid transport by heterodimers of 4F2hc/CD98 and members of a permease family," Nature 395 (6699):288-291 (1998).
Matsumoto, K. et al., "Synthesis of polyaminoalkyl substituted conjugates of pyrrolo[2,1-c][1,4]benzodiazepine (PBD)-polyaminoalkyl involving SNA4 reaction of 2-nitro-5-fluorobenzoate precursors," Heterocycles (2000) 52(3):1015-1020.
McDonagh, "Engineered antibody-drug conjugates with defined sites and stoichiometries of drug attachment," (2006) Protein Eng. Design & Sel. 19(7): 299-307.
Mendoza et al., "Inhibition of Ligand-mediated HER2 Activation in Androgen-independent Prostate Cancer," (2002) Cancer Res. 62:5485-5488.
Miller et al., "Design, Construction, and In Vitro Analyses of Multivalent Antibodies," (2003) Jour. of Immunology 170:4854-4861.

(56) References Cited

OTHER PUBLICATIONS

Miller et al., "IRTAs: a new family of immunoglobulinlike receptors differentially expressed in B cells," Blood 99 (8):2662-2669 (2002).
Miura et al., "Molecular cloning of a human RP105 homologue and chromosomal localization of the mouse and human RP105 genes (Ly64 and LY64)." Genomics. Dec. 15, 1996; 38(3):299-304.
Miura et al., "RPIOS is Associated With MD-1 and Transmits an Activation Signal in Human B Cells," (1998) Blood 92:2815-2822.
Moore M., et al., "Molecular cloning of the eDNA encoding the Epstein-Barr virus/C3d receptor (complement receptor type 2) of human B lymphocytes," Proc. Natl. Acad. Sci. U.S.A. 84, 9194-9198, 1987.
Mori, M. et al., "Total syntheses of prothracarcin and tomaymycin by use of palladium catalyzed carbonylation," Tetrahedron (1986) 42(14):3793-3806.
Morrison et al., "Chimeric human antibody molecules: Mouse antigen-binding domains with human constant region domains," (1984) Proc. Natl. Acad. Sci. USA, 81:6851-6855.
Mountzouris, J.A. et al., "Comparison of a DSB-120 DNA interstrand cross-linked adduct with the corresponding bis-Tomamycin adduct," J. Med. Chem. (1994) 37:3132-3140.
Muller et al., "Cloning and sequencing of the eDNA encoding the human homologue of the murine immunoglobulin-associated protein B29," (1992) Eur. J. Immunol. 22 (6): 1621-1625.
Mungall A.J., et al., "The DNA sequence and analysis of human chromosome 6," Nature 425, 805-811, 2003.
Murphy et al., "Concise, Stereoselective Route to the Four Diastereoisomers of 4-Methylproline." J. Nat. Prod. 2008, 71: 806-809.
Nadler et al., "B4, a human B lymphocyte-associated antigen expressed on normal, mitogen-activated, and malignant B lymphocytes," Journal of Immunology, 1983, 131(1):244-250.
Nagasaka, T. and Koseki, Y, "Stereoselective Synthesis of Tilivalline," Journal of Organic Chemistry, vol. 63, No. 20, 6797-6801 (1998).
Nagasaka, T. et al., "Stereoselective Synthesis of Tilivalline," Tetrahedron Letters, 30:14, 1871-1872 (1989).
Nagase T., et al., "Prediction of the Coding Sequences of Unidentified Human Genes. XVII. The Complete Sequences of 100 New eDNA Clones from Brain Which Code for Large Proteins in vitro," (2000) DNA Res. 7 (2):143-150.
Nakamuta M., et al., "Cloning and sequence analysis of a cDNA encoding human non-selective type of endothelin receptor," Biochem. Biophys. Res. Commun. 177, 34-39, 1991.
Nakayama et al., "Altered Gene Expression upon BCR Cross-Linking in Burkitt's Lymphoma B Cell Line," (2000) Biochem. Biophys. Res. Commun. 277(1):124-127.
Narayanaswamy, M., "A novel HPLC/MS assay to measure DNA interstrand cross-linking efficacy in oligonucleotides of varying sequence," EJC Supplements (Nov. 2006) 4(12):92-93.
Narayanaswamy, M., "An assay combining high-performance liquid chromatography and mass spectrometry to measure DNA interstrand cross-linking efficiency in oligonucleotides of varying sequences," Anal. Biochem. (2008) 374(1):173-181.
Narayanaswamy, M., "Use of HPLC-MS to characterize novel mono and intrastrand cross-linked DNA adducts formed by the sequence-selective DNA-interactive agent SJG-136," Proceedings of the American Association for Cancer Research Annual Meeting (Apr. 2007) 48:760-761.
Narukawa, Y., "General and efficient synthesis of 2-alkylcarbapenems synthesis of dethia carba analogs of clinically useful carbapenems via palladium-catalyzed cross-coupling reaction," Tetrahedron (1997) 53:539-556.
Naruse et al., "The HLA-DOB gene displays limited polymorphism with only one amino acid substitution," (2002) Tissue Antigens 59:512-519.
Neuberger and Williams, "The intron requirement for immunoglobulin gene expression is dependent upon the promoter," (1988) Nucleic Acids Res. 16:6713-6724.

Nicolaou et al., "Calicheamicin θ: A Rationally Designed Molecule with Extremely Potent and Selective DNA Cleaving Properties and Apoptosis Inducing Activity," Angew Chem. Intl. Ed. Engl. (1994) 33:183-186.
Nilius et al., "Voltage Dependence of the Ca2+activated Cation Channel TRPM4," the Journal of Biological Chemistry, vol. 278, No. 33, Issue of Aug. 15, pp. 30813-30820, 2003.
O'Neil, Chemical Abstract No. 171573p, "The synthesis of Functionalized Pyrrolo-[2,1-c][1,4]-Benzodiazepines", Chemical Abstracts, vol. 126, No. 13, 618 (1997).
O'Neil, I.A., et al., "The Synthesis of Functionalized Pyrrolo-[2,1-c][1,4]-Benzodiazepines," Synlett, 75-78 (1997).
Ogawa Y., et al., "Molecular Cloning of a Non-Isopeptide-Selective Human Endothelin Receptor," Biochem. Biophys. Res. Commun. 178, 248-255, 1991.
Okamoto Y., et al. "Palmitoylation of Human Endothelin B," Biol. Chem. 272, 21589-21596, 1997.
O'Neil, I.A. et al., "DPPE: A Convenient Replacement for Triphenylphosphine in the Staudinger and Mitsunobu Reactions", Tetrahedron Letters, vol. 39, No. 42, 7787-7790 (1998).
Parrish-Novak J., et al., "Interleukins 19, 20, and 24 Signal through Two Distinct Receptor Complexes," J. Biol. Chem. 277, 47517-47523, 2002.
Paul, Fundamental Immunology, 3rd Edition, pp. 292-295.
Payne, G. "Progress in immunoconjugate cancer therapeutics," (2003) Cancer Cell 3:207-212.
Pei et al., "Exploration of Pyrrolobenzodiazepine (PBD)-Dimers Containing Disulfide-Based Prodrugs as Payloads for Antibody-Drug Conjugates." Mol Pharm. Sep. 4, 2018;15(9):3979-3996.
Pepper, C., "Fludarabine-mediated suppression of the excision repair enzyme ERCC1 contributes to the cytotoxic synergy with the DNA minor groove crosslinking agent SJG-136 (Nsc 694501) in chronic lymphocytic leukaemia cells," Br. J. Cancer (2007) 97(2):253-259.
Pepper, C.J. et al., "The novel sequence-specific DNA cross-linking agent SJG-136 (NSC 694501) has potent and selective in vitro cytotoxicity in human B-cell chronic lymphocytic leukemia cells with evidence of a p53-independent mechanism of cell kill," Cancer Res. (2004) 64:6750-6755.
Phillips et al., "Targeting HER2-Positive Breast Cancer with Trastuzumab-DM1, an Antibody-Cytotoxic Drug Conjugate," (2008) Cancer Res. 68(22):9280-9290.
Pingault V., et al., "SOX10 mutations in chronic intestinal pseudo-obstruction suggest a complex physiopathological mechanism," (2002) Hum. Genet. 111, 198-206.
Pletnev S., et al., "Characterization of the Recombinant Extracellular Domains of Human Interleukin-20 Receptors and Their Complexe with Interleukin-19 and Interleukin-20," (2003) Biochemistry 42:12617-12624.
Porkaa et al., "Cloning and Characterization of a Novel Six-Transmembrane Protein STEAP2, Expressed in Normal and Malignant Prostate," Lab. Invest. 82 (11):1573-1582 (2002).
Prasad et al., "Human LAT1, a Subunit of System L Amino Acid Transporter: Molecular Cloning and Transport Function," Biochem. Biophys. Res. Commun. 255 (2), 283-288 (1999).
Preud'Homme et al., "Structure and expression of the mb-1 transcript in human lymphoid cells," (1992) Clin. Exp. Immunol. 90(1):141-146.
Puffenberger E.G., et al., "A Missense Mutation of the Endothelin-B Receptor Gene in Multigenic Hirschsprung's Disease," Cell 79, 1257-1266, 1994.
Purser, et al., "Fluorine in Medicinal Chemistry." Chem. Soc. Rev., 2008, 37, 320-330.
Puzanov, I., "Phase I and pharmacokinetic trial of SJG-136 administered on a daily x5 schedule," EJC Supplements (Nov. 2006) 4(12):93.
Quintas-Cardama, A., "Sequencing of subcloned PCR products facilitates earlier detetction of BCR-ABL1 and other mutants compared to direct sequencing of the ABL1 kinase domain," Leukemia (2008) 22(4):877-878.
Rahman et al. "Antistaphylococcal activity of DNA-interactive pyrrolobenzodiazepine (PBD) dimers and PBD-biaryl conjugates." J Antimicrob Chemother. Jul. 2012; 67(7):1683-96.

(56) References Cited

OTHER PUBLICATIONS

Rahman, K.M., "Effect of microwave irradiation on covalent ligand-DNA interactions," Chem. Commun. (Cambridge, UK), Apr. 2009, 20:2875-2877.
Rahman, K.M., "Rules of DNA adduct formation for pyrrolobenzodiazepine (PBD) dimers," Proceedings of the American Association for Cancer Research Annual Meeting (Apr. 2010) 51:851.
Rahman, K.M., "The pyrrolobenzodiazepine dimer SJG-136 forms sequence-dependent intrastrand DNA cross-lins and monoalkylated adducts in addition to interstrand cross-links," J. Am. Chem. Soc., Sep. 2009, 131(38):13756-13766.
Rao et al., "Influence of diet on mammary cancer in transgenic mice bearing an oncogene expressed in mammary tissue," (1997) Breast Cancer Res. and Treatment 45:149-158.
Reid, J.M., "LC-MS/MS assay and rat pharmacokinetics and metabolism of the dimeric pyrrolobenzodiazepine SJG-136," Proceedings of the American Association for Cancer Research Annual Meeting (Mar. 2004) 45:1248.
Reiter R.E., et al., "Prostate stem cell antigen: A cell surface marker overexpressed in prostate cancer," Proc. Natl. Acad. Sci. U.S.A. 95, 1735-1740, 1998.
Remmers et al., "Conformations of complexes between pyrrolo[1,4]benzodiazepines and DNA segments," J Med Chem. Dec. 1986;29(12):2492-2503.
Rich, I.N., "Validation and development of a predictive paradigm for hemotoxicology using a multifunctional bioluminescence colony-forming proliferation assay," Toxicological Sci. (2005) 87(2):427-441.
Rodrigues et al., "Synthesis and beta-lactamase-mediated activation of a cephalosporin-taxol prodrug," (1995) Chemistry Biology 2:223-227.
Roguska et al., "A comparison of two murine monoclonal antibodies humanized by CDR-grafting and variable domain resurfacing," Protein Eng, 1996, 9(10):895-904.
Roguska et al., "Humanization of murine monoclonal antibodies through variable domain resurfacing," PNAS, 1994, 91(3):969-973.
Ross et al., "Prostate Stem Cell Antigen as Therapy Target: Tissue Expression and in Vivo Efficacy of an Immunoconjugate," (2002) Cancer Res. 62:2546-2553.
Rudikoff et al., Single amino acid substitution altering antigen-binding specificity. Proc Natl Acad Sci U S A. Mar. 1982; 79(6):1979-83.
Sagnou, M.J. et al., "Design and Synthesis of Novel Pyrrolobenzodiazepine (PDB) Prodrugs for ADEPT and GDEPT," Bioorganic & Medicinal Chemistry Letters, 10, 2083-2086 (2000).
Sakaguchi et al., "8 lymphocyte lineage-restricted expression of mb-1, a gene with CD3-like structural properties," (1988) EMBO J. 7(11):3457-3464.
Sakamoto A, Yanagisawa M., et al., "Cloning and Functional Expression of Human cDNA For the ETB Endothelin Receptor," Biochem. Biophys. Res. Commun. 178, 656-663, 1991.
Sanderson et al., "In vivo Drug-Linker Stability of an Anti-CD30 Dipeptide-Linked Auristatin Immunoconjugate," (2005) Clin. Cancer Res. 11:843-852.
Scholler et al., "Soluble member(s) of the mesothelin/ megakaryocyte potentiating factor family are detectable in sera from patients with ovarian carcinoma," Proc. Natl. Acad. Sci. USA vol. 96, pp. 11531-11536, Sep. 1999.
Schroder and Lubke, The Peptides, vol. 1. pp 76-136 (1965) Academic Press.
Schweikart, K., "In vitro myelosuppression of SJG-136, a pyrrolobenzodiazepine dimer: comparison to bizelesin," Proceedings of the American Association for Cancer Research Annual Meeting (Mar. 2004) 45:486.
Segawa et al., "Growth-related Renal Type II Na/Pi Cotransporter," The Journal of Biolocjcal Chemistry, vol. 277. No. 22, Issue of May 31, pp. 19665-19672, 2002.
Semba K., et al., "A v-erbB-related protooncogene, c-erbB-2, is distinct from the c-erbB-1 /epidermal growth factor-receptor gene and is amplified in a human salivary gland adenocarcinoma," 15 Proc. Natl. Acad. Sci. U.S.A 82, 6497-6501, 1985.
Servenius et al., "Class II Genes of the Human Major Histocompatibility Complex, the DOBeta Gene is a Divergent Member of the Class II P Gene Family," (1987) J. Biol. Chem. 262:8759-8766.
Shamis et al., "Bioactivation of Self-Immolative Dendritic Prodrugs by Catalytic Antibody 38C2," (2004) J. Am. Chem. Soc. 126:1726-1731.
Sharkey et al., "Epratuzumab-SN-38: a new antibody-drug conjugate for the therapy of hematologic malignancies," Mol. Cancer Ther. (2012) 11(1):224-234.
Sheikh F., et al., "Cutting Edge: IL-26 Signals through a Novel Receptor Complex Composed of IL-20 Receptor 1 and IL-10 Receptor 21," (2004) J.Immunol, 172, 2006-2010.
Shen et al., "Conjugation site modulates the in vivo stability and therapeutic activity of antibody-drug conjugates," (2012) Nature Biotech., 30(2):184-191.
Shimizu, K et al., "Prothracarcin, a Novel Antitumor Antibiotic," J. Antibiotics, 35, 972-978 (1982).
Sinha S.K., et al., "Characterization of the EBV /C3d Receptor on the Human Jurkat T Cell Line: Evidence for a Novel Transcript," (1993) J. Immunol. 150, 5311-5320.
Smellie, M. et al., "Cellular pharmacology of novel C8-linked anthramycin-based sequence-selective DNA minor groove cross-linking agents," Br. J. Cancer (1994) 70:48-53.
Smellie, M. et al., "Sequence selective recognition of duplex DNA through covalent interstrand cross-linking," Biochem. (2003) 42:8232-8239.
Smith, P. K. et al., "Measurement of protein using bicinchoninic acid." Anal Biochem. Oct. 1985; 150(1):76-85.
Souillac, P. et al., "Characterization of delivery systems, differential scanning calorimetry," Encyclopedia of Controlled Drug Delivery (1999) 212-227 (pp. 217-218).
Storm et al., "Effect of Small Changes in Orientation on Reaction Rate," (1972) J. Amer. Chem. Soc. 94:5815-5825.
Strausberg et al., "Generation and initial analysis of more than 15,000 full-length human and mouse eDNA sequences," (2002) Proc. Natl. Acad. Sci USA 99:16899-16903.
Suggitt, M., "The hollow fibre model—facilitating anti-cancer pre-clinical pharmacodynamics and improving animal welfare," Int. J. Oncol. (2006) 29(6):1493-1499.
Suggs, J.W. et al., "Synthesis and structure of anthramycin analogs via hydride reduction of dilactams," Tetrahedron Letters, 26, No. 40, 4871-4874 (1985).
Sun et al., "Enabling ScFvs as Multi-Drug Carriers: A Dendritic Approach," (2003) Bioorganic & Medicinal Chemistry 11:1761-1768.
Sun et al., "Syntheses of Dendritic Linkers Containing Chlorambucil Residues for the Preparation of Antibody-Multidrug Immunoconjugates," (2002) Bioorganic & Medicinal Chemistry Letters 12:2213-2215.
Sutherland et al., "SGN-CD33A: a novel CD33-targeting antibody-drug conjugate using a pyrrolobenzodiazepine dimer is active in models of drug-resistant AML." Blood 2013, 122:1455-1463.
Sutherland, M.S.K. et al., "SGN-CD33A: a novel CD33-directed antibody-drug conjugate, utilizing pyrrolobenzodiazepine dimers, demonstrates preclinical anti-tumor activity against multi-drug resistant human AML," American Society of Hematology (Dec. 8-12, 2012) Atlanta, Georgia, Abstract No. 3589.
Svensson P.J., et al., "Phenotypic variation in a family with mutations in two Hirschsprung-related genes (RET and endothelin receptor B)," Hum. Genet. 103, 145-148, 1998.
Swiercz J.M., et al., "Plexin-81 /RhoGEF-mediated Rho A activation involves the receptor tyrosine kinase ErbB-2," J. Cell Biol. 165, 869-880, 2004.
Syrigos and Epenetos, "Antibody Directed Enzyme Prodrug Therapy (ADEPT): A Review of the Experimental and Clinical Considerations," (1999) Anticancer Research 19:605-614.
Takeuchi, T. et al., "Neothramycins A and B, New Antitumor Antibiotics," J. Antibiotics, 29, 93-96 (1976).
Talpur et al., "CD25 Expression is Correlated with Histological Grade and Response to Denileukin Diftitox in Cutaneous T-Cell Lymphoma," J. Investigative Dermatology, 2006, 126: 575-583.

(56) References Cited

OTHER PUBLICATIONS

Tawaragi Y., et al., "Primary Structure of Nonspecific Crossreacting Antigen (NCA), a Member of Carcinoembryonic Antigen (CEA) Gene Family, Deduced From cDNA Sequence," Biochem. Biophys. Res. Commun. 150, 89-96, 1988.
Tercel, M. et al., "Unsymmetrical DNA cross-linking agents: combination of the CBI and PBD pharmacophores," J. Med. Chem. (2003) 46:2132-2151.
Thompson J.S., et al., "BAFF-R, a Newly Identified TNF Receptor That Specifically Interacts with BAFF," Science 293 (5537), 2108-2111 (2001).
Thurston, D. E., "Advances in the study of Pyrrolo[2,1-c][1,4] benzodiazepine (PBD) Antitumour Antibiotics", Molecular Aspects of Anticancer Drug-DNA Interaction, Neidle, S. and Waring, M.J., Eds.; Macmillan Press Ltd, 1:54-88 (1993).
Thurston, D.E. and Bose, D.S., "Synthesis of DNA-Interactive Pyrrolo[2,1-c][1,4]benzodiazepines," Chem. Rev., 94:433-465 (1994).
Thurston, D.E. and Thompson, A.S., "The molecular recognition of DNA," Chem. Brit., 26, 767-772 (1990).
Thurston, D.E. et al., "Effect of A-ring modifications on the DNA-binding behavior and cytotoxicity of pyrrolo[2,1-c][1,4]benzodiazepines", Journal of Medicinal Chemistry, 42:1951-1964 (1999).
Thurston, D.E. et al., "Synthesis of Sequence-selective C8-linked Pyrrolo [2,1-c][1,4] Benzodiazepine DNA Interstrand Cross-linking Agent," J. Org. Chem., 61:8141-8147 (1996).
Thurston, D.E. et al., "Synthesis of a novel GC-specific covalent-binding DNA affinity-cleavage agent based on pyrrolobenzodiazepines (PBDs)," Chemical Communications, 563-565 (1996).
Thurston, D.E., "Nucleic acid targeting: therapeutic strategies for the 21st century," Brit. J. Cancer (1999) 80(1):65-85.
Tiberghien et al., "Design and Synthesis of Tesirine, a Clinical Antibody-Drug Conjugate Pyrrolobenzodiazepine Dimer Payload." ACS Med Chem Lett. Nov. 10, 2016; 7(11): 983-987.
Tiberghien, A.C. et al., "Application of the stille coupling reaction to the synthesis of C2-substituted endo-exo unsaturated pyrrolo[2,1-c][1,4]benzodiazepines (PBDs)," Biorg. Med. Chem. Lett. (2004) 14:5041-5044.
Tiberghien, A.C., "Application of the stille coupling reaction to the synthesis of C2-substituted endo-exo unsaturated pyrrolo[2,1-c][1,4]benzodiazepines (PBDs)," Bioorg. Med. Chem. Lett. (2008) 18(6):2073-2077.
Toki et al., "Protease-Mediated Fragmentation of p-Amidobenzyl Ethers: A New Strategy for the Activation of Anticancer Prodrugs," (2002) J. Org. Chem. 67:1866-1872.
Tonnelle et al., "DO Beta a new chain gene in HLA-D with a distinct regulation of expression," (1985) EMBO J. 4(11):2839-2847.
Touchman et al., "The Genomic Region Encompassing the Nephropathic Cystinosis Gene (CTNS): Complete Sequencing of a 200-kb Segment and Discovery of a Novel Gene within the Common Cystinosis-Causing Deletion," (2000) Genome Res. 10:165-173.
Tozuka et al., "Studies on tomaymycin. II. Total synthesis of the antitumor antibiotics, E-and Z-tomaymycins," J. Antibiotics (Tokyo) (1983) 36:276-282.
Trail et al., "Monoclonal antibody drug immunoconjugates for targeted treatment of cancer," (2003) Cancer Immunol. Immunother. 52:328-337.
Tsunakawa, M. et al., "Porothramycin, a new antibiotic of the anthramycin group: Production, isolation, structure and biological activity," J. Antibiotics, 41:1366-1373 (1988).
Tsutsumi M., et al., "Novel endothelin B receptor transcripts with the potential of generating a new receptor," Gene 228, 43-49, 1999.
Uchida et al., "A Novel Epidermal Growth Factor-like Molecule Containing Two Follistatin Modules Stimulates Tyrosine Phosphorylation of erbB-4 in MKN28 Gastric Cancer Cells," (1999) Biochem. Biophys. Res. Commun. 266:593-602.
Umezawa, H. et al., "Mazethramycins," SciFinder Scholar, 2-3 (2002).
Umezawa, H. et al., Chemical Abstract No. 4427a, "Mazethramycins" Chemical Abstracts, vol. 90, No. 1, 428 (1979).

U.S. Appl. No. 62/547,303, filed Aug. 18, 2017.
Valeur et al., "Amid bond formation: beyond the myth of coupling reagents." Chem. Soc. Rev. 2009, 38:606-631.
Van Geel et al., "Chemoenzymatic Conjugation of Toxic Payloads to the Globally Conserved N-Glycan of Native mAbs Provides Homogeneous and Highly Efficacious Antibody-Drug Conjugates," (2015) Bioconjugate Chem. 26: 2233-2242.
Verheij J.B., et al., "ABCD Syndrome is Caused by a Homozygous Mutation in the EDNRB Gene," Am. J. Med. 15 Genet. 108, 223-225, 2002.
Vippagunta, S.R. et al., "Crystalline solids," Adv. Drug Delivery Rev. (2001) 48:3-26.
Von Hoegen et al., "Identification of a human protein homologous to the mouse Lyb-2 B cell differentiation antigen and sequence of the corresponding cDNA," (1990) J. Immunol. 144(12):4870-4877.
Wakankar, et al., "Physicochemical stability of the antibody-drug conjugate Trastuzumab-DM1: changes due to modification and conjugation processes." Bioconjugate Chemistry, 2010, 21, 1588-1595.
Walton et al., "Preclinical pharmacology and antitumour activity of the novel sequence-selective DNA minor-groove cross-linking agent DSB-120." Cancer Chemother Pharmacol. 1996; 38(5):431-8.
Wang, J.H., "Determination of antitumor agent AJG-136 in human serum by HPLC with tandem mass spectrometric detection (HPLC-MS/MS)," Abstracts of Papers American Chemical Society (Mar. 13, 2005) 229(1):U119.
Webster et al., "Mammary tumorigenesis and metastasis in transgenic mice," (1994) Semin. Cancer Biol. 5:69-76.
Weidner-Wells, M.A. et al., "Photochemical approach to the synthesis of the pyrrolo[1,4]benzodiazepine antibiotics," J. Org. Chem. (1989) 54:5746-5758.
Weis J.J., et al., "Identification of a partial eDNA clone for the C3d/Epstein-Barr virus receptor of human B lymphocytes: Homology with the receptor for fragments C3b and C4b of the third and fourth components of complement," Proc. Natl. Acad. Sci. U.S.A. 83, 5639-5643, 1986.
Weis J.J., et al., "Structure of the human b lymphocyte receptor for c3d and the epstein-barr virus and relatedness to other members of the family of C3/C4 binding proteins," J. Exp. Med. 167, 1047-1066, 1988.
Wells, G. et al., "Design, synthesis and biophysical and biological evaluation of a series of pyrrolobenzodiazepine-poly(N-methylpyrrole) conjugates," J. Med. Chem. (2006) 49:5442-5461.
Wikipedia, "How many types of cancer are there?", 2012, 3 pages; http://wiki.answers.com/Q/How-many-different-types_of_cancer_are_there.
Wikipedia, "Management of Cancer," 2012, 1 page; http://en.wikipedia.org/wiki/Management of cancer.
Wilkinson "Eph Receptors and Ephrins: Regulators of Guidance and Assembly," Int. Rev. Cytol. 196:177-244 (2000).
Wilkinson, G.P., "Pharmacokinetics and intracellular pharmacological characteristics of the novel pyrrolobenzodiazepine (PBD) dimer SJG-136," Proceedings of the American Association for Cancer Research Annual Meeting (Jul. 2003) 44:320.
Wilkinson, G.P., "Pharmacokinetics, metabolism and glutathione reactivity of SJG-136," Br. J. Cancer (2003) 88(Supp. 1):S29.
Wilkinson, G.P., "Preliminary pharmacokinetic and bioanalytical studies of SJG-136 (NSC 694501), a sequence-selective pyrrolobenzodiazepine dimer DNA-cross-linking agent," Investigational New Drugs (2004) 22(3):231-240.
Wilson et al., "eDNA Cloning of the B Cell Membrane Protein CD22: A Mediator of B-B Cell Interactions," (1991) J. Exp. Med. 173:137-146.
Wilson, S.C. et al., "Design and Synthesis of a Novel Epoxide-Containing Pyrrolo[2,1-c][1,4]benzodiazepine (PBD) via a New Cyclization Procedure," Tetrahedron Letters, 36, No. 35, 6333-6336 (1995).
Wilson, S.C. et al., "Design, Synthesis, and Evaluation of a Novel Sequence—Selective Epoxide-Containing DNA Cross-Linking Agent Based on the Pyrrolo[2,1- c][1,4]benzodiazepine System", J. Med. Chem. 42: 4028-4041 (1999).
Wolff, M.E., Burger's Medicinal Chemistry, 4th Edition, Part I, Wiley: New York (1979) 336-337.

(56) References Cited

OTHER PUBLICATIONS

Wolff, M.E., Burger's Medicinal Chemistry, 5th Edition, Part I, John Wiley & Sons (1995) 975-977.
Workman, P. et al., "United Kingdom Co-ordinating Committee on Cancer Research (UKCCCR) guidelines for the welfare of animals in experimental neoplasia (second edition)," Br. J. Cancer (1998) 77(1):1-10.
Wu et al., "Arming antibodies: prospects and challenges for immunoconjugates," (2005) Nature Biotech. 23(9):1137-1145.
Wuts, P & Greene, T, Greene's Protective Groups in Organic Synthesis, Fourth Edition (Wiley-Interscience), 2007.
Xie et al., "In vivo behaviour of antibody-drug conjugates for the targeted treatment of cancer," (2006) Expert. Opin Biol. Ther. 6(3):281-291.
Xie, G et al., "Bisindolylmaleimides linked to DNA minor groove binding lexitropsins: synthesis, inhibitory activity against topoisomeraseI, and biological evaluation," J. Med. Chem. (1996) 39:1049-1055.
Xu et al., "Molecular Cloning, Functional Characterization, Tissue Distribution, and Chromosomal Localization of a Human, Small Intestinal Sodium-Phosphate (Na + −Pi) Transporter (SLC34A2)," Genomics 62 (2):281-284 (1999).
Xu, M.J., et al., "Molecular Cloning and Characterization of SPAP1, an Inhibitory Receptor," (2001) Biochem. Biophys. Res. Commun. 280 (3):768-775.
Xu, X.Z., et al., "Regulation of melastatin, a TRP-related protein, through interaction with a cytoplasmic isoform," Proc. Natl. Acad. Sci. U.S.A. 98 (19):10692-10697 (2001).
Yamaguchi, N., et al., "A Novel Cytokine Exhibiting Megakaryocyte Potentiating Activity From a Human Pancreatic Tumor Cell Line HPC-Y5," Biol. Chem. 269 (2), 805-808 (1994).

Yamamoto T., et al., "Similarity of protein encoded by the human c-erb-B-2 gene to epidermal growth factor receptor," Nature 319, 230-234, 1986.
Yang et al., "Murine Six-Transmembrane Epithelial Antigen of the Prostate, Prostate Stem Cell Antigen, and Prostate-specific Membrane Antigen: Prostate-specific Cell-Surface Antigens Highly Expressed in Prostate Cancer of Transgenic Adenocarcinoma Mouse Prostate Mice," Cancer Research, 61, 5857-5860. Aug. 1, 2001.
Yin & Lloyd, "Molecular Cloning of the CA125 Ovarian Cancer Antigen," J. Biol. Chem. 276 (29):27371-27375 (2001).
Younes et al., "Phase I multidose-escalation study of the anti-CD19 maytansinoid immunoconjugate SAR3419 administered by intravenous infusion every 3 weeks to patients with relapsed/refractory B-cell lymphoma," J Clin Oncol., 2012, 30(22):2776- 82.
Yu et al., "Human mb-1 gene: complete edna sequence and its expression in b cells bearing membrane Ig of various isotypes," (1992) J. Immunol. 148(2) 633-637.
Zammarchi et al., "Pre-Clinical Development of Adct-402, a Novel Pyrrolobenzodiazepine (PBD)—Based Antibody Drug Conjugate (ADC) Targeting CD19-Expressing B-Cell Malignancies," Blood, 2015, 126:1564, Abstract.
Zammarchi et al., Abstract 51: Characterization of the mechanism of action, pharmacodynamics and preclinical safety of ADCT-402, a pyrrolobenzodiazepine (PBD) dimer-containing antibody-drug conjugate (ADC) targeting CD19-expressing hematological malignancies, Proceedings: American Association for Cancer Research, Apr. 2017; Washington DC.
Zammarchi et al., Abstract 52: Mechanistic and benchmarking studies of ADCT-502, a pyrrolobenzodiazepine (PBD) dimer-containing antibody-drug conjugate (ADC) targeting HER2-expressing solid tumors, Proceedings: American Association for Cancer Research, Apr. 2017; Washington DC.
Zhao et al., "Novel Antibody Therapeutics Targeting Mesothelin in Solid Tumors," (2016) Clin. Cancer Drugs 3: 76-86.

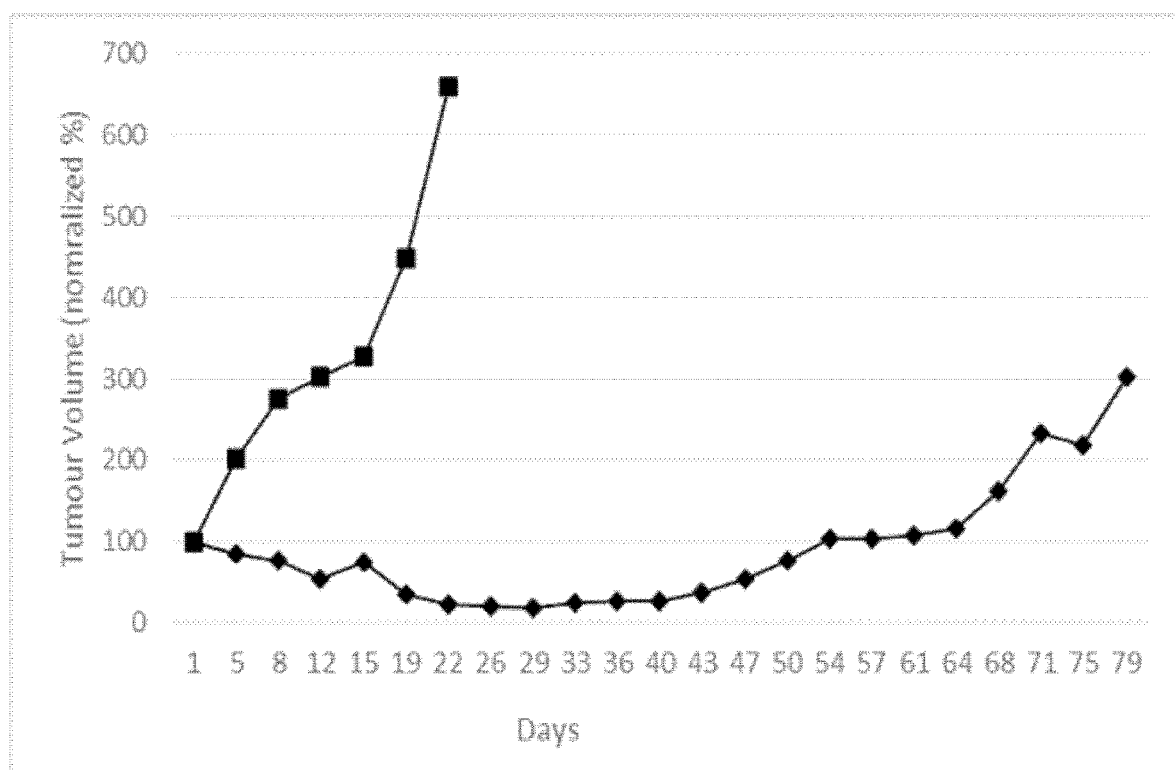

AZETIDOBENZODIAZEPINE DIMERS AND CONJUGATES COMPRISING THEM FOR USE IN THE TREATMENT OF CANCER

The present invention relates to azetidobenzodiazepine (ABD) dimers, conjugates comprising said dimers and the precursor drug linkers used to make such conjugates.

BACKGROUND TO THE INVENTION

Pyrrolobenzodiazepine (PBD) dimers have been shown to be cytotoxic compounds.

For example, SG2000 (SJG-136):

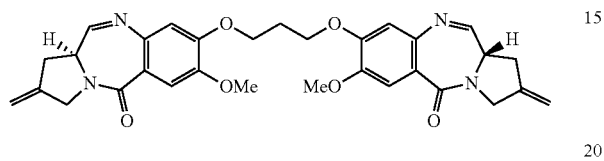

(Gregson, S. J., et al., Chem. Commun., 1999, 797-798. doi: 10.1039/A809791G; Gregson, S., et al., *J. Med. Chem.*, 44, 737-748 (2001); Alley, M. C., et al., *Cancer Research*, 64, 6700-6706 (2004); and Hartley, J. A., et al., *Cancer Research*, 64, 6693-6699 (2004)) has been involved in clinical trials as a standalone agent, for example, NCT02034227 investigating its use in treating Acute Myeloid Leukemia and Chronic Lymphocytic Leukemia (see: https://www.clinicaltrials.gov/ct2/show/NCT02034227).

Dimeric PBD compounds bearing C2 aryl substituents alongside endo-unsaturation, such as SG2202 (ZC-207), are disclosed in WO 2005/085251:

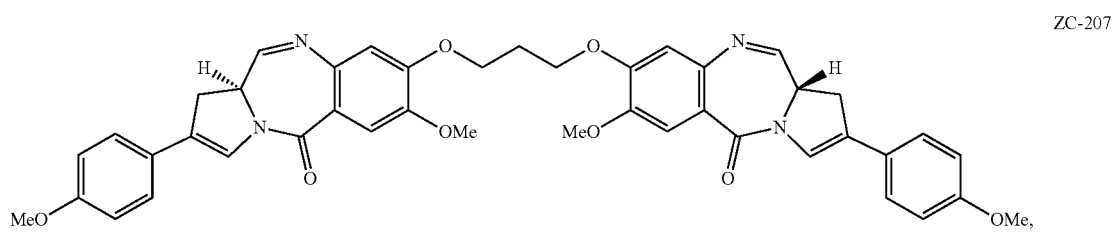 [SMILES: COc1ccc(C2=CN3C(=O)c4cc(OC)c(OCCCOc5cc6c(cc5OC)C(=O)N5C=C(c7ccc(OC)cc7)C[C@H]5C=N6)cc4N=C[C@@H]3C2)cc1]

ZC-207 and in WO2006/111759, bisulphites of such PBD compounds, for example SG2285 (ZC-423):

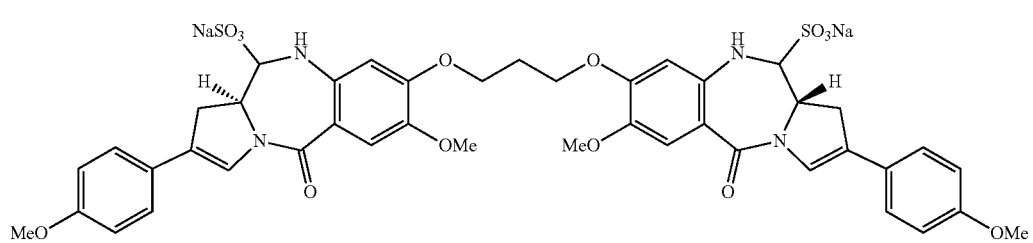

ZC-423

These compounds have been shown to be highly useful cytotoxic agents (Howard, P. W., et al., *Bioorg. Med. Chem.* (2009), doi: 10.1016/j.bmcl.2009.09.012).

Dimer PBD compounds having linker groups for connection to a cell binding agent, such as an antibody, are described in WO 2011/130598. The linker in these compounds is attached to one of the available N10 positions, and are generally cleaved by action of an enzyme on the linker group. WO 2014/057074 and WO 2015/052322 describe specific PBD dimer conjugates bound via the N10 position on one monomer.

At a relatively early stage in the development of PBDs as molecules of interest, it was reported in 1997 (Bose, D. S., et al., Tetrahedron Letters, 38(33), 5839-5842, 1997; doi: 10.1016/S0040-4039(97)01297-5) that the following compound:

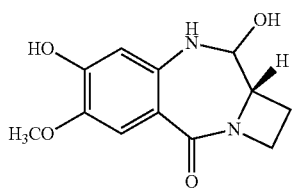 [SMILES: COc1cc2c(cc1O)NC(O)[C@@H]1CCN1C2=O]

had been synthesised and would be evaluated as a potential DNA-binding ligand and cytotoxic agents. No further publication about this compound was made, so it appears that they were either not stable for testing or not active.

DISCLOSURE OF THE INVENTION

A first aspect of the present invention provides a compound of formula IV:

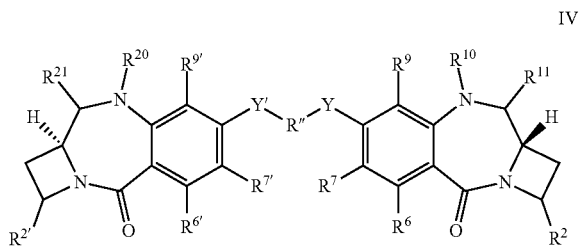

IV and salts and solvates thereof, wherein:
$R^2$ and $R^{2'}$ are H;
$R^6$ and $R^9$ are independently selected from H, R, OH, OR, SH, SR, $NH_2$, NHR, NRR', nitro, $Me_3Sn$ and halo;
where R and R' are independently selected from optionally substituted $C_{1-12}$ alkyl, $C_{3-20}$ heterocyclyl and $C_{5-20}$ aryl groups; either
(a) $R^7$ is selected from H, R, OH, OR, SH, SR, $NH_2$, NHR, NRR', nitro, $Me_3Sn$ and halo;
$R^{7'}$ is selected from H, R, OH, OR, SH, SR, $NH_2$, NHR, NRR', nitro, $Me_3Sn$ and halo; or
(b) $R^7$ and $R^{7'}$ together form a group which is: (i) $-O-(CH_2)_n-O-$, where n is from 7 to 16; or
(ii) $-O-(CH_2CH_2O)_m-$, where m is 2 to 5;
R" is a $C_{3-12}$ alkylene group, which chain may be interrupted by one or more heteroatoms, e.g. O, S, $NR^{N2}$ (where $R^{N2}$ is H or $C_{1-4}$ alkyl), and/or aromatic rings, e.g. benzene or pyridine;

Y and Y' are selected from O, S, or NH;
$R^{6'}$ and $R^{9'}$ are selected from the same groups as $R^6$ and $R^9$ respectively;
either
(i-a) $R^{10}$ and $R^{11}$ together form a double bond between the N and C atoms to which they are bound; or
(i-b) $R^{10}$ is H and $R^{11}$ is selected from OH and $OR^A$, where $R^A$ is $C_{1-4}$ alkyl; or
(i-c) $R^{10}$ and $R^{11}$ are both H;
either
(ii-a) $R^{20}$ and $R^{21}$ together form a double bond between the N and C atoms to which they are bound; or
(ii-b) $R^{20}$ is H and $R^{21}$ is selected from OH and $OR^B$, where $R^B$ is $C_{1-4}$ alkyl; or
(ii-c) $R^{20}$ and $R^{21}$ are both H.

A second aspect of the present invention comprises a compound with the formula I:

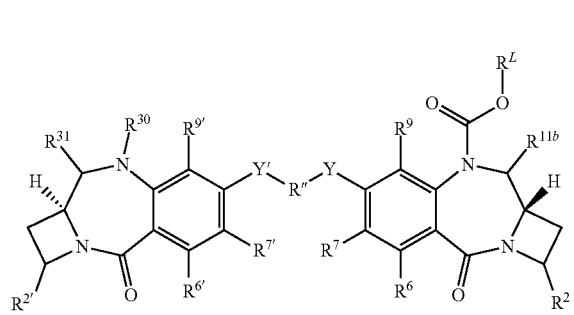

I and salts and solvates thereof, wherein:
Y, Y', R", $R^2$, $R^{2'}$, $R^6$, $R^{6'}$, $R^7$, $R^{7'}$, $R^9$ and $R^{9'}$ are as defined in the first aspect of the invention;
$R^{11b}$ is selected from OH, $OR^A$, where $R^A$ is $C_{1-4}$ alkyl; and
$R^L$ is a linker for connection to a cell binding agent, which is selected from:
(iiia):

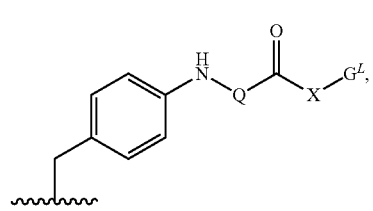

IIIa wherein
Q is:

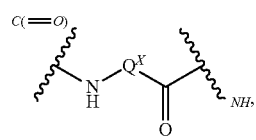

where $Q^X$ is such that Q is an amino-acid residue, a dipeptide residue or a tripeptide residue X is:

[Structure 5: C(=O)-[CH2]a-[O-CH2CH2]b-[NH-C(=O)]c-[CH2]d-G^L]

where a=0 to 5, b=0 to 16, c=0 or 1, d=0 to 5;
$G^L$ is a linker for connecting to a Ligand Unit; and (iiib):

[Structure IIIb: R^L1, R^L2 groups with disulfide-pyridyl-NO2]

where $R^{L1}$ and $R^{L2}$ are independently selected from H and methyl, or together with the carbon atom to which they are bound form a cyclopropylene or cyclobutylene group;

and e is 0 or 1;

either:
 (a) $R^{30}$ and $R^{31}$ together form a double bond between the N and C atoms to which they are bound; or
 (b) $R^{30}$ is H and $R^{31}$ is selected from OH and $OR^B$, where $R^B$ is $C_{1-4}$ alkyl;
 (c) $R^{30}$ and $R^{31}$ are both H; or
 (d) $R^{31}$ is OH or $OR^B$, where $R^B$ is $C_{1-4}$ alkyl and $R^{30}$ is selected from:

(i) [Ph-SO2-CH2CH2-O-C(=O)-*]

(ii) [Me-O-C(=O)-O-*]

(iii) [benzyl with R^z substituent, -O-C(=O)-*]

where $R^Z$ is selected from:

(z-i) [piperazine carbamate with N-Me]

(z-ii) $OC(=O)CH_3$;
(z-iii) $NO_2$;
(z-iv) OMe;
(z-v) glucoronide;
(z-vi) $NH-C(=O)-X_1-NHC(=O)X_2-NH-C(=O)-R^{ZC}$, where $-C(=O)-X_1-NH-$ and $-C(=O)-X_2-NH-$ represent natural amino acid residues and $R^{ZC}$ is selected from Me, OMe, $CH_2CH_2OMe$, and $(CH_2CH_2O)_2Me$.

A third aspect of the present invention provides Conjugates of formula II:

$$L-(D^L)_p \quad (II)$$

wherein L is a Ligand unit (i.e., a targeting agent), $D^L$ is a Drug Linker unit of formula I':

[Structure I*: PBD dimer with R^31, R^30, R^9', Y', R'', Y, R^9, R^11b, R^LL, R^2', R^6', R^7', R^7, R^6, R^2]

wherein $R^2$, $R^{2'}$, $R^6$, $R^7$, $R^9$, $R^{11b}$, Y, R'', Y', $R^{6'}$, $R^{7'}$, $R^{9'}$, $R^{30}$ and $R^{31}$ are as defined in the second aspect of the invention;

$R^{LL}$ is a linker for connection to a cell binding agent, which is selected from: (iiia):

[Structure IIIa': para-substituted aniline with -NH-Q-O-C(=O)-X-G^LL]

where Q and X are as defined in the first aspect and $G^{LL}$ is a linker connected to a Ligand Unit; and (iiib):

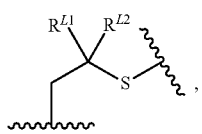

where $R^{L1}$ and $R^{L2}$ are as defined in the first aspect;
wherein p is an integer of from 1 to 20.

The Ligand unit, described more fully below, is a targeting agent that binds to a target moiety. The Ligand unit can, for example, specifically bind to a cell component (a Cell Binding Agent) or to other target molecules of interest. The Ligand unit can be, for example, a protein, polypeptide or peptide, such as an antibody, an antigen-binding fragment of an antibody, or other binding agent, such as an Fc fusion protein.

A fourth aspect of the present invention provides the use of a conjugate of the third aspect of the invention in the manufacture of a medicament for treating a proliferative disease. The fourth aspect also provides a conjugate of the third aspect of the invention for use in the treatment of a proliferative disease. The fourth aspect also provides a method of treating a proliferative disease comprising administering a therapeutically effective amount of a conjugate of the second aspect of the invention to a patient in need thereof.

One of ordinary skill in the art is readily able to determine whether or not a candidate conjugate treats a proliferative condition for any particular cell type. For example, assays which may conveniently be used to assess the activity offered by a particular compound are described in the examples below.

A fifth aspect of the present invention provides the synthesis of a conjugate of the third aspect of the invention comprising conjugating a compound (drug linker) of the second aspect of the invention with a Ligand Unit.

Compounds of formula IV are the warheads released by conjugates of the third aspect.

Definitions

Substituents

The phrase "optionally substituted" as used herein, pertains to a parent group which may be unsubstituted or which may be substituted.

Unless otherwise specified, the term "substituted" as used herein, pertains to a parent group which bears one or more substituents. The term "substituent" is used herein in the conventional sense and refers to a chemical moiety which is covalently attached to, or if appropriate, fused to, a parent group. A wide variety of substituents are well known, and methods for their formation and introduction into a variety of parent groups are also well known.

Examples of substituents are described in more detail below.

$C_{1-12}$ alkyl: The term "$C_{1-12}$ alkyl" as used herein, pertains to a monovalent moiety obtained by removing a hydrogen atom from a carbon atom of a hydrocarbon compound having from 1 to 12 carbon atoms, which may be aliphatic or alicyclic, and which may be saturated or unsaturated (e.g. partially unsaturated, fully unsaturated). The term "$C_{1-4}$ alkyl" as used herein, pertains to a monovalent moiety obtained by removing a hydrogen atom from a carbon atom of a hydrocarbon compound having from 1 to 4 carbon atoms, which may be aliphatic or alicyclic, and which may be saturated or unsaturated (e.g. partially unsaturated, fully unsaturated). Thus, the term "alkyl" includes the sub-classes alkenyl, alkynyl, cycloalkyl, etc., discussed below.

Examples of saturated alkyl groups include, but are not limited to, methyl ($C_1$), ethyl ($C_2$), propyl ($C_3$), butyl ($C_4$), pentyl ($C_5$), hexyl ($C_6$) and heptyl ($C_7$).

Examples of saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$) and n-heptyl ($C_7$).

Examples of saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

$C_{2-12}$ Alkenyl: The term "$C_{2-12}$ alkenyl" as used herein, pertains to an alkyl group having one or more carbon-carbon double bonds.

Examples of unsaturated alkenyl groups include, but are not limited to, ethenyl (vinyl, —CH=CH$_2$), 1-propenyl (—CH=CH—CH$_3$), 2-propenyl (allyl, —CH—CH=CH$_2$), isopropenyl (1-methylvinyl, —C(CH$_3$)=CH$_2$), butenyl ($C_4$), pentenyl ($C_5$), and hexenyl ($C_6$).

$C_{2-12}$ alkynyl: The term "$C_{2-12}$ alkynyl" as used herein, pertains to an alkyl group having one or more carbon-carbon triple bonds.

Examples of unsaturated alkynyl groups include, but are not limited to, ethynyl (—C≡CH) and 2-propynyl (propargyl, —CH$_2$—C≡CH).

$C_{3-12}$ cycloalkyl: The term "$C_{3-12}$ cycloalkyl" as used herein, pertains to an alkyl group which is also a cyclyl group; that is, a monovalent moiety obtained by removing a hydrogen atom from an alicyclic ring atom of a cyclic hydrocarbon (carbocyclic) compound, which moiety has from 3 to 7 carbon atoms, including from 3 to 7 ring atoms.

Examples of cycloalkyl groups include, but are not limited to, those derived from:
Saturated Monocyclic Hydrocarbon Compounds:
cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$) and methylcyclohexane ($C_7$);
Unsaturated Monocyclic Hydrocarbon Compounds:
cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$) and methylcyclohexene ($C_7$); and
Saturated Polycyclic Hydrocarbon Compounds:
norcarane ($C_7$), norpinane ($C_7$), norbornane ($C_7$).

$C_{3-20}$ heterocyclyl: The term "$C_{3-20}$ heterocyclyl" as used herein, pertains to a monovalent moiety obtained by removing a hydrogen atom from a ring atom of a heterocyclic compound, which moiety has from 3 to 20 ring atoms, of which from 1 to 10 are ring heteroatoms. Preferably, each ring has from 3 to 7 ring atoms, of which from 1 to 4 are ring heteroatoms.

In this context, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl", as used herein, pertains to a heterocyclyl group having 5 or 6 ring atoms.

Examples of monocyclic heterocyclyl groups include, but are not limited to, those derived from:
$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

$C_{5-20}$ aryl: The term "$C_{5-20}$ aryl", as used herein, pertains to a monovalent moiety obtained by removing a hydrogen atom from an aromatic ring atom of an aromatic compound, which moiety has from 3 to 20 ring atoms. The term "$C_{5-7}$ aryl", as used herein, pertains to a monovalent moiety obtained by removing a hydrogen atom from an aromatic ring atom of an aromatic compound, which moiety has from 5 to 7 ring atoms and the term "$C_{5-10}$ aryl", as used herein, pertains to a monovalent moiety obtained by removing a hydrogen atom from an aromatic ring atom of an aromatic compound, which moiety has from 5 to 10 ring atoms. Preferably, each ring has from 5 to 7 ring atoms.

In this context, the prefixes (e.g. $C_{3-20}$, $C_{5-7}$, $C_{5-6}$, $C_{5-10}$, etc.) denote the number of ring atoms, or range of number of ring atoms, whether carbon atoms or heteroatoms. For example, the term "$C_{5-6}$ aryl" as used herein, pertains to an aryl group having 5 or 6 ring atoms.

The ring atoms may be all carbon atoms, as in "carboaryl groups".

Examples of carboaryl groups include, but are not limited to, those derived from benzene (i.e. phenyl) ($C_6$), naphthalene ($C_{10}$), azulene ($C_{10}$), anthracene ($C_{1-4}$), phenanthrene ($C_{1-4}$), naphthacene ($C_{18}$), and pyrene ($C_{16}$).

Examples of aryl groups which comprise fused rings, at least one of which is an aromatic ring, include, but are not limited to, groups derived from indane (e.g. 2,3-dihydro-1H-indene) ($C_9$), indene ($C_9$), isoindene ($C_9$), tetraline (1,2,3,4-tetrahydronaphthalene ($C_{10}$), acenaphthene ($C_{12}$), fluorene ($C_{13}$), phenalene ($C_{13}$), acephenanthrene ($C_{15}$), and aceanthrene ($C_{16}$).

Alternatively, the ring atoms may include one or more heteroatoms, as in "heteroaryl groups". Examples of monocyclic heteroaryl groups include, but are not limited to, those derived from:

$N_1$: pyrrole (azole) ($C_5$), pyridine (azine) ($C_6$);

$O_1$: furan (oxole) ($C_5$);

$S_1$: thiophene (thiole) ($C_5$);

$N_1O_1$: oxazole ($C_5$), isoxazole ($C_5$), isoxazine ($C_6$);

$N_2O_1$: oxadiazole (furazan) ($C_5$);

$N_3O_1$: oxatriazole ($C_5$);

$N_1S_1$: thiazole ($C_5$), isothiazole ($C_5$);

$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);

$N_3$: triazole ($C_5$), triazine ($C_6$); and, $N_4$: tetrazole ($C_5$).

Examples of heteroaryl which comprise fused rings, include, but are not limited to:

$C_9$ (with 2 fused rings) derived from benzofuran ($O_1$), isobenzofuran ($O_1$), indole ($N_1$), isoindole ($N_1$), indolizine ($N_1$), indoline ($N_1$), isoindoline ($N_1$), purine ($N_4$) (e.g., adenine, guanine), benzimidazole ($N_2$), indazole ($N_2$), benzoxazole ($N_1O_1$), benzisoxazole ($N_1O_1$), benzodioxole ($O_2$), benzofurazan ($N_2O_1$), benzotriazole ($N_3$), benzothiofuran ($S_1$), benzothiazole ($N_1S_1$), benzothiadiazole ($N_2S$);

$C_{10}$ (with 2 fused rings) derived from chromene ($O_1$), isochromene ($O_1$), chroman ($O_1$), isochroman ($O_1$), benzodioxan ($O_2$), quinoline ($N_1$), isoquinoline ($N_1$), quinolizine ($N_1$), benzoxazine ($N_1O_1$), benzodiazine ($N_2$), pyridopyridine ($N_2$), quinoxaline ($N_2$), quinazoline ($N_2$), cinnoline ($N_2$), phthalazine ($N_2$), naphthyridine ($N_2$), pteridine ($N_4$);

$C_{11}$ (with 2 fused rings) derived from benzodiazepine ($N_2$);

$C_{13}$ (with 3 fused rings) derived from carbazole ($N_1$), dibenzofuran ($O_1$), dibenzothiophene ($S_1$), carboline ($N_2$), perimidine ($N_2$), pyridoindole ($N_2$); and, $C_{14}$ (with 3 fused rings) derived from acridine ($N_1$), xanthene ($O_1$), thioxanthene ($S_1$), oxanthrene ($O_2$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

The above groups, whether alone or part of another substituent, may themselves optionally be substituted with one or more groups selected from themselves and the additional substituents listed below.

Halo: —F, —Cl, —Br, and —I.

Hydroxy: —OH.

Ether: —OR, wherein R is an ether substituent, for example, a $C_{1-7}$ alkyl group (also referred to as a $C_{1-7}$ alkoxy group, discussed below), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$alkyl group.

Alkoxy: —OR, wherein R is an alkyl group, for example, a $C_{1-7}$ alkyl group. Examples of $C_{1-7}$ alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

Acetal: —CH(OR$^1$)(OR$^2$), wherein R$^1$ and R$^2$ are independently acetal substituents, for example, a $C_{1-7}$ alkyl group, a $C_{3-20}$ heterocyclyl group, or a $C_{5-20}$ aryl group, preferably a $C_{1-7}$ alkyl group, or, in the case of a "cyclic" acetal group, R$^1$ and R$^2$, taken together with the two oxygen atoms to which they are attached, and the carbon atoms to which they are attached, form a heterocyclic ring having from 4 to 8 ring atoms. Examples of acetal groups include, but are not limited to, —CH(OMe)$_2$, —CH(OEt)$_2$, and —CH(OMe)(OEt).

Hemiacetal: —CH(OH)(OR$^1$), wherein R$^1$ is a hemiacetal substituent, for example, a C$_{1-7}$ alkyl group, a C$_{3-20}$ heterocyclyl group, or a C$_{5-20}$ aryl group, preferably a C$_{1-7}$ alkyl group. Examples of hemiacetal groups include, but are not limited to, —CH(OH)(OMe) and —CH(OH)(OEt).

Ketal: —CR(OR$^1$)(OR$^2$), where R$^1$ and R$^2$ are as defined for acetals, and R is a ketal substituent other than hydrogen, for example, a C$_{1-7}$ alkyl group, a C$_{3-20}$ heterocyclyl group, or a C$_{5-20}$ aryl group, preferably a C$_{1-7}$ alkyl group. Examples ketal groups include, but are not limited to, —C(Me)(OMe)$_2$, —C(Me)(OEt)$_2$, —C(Me)(OMe)(OEt), —C(Et)(OMe)$_2$, —C(Et)(OEt)$_2$, and —C(Et)(OMe)(OEt).

Hemiketal: —CR(OH)(OR$^1$), where R$^1$ is as defined for hemiacetals, and R is a hemiketal substituent other than hydrogen, for example, a C$_{1-7}$ alkyl group, a C$_{3-20}$ heterocyclyl group, or a C$_{5-20}$ aryl group, preferably a C$_{1-7}$ alkyl group. Examples of hemiacetal groups include, but are not limited to, —C(Me)(OH)(OMe), —C(Et)(OH)(OMe), —C(Me)(OH)(OEt), and —C(Et)(OH)(OEt).

Oxo (keto, -one): =O.

Thione (thioketone): =S.

Imino (imine): =NR, wherein R is an imino substituent, for example, hydrogen, C$_{1-7}$alkyl group, a C$_{3-20}$ heterocyclyl group, or a C$_{5-20}$ aryl group, preferably hydrogen or a C$_{1-7}$ alkyl group. Examples of ester groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a C$_{1-7}$ alkyl group (also referred to as C$_{1-7}$ alkylacyl or C$_{1-7}$ alkanoyl), a C$_{3-20}$ heterocyclyl group (also referred to as C$_{3-20}$ heterocyclylacyl), or a C$_{5-20}$ aryl group (also referred to as C$_{5-20}$ arylacyl), preferably a C$_{1-7}$ alkyl group. Examples of acyl groups include, but are not limited to, —C(=O)CH$_3$ (acetyl), —C(=O)CH$_2$CH$_3$ (propionyl), —C(=O)C(CH$_3$)$_3$ (t-butyryl), and —C(=O)Ph (benzoyl, phenone).

Carboxy (carboxylic acid): —C(=O)OH.

Thiocarboxy (thiocarboxylic acid): —C(=S)SH.

Thiolocarboxy (thiolocarboxylic acid): —C(=O)SH.

Thionocarboxy (thionocarboxylic acid): —C(=S)OH.

Imidic acid: —C(=NH)OH.

Hydroxamic acid: —C(=NOH)OH.

Ester (carboxylate, carboxylic acid ester, oxycarbonyl): —C(=O)OR, wherein R is an ester substituent, for example, a C$_{1-7}$ alkyl group, a C$_{3-20}$ heterocyclyl group, or a C$_{5-20}$ aryl group, preferably a C$_{1-7}$ alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a C$_{1-7}$ alkyl group, a C$_{3-20}$ heterocyclyl group, or a C$_{5-20}$ aryl group, preferably a C$_{1-7}$ alkyl group.

Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Oxycarboyloxy: —OC(=O)OR, wherein R is an ester substituent, for example, a C$_{1-7}$ alkyl group, a C$_{3-20}$ heterocyclyl group, or a C$_{5-20}$ aryl group, preferably a C$_{1-7}$ alkyl group. Examples of ester groups include, but are not limited to, —OC(=O)OCH$_3$, —OC(=O)OCH$_2$CH$_3$, —OC(=O)OC(CH$_3$)$_3$, and —OC(=O)OPh.

Amino: —NR$^1$R$^2$, wherein R$^1$ and R$^2$ are independently amino substituents, for example, hydrogen, a C$_{1-7}$ alkyl group (also referred to as C$_{1-7}$ alkylamino or di-C$_{1-7}$ alkylamino), a C$_{3-20}$ heterocyclyl group, or a C$_{5-20}$ aryl group, preferably H or a C$_{1-7}$ alkyl group, or, in the case of a "cyclic" amino group, R$^1$ and R$^2$, taken together with the nitrogen atom to which they are attached, form a heterocyclic ring having from 4 to 8 ring atoms. Amino groups may be primary (—NH$_2$), secondary (—NHR$^1$), or tertiary (—NHR$^1$R$^2$), and in cationic form, may be quaternary (—$^+$NR$^1$R$^2$R$^3$). Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_3$, —C(=S)N(CH$_3$)$_2$, and —C(=S)NHCH$_2$CH$_3$.

Acylamido (acylamino): —NR$^1$C(=O)R$^2$, wherein R$^1$ is an amide substituent, for example, hydrogen, a C$_{1-7}$ alkyl group, a C$_{3-20}$ heterocyclyl group, or a C$_{5-20}$ aryl group, preferably hydrogen or a C$_{1-7}$ alkyl group, and R$^2$ is an acyl substituent, for example, a C$_{1-7}$ alkyl group, a C$_{3-20}$ heterocyclyl group, or a C$_{5-20}$aryl group, preferably hydrogen or a C$_{1-7}$ alkyl group. Examples of acylamide groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl, and phthalimidyl:

succinimidyl    maleimidyl    phthalimidyl

Aminocarbonyloxy: —OC(=O)NR$^1$R$^2$, wherein R$^1$ and R$^2$ are independently amino substituents, as defined for amino groups. Examples of aminocarbonyloxy groups include, but are not limited to, —OC(=O)NH$_2$, —OC(=O)NHMe, —OC(=O)NMe$_2$, and —OC(=O)NEt$_2$.

Ureido: —N(R$^1$)CONR$^2$R$^3$ wherein R$^2$ and R$^3$ are independently amino substituents, as defined for amino groups, and R$^1$ is a ureido substituent, for example, hydrogen, a C$_{1-7}$ alkyl group, a C$_{3-20}$ heterocyclyl group, or a C$_{5-20}$ aryl group, preferably hydrogen or a C$_{1-7}$ alkyl group. Examples of ureido groups include, but are not limited to, —NHCONH$_2$, —NHCONHMe, —NHCONHEt, —NHCONMe$_2$, —NHCONEt$_2$, —NMeCONH$_2$, —NMeCONHMe, —NMeCONHEt, —NMeCONMe$_2$, and —NMeCONEt$_2$.

Guanidino: —NH—C(=NH)NH$_2$.

Tetrazolyl: a five membered aromatic ring having four nitrogen atoms and one carbon atom,

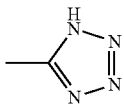

Imino: =NR, wherein R is an imino substituent, for example, for example, hydrogen, a $C_{1-7}$ alkyl group, a $C_{3-20}$ heterocyclyl group, or a $C_{5-20}$ aryl group, preferably H or a $C_{1-7}$ alkyl group. Examples of imino groups include, but are not limited to, =NH, =NMe, and =NEt.

Amidine (amidino): —C(=NR)NR$_2$, wherein each R is an amidine substituent, for example, hydrogen, a $C_{1-7}$ alkyl group, a $C_{3-20}$ heterocyclyl group, or a $C_{5-20}$ aryl group, preferably H or a $C_{1-7}$ alkyl group. Examples of amidine groups include, but are not limited to, —C(=NH)NH$_2$, —C(=NH)NMe$_2$, and —C(=NMe)NMe$_2$.

Nitro: —NO$_2$.
Nitroso: —NO.
Azido: —N$_3$.
Cyano (nitrile, carbonitrile): —CN.
Isocyano: —NC.
Cyanato: —OCN.
Isocyanato: —NCO.
Thiocyano (thiocyanato): —SCN.
Isothiocyano (isothiocyanato): —NCS.
Sulfhydryl (thiol, mercapto): —SH.

Thioether (sulfide): —SR, wherein R is a thioether substituent, for example, a $C_{1-7}$ alkyl group (also referred to as a $C_{1-7}$ alkylthio group), a $C_{3-20}$ heterocyclyl group, or a $C_{5-20}$ aryl group, preferably a $C_{1-7}$ alkyl group. Examples of $C_{1-7}$ alkylthio groups include, but are not limited to, —SCH$_3$ and —SCH$_2$CH$_3$.

Disulfide: —SS—R, wherein R is a disulfide substituent, for example, a $C_{1-7}$ alkyl group, a $C_{3-20}$ heterocyclyl group, or a $C_{5-20}$ aryl group, preferably a $C_{1-7}$ alkyl group (also referred to herein as $C_{1-7}$ alkyl disulfide). Examples of $C_{1-7}$ alkyl disulfide groups include, but are not limited to, —SSCH$_3$ and —SSCH$_2$CH$_3$.

Sulfine (sulfinyl, sulfoxide): —S(=O)R, wherein R is a sulfine substituent, for example, a $C_{1-7}$ alkyl group, a $C_{3-20}$ heterocyclyl group, or a $C_{5-20}$ aryl group, preferably a $C_{1-7}$ alkyl group. Examples of sulfine groups include, but are not limited to, —S(=O)CH$_3$ and —S(=O)CH$_2$CH$_3$.

Sulfone (sulfonyl): —S(=O)$_2$R, wherein R is a sulfone substituent, for example, a $C_{1-7}$ alkyl group, a $C_{3-20}$ heterocyclyl group, or a $C_{5-20}$ aryl group, preferably a $C_{1-7}$ alkyl group, including, for example, a fluorinated or perfluorinated $C_{1-7}$ alkyl group. Examples of sulfone groups include, but are not limited to, —S(=O)$_2$CH$_3$ (methanesulfonyl, mesyl), —S(=O)$_2$CF$_3$ (triflyl), —S(=O)$_2$CH$_2$CH$_3$ (esyl), —S(=O)$_2$C$_4$F$_9$ (nonaflyl), —S(=O)$_2$CH$_2$CF$_3$ (tresyl), —S(=O)$_2$CH$_2$CH$_2$NH$_2$ (tauryl), —S(=O)$_2$Ph (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylamino-naphthalen-1-ylsulfonate (dansyl).

Sulfinic acid (sulfino): —S(=O)OH, —SO$_2$H.
Sulfonic acid (sulfo): —S(=O)$_2$OH, —SO$_3$H.

Sulfinate (sulfinic acid ester): —S(=O)OR; wherein R is a sulfinate substituent, for example, a $C_{1-7}$ alkyl group, a $C_{3-20}$ heterocyclyl group, or a $C_{5-20}$ aryl group, preferably a $C_{1-7}$ alkyl group. Examples of sulfinate groups include, but are not limited to, —S(=O)OCH$_3$ (methoxysulfinyl; methyl sulfinate) and —S(=O)OCH$_2$CH$_3$ (ethoxysulfinyl; ethyl sulfinate).

Sulfonate (sulfonic acid ester): —S(=O)$_2$OR, wherein R is a sulfonate substituent, for example, a $C_{1-7}$ alkyl group, a $C_{3-20}$ heterocyclyl group, or a $C_{5-20}$ aryl group, preferably a $C_{1-7}$ alkyl group. Examples of sulfonate groups include, but are not limited to, —S(=O)$_2$OCH$_3$ (methoxysulfonyl; methyl sulfonate) and —S(=O)$_2$OCH$_2$CH$_3$ (ethoxysulfonyl; ethyl sulfonate).

Sulfinyloxy: —OS(=O)R, wherein R is a sulfinyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfinyloxy groups include, but are not limited to, —OS(=O)CH$_3$ and —OS(=O)CH$_2$CH$_3$.

Sulfonyloxy: —OS(=O)$_2$R, wherein R is a sulfonyloxy substituent, for example, a $C_{1-7}$ alkyl group, a $C_{3-20}$ heterocyclyl group, or a $C_{5-20}$ aryl group, preferably a $C_{1-7}$ alkyl group.

Examples of sulfonyloxy groups include, but are not limited to, —OS(=O)$_2$CH$_3$ (mesylate) and —OS(=O)$_2$CH$_2$CH$_3$ (esylate).

Sulfate: —OS(=O)$_2$OR; wherein R is a sulfate substituent, for example, a $C_{1-7}$ alkyl group, a $C_{3-20}$ heterocyclyl group, or a $C_{5-20}$ aryl group, preferably a $C_{1-7}$ alkyl group. Examples of sulfate groups include, but are not limited to, —OS(=O)$_2$OCH$_3$ and —SO(=O)$_2$OCH$_2$CH$_3$.

Sulfamyl (sulfamoyl; sulfinic acid amide; sulfinamide): —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamido (sulfinamoyl; sulfonic acid amide; sulfonamide): —S(=O)$_2$NR$^1$R$^2$, wherein R$^1$ and R$^2$ are independently amino substituents, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

Sulfamino: —NR$^1$S(=O)$_2$OH, wherein R$^1$ is an amino substituent, as defined for amino groups. Examples of sulfamino groups include, but are not limited to, —NHS(=O)$_2$OH and —N(CH$_3$)S(=O)$_2$OH.

Sulfonamino: —NR$^1$S(=O)$_2$R, wherein R$^1$ is an amino substituent, as defined for amino groups, and R is a sulfonamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfonamino groups include, but are not limited to, —NHS(=O)$_2$CH$_3$ and —N(CH$_3$)S(=O)$_2$C$_6$H$_5$.

Sulfinamino: —NR$^1$S(=O)R, wherein R$^1$ is an amino substituent, as defined for amino groups, and R is a sulfinamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfinamino groups include, but are not limited to, —NHS(=O)CH$_3$ and —N(CH$_3$)S(=O)C$_6$H$_5$.

Phosphino (phosphine): —PR$_2$, wherein R is a phosphino substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphino groups include, but are not limited to, —PH$_2$, —P(CH$_3$)$_2$, —P(CH$_2$CH$_3$)$_2$, —P(t-Bu)$_2$, and —P(Ph)$_2$.

Phospho: —P(=O)$_2$.

Phosphinyl (phosphine oxide): —P(=O)R$_2$, wherein R is a phosphinyl substituent, for example, a $C_{1-7}$ alkyl group, a $C_{3-20}$ heterocyclyl group, or a $C_{5-20}$ aryl group, preferably a $C_{1-7}$ alkyl group or a $C_{5-20}$ aryl group. Examples of phosphinyl groups include, but are not limited to, —P(=O)(CH$_3$)$_2$, —P(=O)(CH$_2$CH$_3$)$_2$, —P(=O)(t-Bu)$_2$, and —P(=O)(Ph)$_2$.

Phosphonic acid (phosphono): —P(=O)(OH)$_2$.

Phosphonate (phosphono ester): —P(=O)(OR)$_2$, where R is a phosphonate substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphonate groups include, but are not limited to, —P(=O)(OCH$_3$)$_2$, —P(=O)(OCH$_2$CH$_3$)$_2$, —P(=O)(O-t-Bu)$_2$, and —P(=O)(OPh)$_2$.

Phosphoric acid (phosphonooxy): —OP(=O)(OH)$_2$.

Phosphate (phosphonooxy ester): —OP(=O)(OR)$_2$, where R is a phosphate substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphate groups include, but are not limited to, —OP(=O)(OCH$_3$)$_2$, —OP(=O)(OCH$_2$CH$_3$)$_2$, —OP(=O)(O-t-Bu)$_2$, and —OP(=O)(OPh)$_2$.

Phosphorous acid: —OP(OH)$_2$.

Phosphite: —OP(OR)$_2$, where R is a phosphite substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphite groups include, but are not limited to, —OP(OCH$_3$)$_2$, —OP(OCH$_2$CH$_3$)$_2$, —OP(O-t-Bu)$_2$, and —OP(OPh)$_2$.

Phosphoramidite: —OP(OR$^1$)—NR$^{22}$, where R$^1$ and R$^2$ are phosphoramidite substituents, for example, —H, a (optionally substituted) C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphoramidite groups include, but are not limited to, —OP(OCH$_2$CH$_3$)—N(CH$_3$)$_2$, —OP(OCH$_2$CH$_3$)—N(i-Pr)$_2$, and —OP(OCH$_2$CH$_2$CN)—N(i-Pr)$_2$.

Phosphoramidate: —OP(=O)(OR$^1$)—NR$^{22}$, where R$^1$ and R$^2$ are phosphoramidate substituents, for example, —H, a (optionally substituted) C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphoramidate groups include, but are not limited to, —OP(=O)(OCH$_2$CH$_3$)—N(CH$_3$)$_2$, —OP(=O)(OCH$_2$CH$_3$)—N(i-Pr)$_2$, and —OP(=O)(OCH$_2$CH$_2$CN)—N(i-Pr)$_2$.

Alkylene

C$_{3-12}$ alkylene: The term "C$_{3-12}$ alkylene", as used herein, pertains to a bidentate moiety obtained by removing two hydrogen atoms, either both from the same carbon atom, or one from each of two different carbon atoms, of a hydrocarbon compound having from 3 to 12 carbon atoms (unless otherwise specified), which may be aliphatic or alicyclic, and which may be saturated, partially unsaturated, or fully unsaturated. Thus, the term "alkylene" includes the subclasses alkenylene, alkynylene, cycloalkylene, etc., discussed below.

Examples of linear saturated C$_{3-12}$ alkylene groups include, but are not limited to, —(CH$_2$)$_n$— where n is an integer from 3 to 12, for example, —CH$_2$CH$_2$CH$_2$— (propylene), —CH$_2$CH$_2$CH$_2$CH$_2$— (butylene), —CH$_2$CH$_2$CH$_2$CH$_2$CH$_2$— (pentylene) and —CH$_2$CH$_2$CH$_2$CH—$_2$CH$_2$CH$_2$CH$_2$— (heptylene).

Examples of branched saturated C$_{3-12}$ alkylene groups include, but are not limited to, —CH(CH$_3$)CH$_2$—, —CH(CH$_3$)CH$_2$CH$_2$—, —CH(CH$_3$)CH$_2$CH$_2$CH$_2$—, —CH$_2$CH(CH$_3$)CH$_2$—, —CH$_2$CH(CH$_3$)CH$_2$CH$_2$—, —CH(CH$_2$CH$_3$)—, —CH(CH$_2$CH$_3$)CH$_2$—, and —CH$_2$CH(CH$_2$CH$_3$)CH$_2$—.

Examples of linear partially unsaturated C$_{3-12}$ alkylene groups (C$_{3-12}$ alkenylene, and alkynylene groups) include, but are not limited to, —CH=CH—CH$_2$—, —CH$_2$—CH=CH$_2$—, —CH=CH—CH$_2$—CH$_2$—, —CH=CH—CH$_2$—CH$_2$—CH$_2$—, —CH=CH—CH=CH—, —CH=CH—CH=CH—CH$_2$—, —CH=CH—CH$_2$—CH=CH—, —CH=CH—CH$_2$—CH$_2$—CH=CH—, —CH=CH—CH$_2$—CH=CH—CH$_2$—, —CH=CH—CH$_2$—CH$_2$—CH=CH—, and —CH$_2$—C≡C—CH$_2$—.

Examples of branched partially unsaturated C$_{3-12}$ alkylene groups (C$_{3-12}$ alkenylene and alkynylene groups) include, but are not limited to, —C(CH$_3$)=CH—, —C(CH$_3$)=CH—CH$_2$—, —CH=CH—CH(CH$_3$)— and —C≡C—CH(CH$_3$)—.

Examples of alicyclic saturated C$_{3-12}$ alkylene groups (C$_{3-12}$ cycloalkylenes) include, but are not limited to, cyclopentylene (e.g. cyclopent-1,3-ylene), and cyclohexylene (e.g. cyclohex-1,4-ylene).

Examples of alicyclic partially unsaturated C$_{3-12}$ alkylene groups (C$_{3-12}$ cycloalkylenes) include, but are not limited to, cyclopentenylene (e.g. 4-cyclopenten-1,3-ylene), cyclohexenylene (e.g. 2-cyclohexen-1,4-ylene; 3-cyclohexen-1,2-ylene; 2,5-cyclohexadien-1,4-ylene).

Where the C$_{3-12}$ alkylene group is interrupted by a heteroatom, the subscript refers to the number of atoms in the chain including the heteroatoms. For example, the chain —C$_2$H$_4$—O—C$_2$H$_4$— would be a C$_5$ group.

Where the C$_{3-12}$ alkylene group is interrupted by an aromatic ring, the subscript refers to the number of atoms directly in the chain including the aromatic ring. For example, the chain

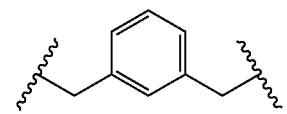 [SMILES: *Cc1cccc(C*)c1]

would be a C$_5$ group.

Connection labels: In the formula

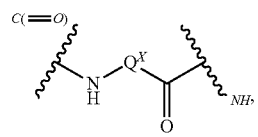

the superscripted labels $^{C(=O)}$ and $^{NH}$ indicate the group to which the atoms are bound. For example, the NH group is shown as being bound to a carbonyl (which is not part of the moiety illustrated), and the carbonyl is shown as being bound to a NH group (which is not part of the moiety illustrated).

Ligand Unit

The Ligand Unit may be of any kind, and include a protein, polypeptide, peptide and a non-peptidic agent that specifically binds to a target molecule. In some embodiments, the Ligand unit may be a protein, polypeptide or peptide. In some embodiments, the Ligand unit may be a cyclic polypeptide. These Ligand units can include antibodies or a fragment of an antibody that contains at least one target molecule-binding site, lymphokines, hormones, growth factors, or any other cell binding molecule or substance that can specifically bind to a target.

The terms "specifically binds" and "specific binding" refer to the binding of an antibody or other protein, polypeptide or peptide to a predetermined molecule (e.g., an antigen). Typically, the antibody or other molecule binds with an affinity of at least about $1 \times 10^7 \, M^{-1}$, and binds to the predetermined molecule with an affinity that is at least two-fold greater than its affinity for binding to a non-specific molecule (e.g., BSA, casein) other than the predetermined molecule or a closely-related molecule.

Examples of Ligand units include those agents described for use in WO 2007/085930, which is incorporated herein.

In some embodiments, the Ligand unit is a Cell Binding Agent that binds to an extracellular target on a cell. Such a Cell Binding Agent can be a protein, polypeptide, peptide or a non-peptidic agent. In some embodiments, the Cell Binding Agent may be a protein, polypeptide or peptide. In some embodiments, the Cell Binding Agent may be a cyclic polypeptide. The Cell Binding Agent also may be antibody or an antigen-binding fragment of an antibody. Thus, in one embodiment, the present invention provides an antibody-drug conjugate (ADC).

Cell Binding Agent

A cell binding agent may be of any kind, and include peptides and non-peptides. These can include antibodies or a fragment of an antibody that contains at least one binding site, lymphokines, hormones, hormone mimetics, vitamins, growth factors, nutrient-transport molecules, or any other cell binding molecule or substance.

Peptides

In one embodiment, the cell binding agent is a linear or cyclic peptide comprising 4-30, preferably 6-20, contiguous amino acid residues. In this embodiment, it is preferred that one cell binding agent is linked to one monomer or dimer azetidobenzodiazepine compound.

In one embodiment the cell binding agent comprises a peptide that binds integrin $\alpha_v\beta_6$. The peptide may be selective for $\alpha_v\beta_6$ over XYS.

In one embodiment the cell binding agent comprises the A20FMDV-Cys polypeptide. The A20FMDV-Cys has the sequence: NAVPNLRGDLQVLAQKVARTC. Alternatively, a variant of the A20FMDV-Cys sequence may be used wherein one, two, three, four, five, six, seven, eight, nine or ten amino acid residues are substituted with another amino acid residue. Furthermore, the polypeptide may have the sequence NAVXXXXXXXXXXXXXXXRTC.

Antibodies

The term "antibody" herein is used in the broadest sense and specifically covers monoclonal antibodies, polyclonal antibodies, dimers, multimers, multispecific antibodies (e.g., bispecific antibodies), multivalent antibodies and antibody fragments, so long as they exhibit the desired biological activity (Miller et al (2003) Jour. of Immunology 170:4854-4861). Antibodies may be murine, human, humanized, chimeric, or derived from other species. An antibody is a protein generated by the immune system that is capable of recognizing and binding to a specific antigen. (Janeway, C., Travers, P., Walport, M., Shlomchik (2001) Immuno Biology, 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin can be of any type (e.g. IgG, IgE, IgM, IgD, and IgA), class (e.g. IgG1, IgG2, IgG3, IgG4, IgA1 and IgA2) or subclass of immunoglobulin molecule. The immunoglobulins can be derived from any species, including human, murine, or rabbit origin.

"Antibody fragments" comprise a portion of a full length antibody, generally the antigen binding or variable region thereof. Examples of antibody fragments include Fab, Fab', F(ab')$_2$, and scFv fragments; diabodies; linear antibodies; fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

The term "monoclonal antibody" as used herein refers to an antibody obtained from a population of substantially homogeneous antibodies, i.e. the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al (1975) Nature 256:495, or may be made by recombinant DNA methods (see, U.S. Pat. No. 4,816,567). The monoclonal antibodies may also be isolated from phage antibody libraries using the techniques described in Clackson et al (1991) Nature, 352:624-628; Marks et al (1991) J. Mol. Biol., 222:581-597 or from transgenic mice carrying a fully human immunoglobulin system (Lonberg (2008) Curr. Opinion 20(4):450-459).

The monoclonal antibodies herein specifically include chimeric antibodies, humanized antibodies and human antibodies.

Examples of cell binding agents include those agents described for use in WO 2007/085930, which is incorporated herein.

Tumour-associate antigens and cognate antibodies for use in embodiments of the present invention are listed below, and are described in more detail on pages 14 to 86 of WO 2017/186894, which is incorporated herein.

(1) BMPR1B (bone morphogenetic protein receptor-type IB)

(2) E16 (LAT1, SLC7A5)

(3) STEAP1 (six transmembrane epithelial antigen of prostate)

(4) 0772P (CA125, MUC16)

(5) MPF (MPF, MSLN, SMR, megakaryocyte potentiating factor, mesothelin)

(6) Napi3b (NAPI-3B, NPTIIb, SLC34A2, solute carrier family 34 (sodium phosphate), member 2, type II sodium-dependent phosphate transporter 3b)

(7) Sema 5b (FLJ10372, KIAA1445, Mm.42015, SEMA5B, SEMAG, Semaphorin 5b Hlog, 25 sema domain, seven thrombospondin repeats (type 1 and type 1-like), transmembrane domain (TM) and short cytoplasmic domain, (semaphorin) 5B)

(8) PSCA hlg (2700050C12Rik, C530008016Rik, RIKEN cDNA 2700050C12, RIKEN cDNA 2700050C12 gene)

(9) ETBR (Endothelin type B receptor)

(10) MSG783 (RNF124, hypothetical protein FLJ20315)

(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein)

(12) TrpM4 (BR22450, FLJ20041, TRPM4, TRPM4B, transient receptor potential cation 5 channel, subfamily M, member 4)

(13) CRIPTO (CR, CR1, CRGF, CRIPTO, TDGF1, teratocarcinoma-derived growth factor)

(14) CD21 (CR2 (Complement receptor 2) or C3DR (C3d/Epstein Barr virus receptor) or Hs.73792)

(15) CD79b (CD79B, CD79β, IGb (immunoglobulin-associated beta), B29)

(16) FcRH2 (IFGP4, IRTA4, SPAP1A (SH2 domain containing phosphatase anchor protein 1a), SPAP1B, SPAP1C)

(17) HER2 (ErbB2)

(18) NCA (CEACAM6)

(19) MDP (DPEP1)

(20) IL20R-alpha (IL20Ra, ZCYTOR7)

(21) Brevican (BCAN, BEHAB)

(22) EphB2R (DRT, ERK, Hek5, EPHT3, Tyro5)

(23) ASLG659 (B7h)

(24) PSCA (Prostate stem cell antigen precursor)

(25) GEDA

(26) BAFF-R (B cell-activating factor receptor, BLyS receptor 3, BR3)

(27) CD22 (B-cell receptor CD22-B isoform, BL-CAM, Lyb-8, Lyb8, SIGLEC-2, FLJ22814)

(27a) CD22 (CD22 molecule)

(28) CD79a (CD79A, CD79alpha), immunoglobulin-associated alpha, a B cell-specific protein that covalently interacts with Ig beta (CD79B) and forms a complex on the surface with Ig M molecules, transduces a signal involved in B-cell differentiation), pI: 4.84, MW: 25028 TM: 2 [P] Gene Chromosome: 19q13.2).

(29) CXCR5 (Burkitt's lymphoma receptor 1, a G protein-coupled receptor that is activated by the CXCL13 chemokine, functions in lymphocyte migration and humoral defense, plays a 10 role in HIV-2 infection and perhaps development of AIDS, lymphoma, myeloma, and leukemia); 372 aa, pI: 8.54 MW: 41959 TM: 7 [P] Gene Chromosome: 11q23.3,

(30) HLA-DOB (Beta subunit of MHC class II molecule (Ia antigen) that binds peptides and 20 presents them to CD4+T lymphocytes); 273 aa, pI: 6.56, MW: 30820.TM: 1 [P] Gene Chromosome: 6p21.3)

(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability); 422 aa), pI: 7.63, MW: 47206 TM: 1 [P] Gene Chromosome: 17p13.3).

(32) CD72 (B-cell differentiation antigen CD72, Lyb-2); 359 aa, pI: 8.66, MW: 40225, TM: 1 5 [P] Gene Chromosome: 9p13.3).

(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis); 661 aa, pI: 6.20, MW: 74147 TM: 1 [P] Gene Chromosome: 5q12).

(34) FcRH1 (Fc receptor-like protein 1, a putative receptor for the immunoglobulin Fc domain that contains C2 type Ig-like and ITAM domains, may have a role in B-lymphocyte 20 differentiation); 429 aa, pI: 5.28, MW: 46925 TM: 1 [P] Gene Chromosome: 1q21-1q22)

(35) IRTA2 (Immunoglobulin superfamily receptor translocation associated 2, a putative immunoreceptor with possible roles in B cell development and lymphomagenesis; deregulation of the gene by translocation occurs in some B cell malignancies); 977 aa, pI: 6.88, MW: 106468, TM: 1 [P] Gene Chromosome: 1q21)

(36) TENB2 (TMEFF2, tomoregulin, TPEF, HPP1, TR, putative transmembrane 35 proteoglycan, related to the EGF/heregulin family of growth factors and follistatin); 374 aa)

(37) PSMA-FOLH1 (Folate hydrolase (prostate-specific membrane antigen) 1)

(38) SST (Somatostatin Receptor; note that there are 5 subtypes)

(38.1) SSTR2 (Somatostatin receptor 2)

(38.2) SSTR5 (Somatostatin receptor 5)

(38.3) SSTR1

(38.4) SSTR3

(38.5) SSTR4

AvB6—Both Subunits (39+40)

(39) ITGAV (Integrin, alpha V)

(40) ITGB6 (Integrin, beta 6)

(41) CEACAM5 (Carcinoembryonic antigen-related cell adhesion molecule 5)

(42) MET (met proto-oncogene; hepatocyte growth factor receptor)

(43) MUC1 (Mucin 1, cell surface associated)

(44) CA9 (Carbonic anhydrase IX)

(45) EGFRvIII (Epidermal growth factor receptor (EGFR), transcript variant 3,

(46) CD33 (CD33 molecule)

(47) CD19 (CD19 molecule)

(48) IL2RA (Interleukin 2 receptor, alpha); NCBI Reference Sequence: NM_000417.2);

(49) AXL (AXL receptor tyrosine kinase)

(50) CD30-TNFRSF8 (Tumor necrosis factor receptor superfamily, member 8)

(51) BCMA (B-cell maturation antigen)-TNFRSF17 (Tumor necrosis factor receptor superfamily, member 17)

(52) CT Ags-CTA (Cancer Testis Antigens)

(53) CD174 (Lewis Y)-FUT3 (fucosyltransferase 3 (galactoside 3(4)-L-fucosyltransferase, Lewis blood group)

(54) CLEC14A (C-type lectin domain family 14, member A; Genbank accession no. NM175060)

(55) GRP78-HSPA5 (heat shock 70 kDa protein 5 (glucose-regulated protein, 78 kDa)

(56) CD70 (CD70 molecule) L08096

(57) Stem Cell specific antigens. For example:
5T4 (see entry (63) below)
CD25 (see entry (48) above)
CD32
LGR5/GPR49
Prominin/CD133

(58) ASG-5
(59) ENPP3 (Ectonucleotide pyrophosphatase/phosphodiesterase 3)
(60) PRR4 (Proline rich 4 (lacrimal))
(61) GCC-GUCY2C (guanylate cyclase 2C (heat stable enterotoxin receptor)
(62) Liv-1-SLC39A6 (Solute carrier family 39 (zinc transporter), member 6)
(63) 5T4, Trophoblast glycoprotein, TPBG-TPBG (trophoblast glycoprotein)
(64) CD56-NCMA1 (Neural cell adhesion molecule 1)
(65) CanAg (Tumor associated antigen CA242)
(66) FOLR1 (Folate Receptor 1)
(67) GPNMB (Glycoprotein (transmembrane) nmb)
(68) TIM-1-HAVCR1 (Hepatitis A virus cellular receptor 1)
(69) RG-1/Prostate tumor target Mindin-Mindin/RG-1
(70) B7-H4-VTCN1 (V-set domain containing T cell activation inhibitor 1
(71) PTK7 (PTK7 protein tyrosine kinase 7)
(72) CD37 (CD37 molecule)
(73) CD138-SDC1 (syndecan 1)
(74) CD74 (CD74 molecule, major histocompatibility complex, class II invariant chain)
(75) Claudins-CLs (Claudins)
(76) EGFR (Epidermal growth factor receptor)
(77) Her3 (ErbB3)-ERBB3 (v-erb-b2 erythroblastic leukemia viral oncogene homolog 3 (avian))
(78) RON-MST1R (macrophage stimulating 1 receptor (c-met-related tyrosine kinase))
(79) EPHA2 (EPH receptor A2)
(80) CD20-MS4A1 (membrane-spanning 4-domains, subfamily A, member 1)
(81) Tenascin C-TNC (Tenascin C)
(82) FAP (Fibroblast activation protein, alpha)
(83) DKK-1 (Dickkopf 1 homolog (*Xenopus laevis*)
(84) CD52 (CD52 molecule)
(85) CS1-SLAMF7 (SLAM family member 7)
(86) Endoglin-ENG (Endoglin)
(87) Annexin A1-ANXA1 (Annexin A1)
(88) V-CAM (CD106)-VCAM1 (Vascular cell adhesion molecule 1)

An additional tumour-associate antigen and cognate antibodies of interest are:
(89) ASCT2 (ASC transporter 2, also known as SLC1A5). ASCT2 antibodies are described in WO 2018/089393, which is incorporated herein by

REFERENCE

The cell binding agent may be labelled, for example to aid detection or purification of the agent either prior to incorporation as a conjugate, or as part of the conjugate. The label may be a biotin label. In another embodiment, the cell binding agent may be labelled with a radioisotope.

Methods of Treatment

The compounds of the present invention may be used in a method of therapy. Also provided is a method of treatment, comprising administering to a subject in need of treatment a therapeutically-effective amount of a conjugate of formula II. The term "therapeutically effective amount" is an amount sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

A conjugate may be administered alone or in combination with other treatments, either simultaneously or sequentially dependent upon the condition to be treated. Examples of treatments and therapies include, but are not limited to, chemotherapy (the administration of active agents, including, e.g. drugs; surgery; and radiation therapy).

Pharmaceutical compositions according to the present invention, and for use in accordance with the present invention, may comprise, in addition to the active ingredient, i.e. a conjugate of formula II, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous, or intravenous.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such as gelatin.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

The Conjugates can be used to treat proliferative disease and autoimmune disease. The term "proliferative disease" pertains to an unwanted or uncontrolled cellular proliferation of excessive or abnormal cells which is undesired, such as, neoplastic or hyperplastic growth, whether in vitro or in vivo.

Examples of proliferative conditions include, but are not limited to, benign, pre-malignant, and malignant cellular proliferation, including but not limited to, neoplasms and tumours (e.g., histocytoma, glioma, astrocyoma, osteoma), cancers (e.g. lung cancer, small cell lung cancer, gastrointestinal cancer, bowel cancer, colon cancer, breast carinoma, ovarian carcinoma, prostate cancer, testicular cancer, liver cancer, kidney cancer, bladder cancer, pancreatic cancer, brain cancer, sarcoma, osteosarcoma, Kaposi's sarcoma, melanoma), leukemias, psoriasis, bone diseases, fibroproliferative disorders (e.g. of connective tissues), and atherosclerosis. Other cancers of interest include, but are not limited to, haematological; malignancies such as leukemias and lymphomas, such as non-Hodgkin lymphoma, and subtypes such as DLBCL, marginal zone, mantle zone, and follicular, Hodgkin lymphoma, AML, and other cancers of B or T cell origin.

Examples of autoimmune disease include the following: rheumatoid arthritis, autoimmune demyelinative diseases (e.g., multiple sclerosis, allergic encephalomyelitis), psoriatic arthritis, endocrine ophthalmopathy, uveoretinitis, systemic lupus erythematosus, myasthenia gravis, Graves' disease, glomerulonephritis, autoimmune hepatological disorder, inflammatory bowel disease (e.g., Crohn's disease), anaphylaxis, allergic reaction, Sjögren's syndrome, type I diabetes mellitus, primary biliary cirrhosis, Wegener's granulomatosis, fibromyalgia, polymyositis, dermatomyositis, multiple endocrine failure, Schmidt's syndrome, autoimmune uveitis, Addison's disease, adrenalitis, thyroiditis, Hashimoto's thyroiditis, autoimmune thyroid disease, pernicious anemia, gastric atrophy, chronic hepatitis, lupoid hepatitis, atherosclerosis, subacute cutaneous lupus erythematosus, hypoparathyroidism, Dressler's syndrome, autoimmune thrombocytopenia, idiopathic thrombocytopenic purpura, hemolytic anemia, pemphigus vulgaris, pemphigus, dermatitis herpetiformis, alopecia arcata, pemphigoid, scleroderma, progressive systemic sclerosis, CREST syndrome (calcinosis, Raynaud's phenomenon, esophageal dysmotility, sclerodactyly, and telangiectasia), male and female autoimmune infertility, ankylosing spondolytis, ulcerative colitis, mixed connective tissue disease, polyarteritis nedosa, systemic necrotizing vasculitis, atopic dermatitis, atopic rhinitis, Goodpasture's syndrome, Chagas' disease, sarcoidosis, rheumatic fever, asthma, recurrent abortion, antiphospholipid syndrome, farmer's lung, erythema multiforme, post cardiotomy syndrome, Cushing's syndrome, autoimmune chronic active hepatitis, bird-fancier's lung, toxic epidermal necrolysis, Alport's syndrome, alveolitis, allergic alveolitis, fibrosing alveolitis, interstitial lung disease, erythema nodosum, pyoderma gangrenosum, transfusion reaction, Takayasu's arteritis, polymyalgia rheumatica, temporal arteritis, schistosomiasis, giant cell arteritis, ascariasis, aspergillosis, Sampter's syndrome, eczema, lymphomatoid granulomatosis, Behcet's disease, Caplan's syndrome, Kawasaki's disease, dengue, encephalomyelitis, endocarditis, endomyocardial fibrosis, endophthalmitis, erythema elevatum et diutinum, psoriasis, erythroblastosis fetalis, eosinophilic faciitis, Shulman's syndrome, Felty's syndrome, filariasis, cyclitis, chronic cyclitis, heterochronic cyclitis, Fuch's cyclitis, IgA nephropathy, Henoch-Schonlein purpura, graft versus host disease, transplantation rejection, cardiomyopathy, Eaton-Lambert syndrome, relapsing polychondritis, cryoglobulinemia, Waldenstrom's macroglobulemia, Evan's syndrome, and autoimmune gonadal failure.

In some embodiments, the autoimmune disease is a disorder of B lymphocytes (e.g., systemic lupus erythematosus, Goodpasture's syndrome, rheumatoid arthritis, and type I diabetes), Th1-lymphocytes (e.g., rheumatoid arthritis, multiple sclerosis, psoriasis, Sjögren's syndrome, Hashimoto's thyroiditis, Graves' disease, primary biliary cirrhosis, Wegener's granulomatosis, tuberculosis, or graft versus host disease), or Th2-lymphocytes (e.g., atopic dermatitis, systemic lupus erythematosus, atopic asthma, rhinoconjunctivitis, allergic rhinitis, Omenn's syndrome, systemic sclerosis, or chronic graft versus host disease). Generally, disorders involving dendritic cells involve disorders of Th1-lymphocytes or Th2-lymphocytes. In some embodiments, the autoimmune disorder is a T cell-mediated immunological disorder.

In some embodiments, the amount of the Conjugate administered ranges from about 0.01 to about 10 mg/kg per dose. In some embodiments, the amount of the Conjugate administered ranges from about 0.01 to about 5 mg/kg per dose. In some embodiments, the amount of the Conjugate administered ranges from about 0.05 to about 5 mg/kg per dose. In some embodiments, the amount of the Conjugate administered ranges from about 0.1 to about 5 mg/kg per dose. In some embodiments, the amount of the Conjugate administered ranges from about 0.1 to about 4 mg/kg per dose. In some embodiments, the amount of the Conjugate administered ranges from about 0.05 to about 3 mg/kg per dose. In some embodiments, the amount of the Conjugate administered ranges from about 0.1 to about 3 mg/kg per dose. In some embodiments, the amount of the Conjugate administered ranges from about 0.1 to about 2 mg/kg per dose.

Drug Loading

The drug loading (p) is the average number of ABD drugs per cell binding agent, e.g. antibody. Where the compounds of the invention are bound to cysteines, drug loading may range from 1 to 8 drugs (D) per cell binding agent, i.e. where 1, 2, 3, 4, 5, 6, 7, and 8 drug moieties are covalently attached to the cell binding agent. Compositions of conjugates include collections of cell binding agents, e.g. antibodies, conjugated with a range of drugs, from 1 to 8. Where the compounds of the invention are bound to lysines, drug loading may range from 1 to 80 drugs (D) per cell binding agent, although an upper limit of 40, 20, 10 or 8 may be preferred. Compositions of conjugates include collections of cell binding agents, e.g. antibodies, conjugated with a range of drugs, from 1 to 80, 1 to 40, 1 to 20, 1 to 10 or 1 to 8.

The average number of drugs per antibody in preparations of ADC from conjugation reactions may be characterized by conventional means such as UV, reverse phase HPLC, HIC, mass spectroscopy, ELISA assay, and electrophoresis. The quantitative distribution of ADC in terms of p may also be determined. By ELISA, the averaged value of p in a particular preparation of ADC may be determined (Hamblett et al (2004) Clin. Cancer Res. 10:7063-7070; Sanderson et al (2005) Clin. Cancer Res. 11:843-852). However, the distribution of p (drug) values is not discernible by the antibody-antigen binding and detection limitation of ELISA. Also, ELISA assay for detection of antibody-drug conjugates does not determine where the drug moieties are attached to the antibody, such as the heavy chain or light chain fragments, or the particular amino acid residues. In some instances, separation, purification, and characterization of homogeneous ADC where p is a certain value from ADC with other drug loadings may be achieved by means such as reverse phase HPLC or electrophoresis. Such techniques are also applicable to other types of conjugates.

For some antibody-drug conjugates, p may be limited by the number of attachment sites on the antibody. For example, an antibody may have only one or several cysteine thiol groups, or may have only one or several sufficiently reactive thiol groups through which a linker may be attached. Higher drug loading, e.g. p>5, may cause aggregation, insolubility, toxicity, or loss of cellular permeability of certain antibody-drug conjugates.

Typically, fewer than the theoretical maximum of drug moieties are conjugated to an antibody during a conjugation reaction. An antibody may contain, for example, many lysine residues that do not react with the Drug Linker. Only the most reactive lysine groups may react with an amine-reactive linker reagent. Also, only the most reactive cysteine thiol groups may react with a thiol-reactive linker reagent. Generally, antibodies do not contain many, if any, free and reactive cysteine thiol groups which may be linked to a drug moiety. Most cysteine thiol residues in the antibodies of the compounds exist as disulfide bridges and must be reduced with a reducing agent such as dithiothreitol (DTT) or TCEP, under partial or total reducing conditions. The loading (drug/antibody ratio) of an ADC may be controlled in several different manners, including: (i) limiting the molar excess of Drug Linker relative to antibody, (ii) limiting the conjugation reaction time or temperature, and (iii) partial or limiting reductive conditions for cysteine thiol modification.

Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by engineering one, two, three, four, or more cysteine residues (e.g., preparing mutant antibodies comprising one or more non-native cysteine amino acid residues). U.S. Pat. No. 7,521,541 teaches engineering antibodies by introduction of reactive cysteine amino acids.

Cysteine amino acids may be engineered at reactive sites in an antibody and which do not form intrachain or intermolecular disulfide linkages (Junutula, et al., 2008b Nature Biotech., 26(8):925-932; Dornan et al (2009) Blood 114 (13):2721-2729; U.S. Pat. Nos. 7,521,541; 7,723,485; WO2009/052249). The engineered cysteine thiols may react with linker reagents or the drug-linker reagents of the present invention which have thiol-reactive, electrophilic groups such as maleimide or alpha-halo amides to form ADC with cysteine engineered antibodies and the ABD drug moieties. The location of the drug moiety can thus be designed, controlled, and known. The drug loading can be controlled since the engineered cysteine thiol groups typically react with thiol-reactive linker reagents or drug-linker reagents in high yield. Engineering an IgG antibody to introduce a cysteine amino acid by substitution at a single site on the heavy or light chain gives two new cysteines on the symmetrical antibody. A drug loading near 2 can be achieved with near homogeneity of the conjugation product ADC.

Where more than one nucleophilic or electrophilic group of the antibody reacts with a drug-linker intermediate, or linker reagent followed by drug moiety reagent, then the resulting product is a mixture of ADC compounds with a distribution of drug moieties attached to an antibody, e.g. 1, 2, 3, etc. Liquid chromatography methods such as polymeric reverse phase (PLRP) and hydrophobic interaction (HIC) may separate compounds in the mixture by drug loading value. Preparations of ADC with a single drug loading value (p) may be isolated, however, these single loading value ADCs may still be heterogeneous mixtures because the drug moieties may be attached, via the linker, at different sites on the antibody.

Thus the antibody-drug conjugate compositions of the invention include mixtures of antibody-drug conjugate compounds where the antibody has one or more ABD drug moieties and where the drug moieties may be attached to the antibody at various amino acid residues.

In one embodiment, the average number of dimer azetidobenzodiazepine groups per cell binding agent is in the range 1 to 20. In some embodiments the range is selected from 1 to 8, 2 to 8, 2 to 6, 2 to 4, and 4 to 8.

In some embodiments, there is one dimer azetidobenzodiazepine group per cell binding agent.

General Synthetic Routes

A large number of suitable N-Prot$^N$, O-Prot$^O$ and Y-Prot$^Y$ protecting groups are described in Greene, T. W. and Wuts, G. M., Protective Groups in Organic Synthesis, 3$^{rd}$ Edition, John Wiley & Sons, Inc., 1999, which is incorporated herein by reference.

Synthesis of Compounds of Formula IV

A possible step in the synthesis of the compounds of the first aspect of the invention, particularly the compound of formula IV, is illustrated in Scheme 1. This starts from a N10 protected ABD dimer (d1A).

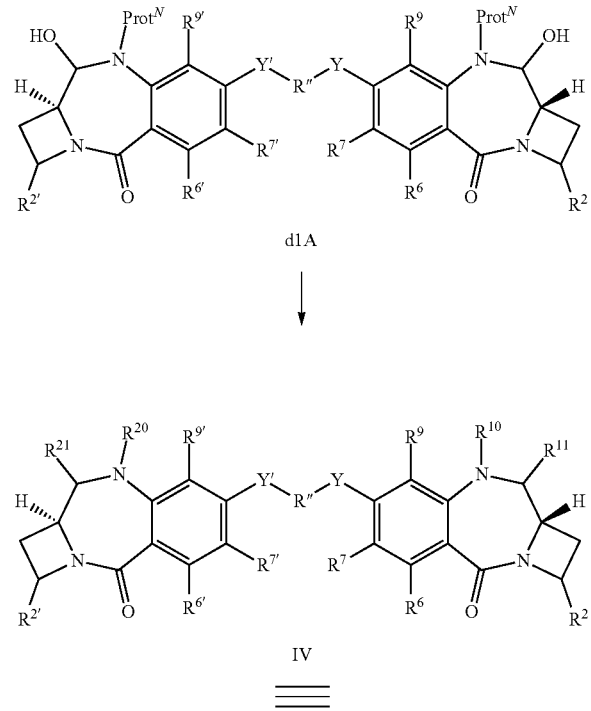

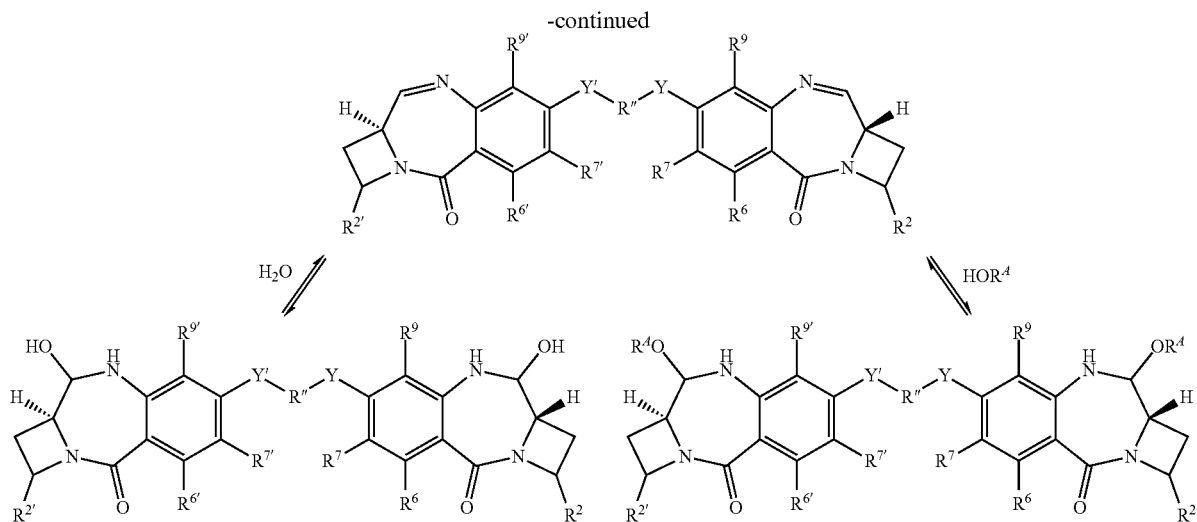

The dimer d1A is deprotected at the N10 position by standard method to afford the compound of formula IV. In cases where $Prot^N$ is Alloc, deprotection is carried out using palladium. The compound produced may be in its carbinolamine or carbinolamine ether form depending on the solvents used, in equilibrium with an imine.

In the case of ABDs, the ring strain for the four membered azetidine ring means the carbinolamine form is dominant in the equilibrium.

An alternative step in the synthesis of the compounds of formula IV is illustrated in Scheme 2. This starts from the N10 nitrogen protected ABD monomer (m2A).

Scheme 2

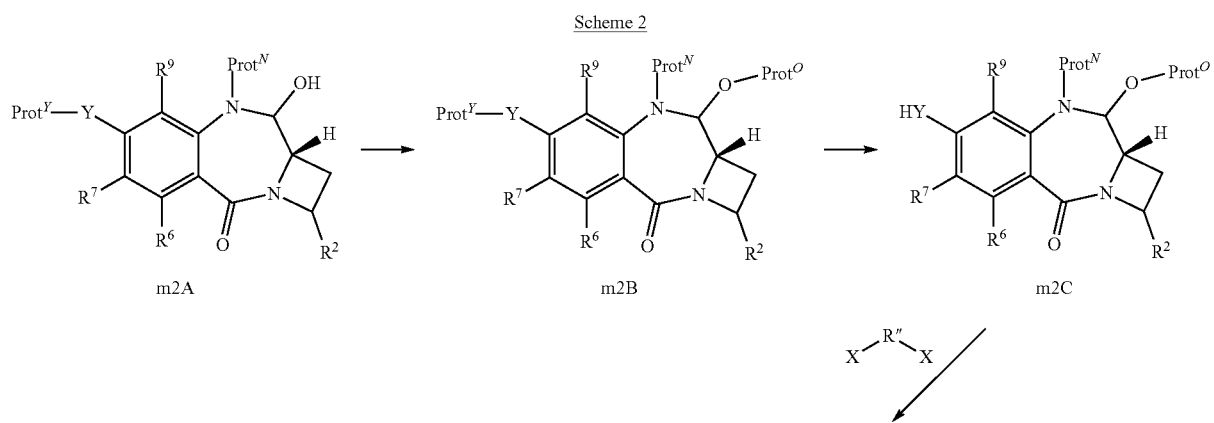

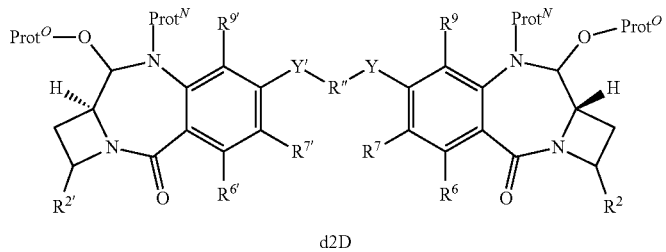

-continued

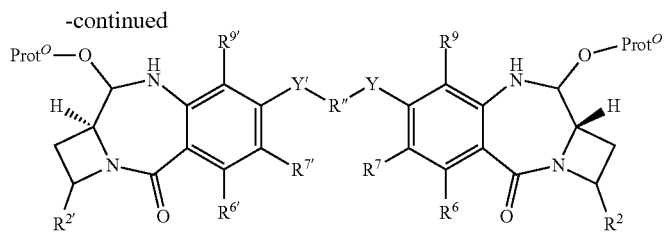

d2E

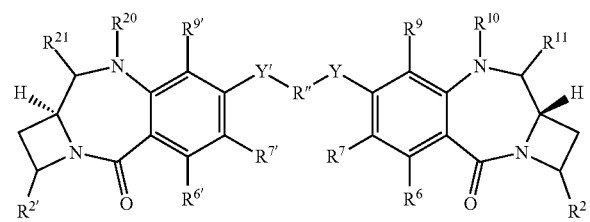

IV

The N10 and Y8 position protected ABD monomer m2A is protected at the C11 position alcohol to give m2B. Preferably, $Prot^O$ is TBS and the protection is achieved by addition of excess TBS-Cl. Subsequent deprotection of the $Prot^Y$-Y protecting group provides a dimerisable species (m2C). When $Prot^Y$ is TIPS, deprotection may be achieved with LiOAc in DMF and water.

m2C is reacted with a dimer linker $R''(X)_2$ to afford the dimer d2D. Typically, Y is O and X is a halogen (preferably Br). In this case, a double Williamson ether synthesis forms the dimer, using a TBAI additive.

The N10 protecting group is removed from the dimer product to give d2E. For example if $Prot^N$ is Alloc and $Prot^O$ is an oxygen protecting group for synthesis, then the deprotection is carried using palladium to remove the N10 protecting group, followed by the elimination of the oxygen protecting group for synthesis. If $Prot^N$ is Troc and $Prot^O$ is an oxygen protecting group for synthesis, then the deprotection is carried out using a Cd/Pb couple. If $Prot^N$ is SEM, or an analogous group, and $Prot^O$ is an oxo group, then the oxo group can be removed by reduction, which leads to a protected carbinolamine intermediate, which can then be treated to remove the SEM protecting group followed by the elimination of water. Removal of the C11 position alcohol protecting group provides the compound of formula IV. If $Prot^O$ is TBS, the alcohol deprotection may occur concomitantly with the aforementioned Alloc N-deprotection using palladium and pyrrolidine in DCM.

The dimer d1A and monomer m2A required for Schemes 1 and 2 respectively, may be synthesised by several routes. One possible route, via oxidative ring closure, is illustrated in Scheme 3.

Scheme 3

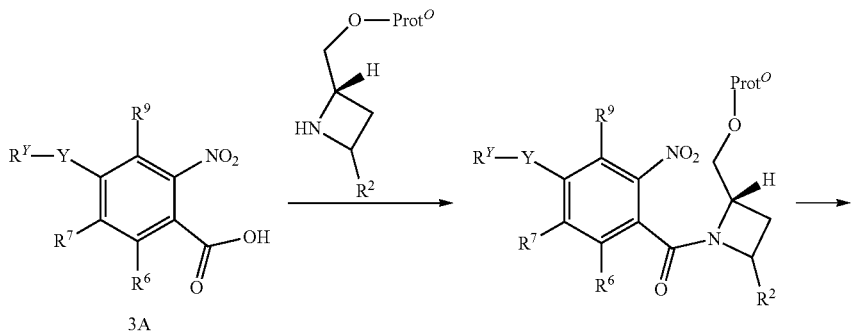

3A

3B

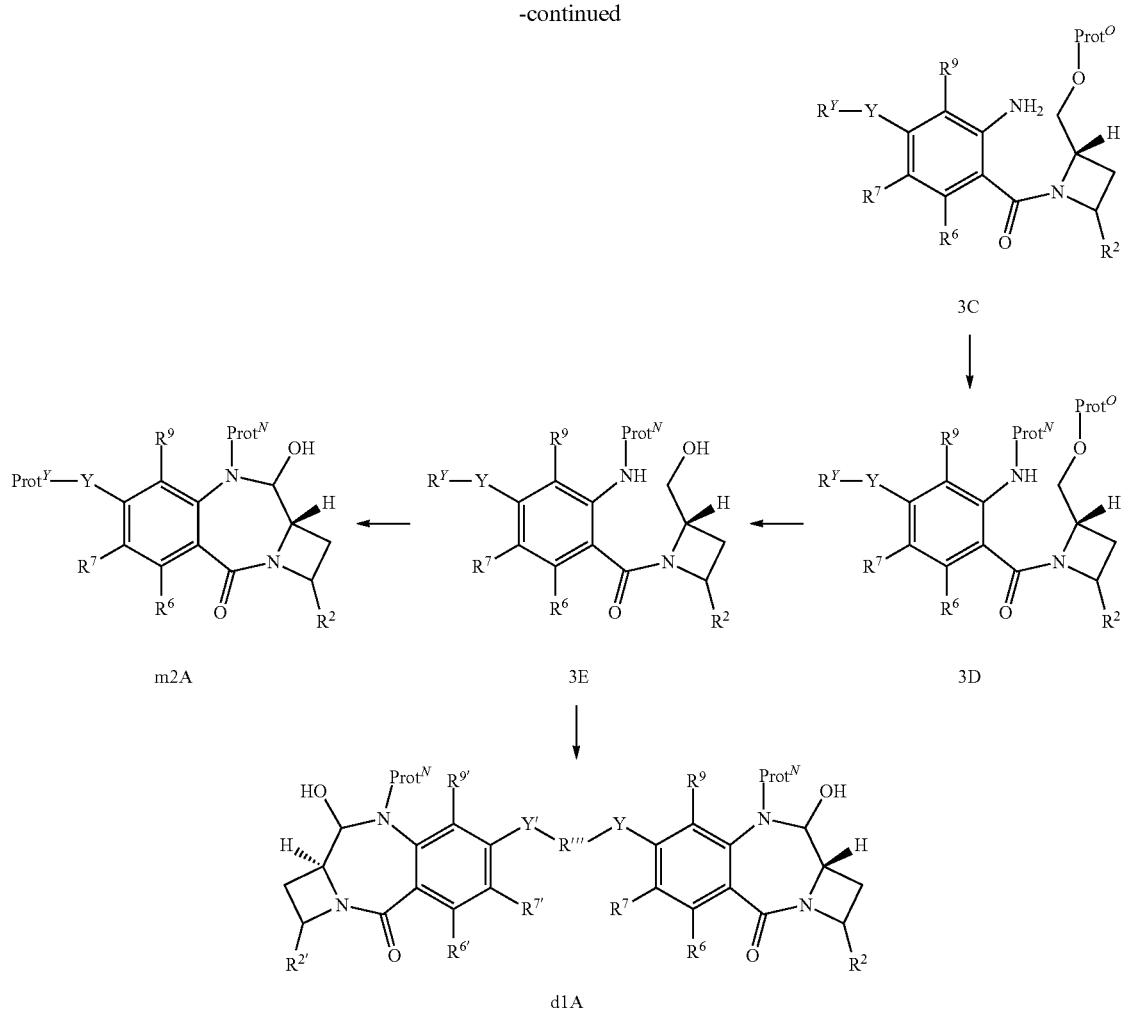

m2A  3E  3D d1A

The compounds 3A, 3B, 3C, 3D and 3E may be dimeric (where the group $R^Y$ represents R''' connected to a similar ABD precursor) or monomeric (where the group $R^Y$ represents a suitable protecting group).

Monomeric 3A is a nitrobenzoic acid derivative. Many such derivatives are commercially available and others can be synthesised by conventional methods (e.g. Althuis, T. H. and Hess, H. J., J Medicinal Chem., 20(1), 146-266 (1977)). Often the nitrobenzoic acid is derived from the ester, by ester hydrolysis under mild conditions (such as with LiOH). Dimeric 3A may be made by various strategies disclosed in the prior art (e.g. Scheme 3 of WO 00/12508). For example, appropriate benzoic acid esters may be dimerised about a suitable diol by Mitsunobo etherification, followed by nitration and hydrolysis. Alternatively, benzoic acid esters may be dimerised about a suitable dihalide by Williamson ether synthesis. Further transformations required to afford monomeric and dimeric 3A are available in the literature.

The azetidine starting material may be synthesised via modification of comparable proline syntheses disclosed in the prior art (e.g. Scheme 4 of WO 00/12508). Strategies pertaining specifically to azetidine are also known in the literature (e.g. Bose, D. S., et al., Tetrahedron Letters, 38(33), 5839-5842, 1997; doi: 10.1016/S0040-4039(97) 01297-5). For example, commercially available azetidine-2-carboxylic acid, may be protected at the azetidine nitrogen by a suitable protecting group, such as Cbz, before acidic esterification to achieve the methyl ester. The ester may be reduced with $LiBH_4$ in THF to yield Cbz protected 2-(hydroxymethyl)azetidine. In some approaches, an appropriate protecting group ($Prot^O$), such as TBS, may be added to the alcohol by reaction with TBS-Cl. In other approaches, the alcohol is left unprotected. In scheme 3, $Prot^O$ may represent either a suitable protecting group or H— a suitable $Prot^O$ group should be able to withstand $NO_2$ reduction conditions. Next, the nitrogen protecting group is removed, typically by reduction under $H_2$ gas, to yield the azetidine starting material required in Scheme 3.

The compound 3A is condensed with the azetidine starting material to afford 3B. Often the condensation is achieved via a DCC coupling or via an acid chloride (formed from the carboxylic acid with oxalyl chloride or $SOCl_2$), or with HOBt in DCM at low temperature.

The nitro group of 3B is reduced to the amine (3C), using standard procedures such as $SnCl_2$ in MeOH, or Zinc in MeOH/$H_2$O/formic acid (90:5:5), or sodium dithionite, or Raney Nickel and hydrazine, or catalytic hydrogenation over palladium on charcoal. The method selected depends on the requirements of the hydroxyl protecting group.

The resulting amine is singly protected by a suitable protecting group to afford 3D. The N-$Prot^N$ group is preferably a carbamate, such as N-Alloc. The nucleophilicity of the amine is reduced upon protection with Alloc, so singular protection is favoured. Typically, this is achieved by reaction with pyridine and one equivalent of allyl chloroformate. When $Prot^O$ is H, then 3D is equivalent to 3E. When $Prot^O$ is a protecting group it is removed to give alcohol 3E under standard conditions. If $Prot^O$ is an acetate protecting group it may be removed under mild basic conditions (e.g. $K_2CO_3$), or if $Prot^O$ is a silyl ether protecting group, such as TBS, it may be removed by using TBAF or mild acid.

Oxidative ring closure of via the aldehyde, or a functional equivalent, from dimeric 3E affords d1A (for further reaction as per Scheme 1) and from monomeric 3E afford m2A (for further reaction as per Scheme 2). The selective alcohol-aldehyde oxidation may be achieved by exposure to tetrapropylammoniumperruthenate (TPAP) in N-methylmorpholine N-oxide (NMO) over molecular sieves, or by Swern oxidation (with DMSO and oxalyl chloride), or by Dess-Martin oxidation (with DMP) or preferably by Cu(I)/TEMPO radical oxidation (with Tetrakisacetonitrile copper (I) triflate, 1-hydroxy-2,2,6,6-tetramethyl-piperidine (TEMPO), 1-methylimidazole and 2-(2-pyridyl)pyridine). The latter is favoured as it does not require rigorous anhydrous conditions and there is no evidence of over oxidation to the ABD dilactam species. The aldehyde species undergoes spontaneous B-ring closure involving attack thereon by the singly protected N10 position.

An alternative route to the dimer d1A and monomer m2A is illustrated in Scheme 4. This route uses aldehyde unmasking to mediate ring closure.

The compounds 3A, 41B, 4C and 40 may be dimeric (where the group $R^Y$ represents R" connected to a similar ABD precursor) or monomeric (where the group $R^Y$ represents a suitable protecting group).

3A monomer and dimer variants may be generated by the strategies discussed above, in relation to Scheme 3. The azetidine starting material features a thioacetal in the 2-position (although other masked aldehyde equivalents may be used). The diethyl thioacetal azetidine may be prepared by the modification of similar proline synthetic strategies (e.g. Langley, D. R. & Thurston, D. E., J Organic Chemistry, 52, 91-97 (1987)). Routes pertaining specifically to azetidine are also known in the literature (e.g. Bose, D. S., et al., Tetrahedron Letters, 38(33), 5839-5842, 1997; doi: 10.1016/S0040-4039(97)01297-5). For example, Cbz protected 2-(hydroxymethyl)azetidine may be prepared as described above (for Scheme 3). The alcohol is then typically reoxidized to the aldehyde by Dess-Martin oxidation (with DMP) or IBX in DMSO. The resulting aldehyde is preferably condensed with a thiol such as EtSH, with a mild acid catalyst, such as TMSCI in protic solvent, to achieve the thioacetal. The thioacetal is incompatible with $H_2$ gas reduction, so the N-protecting group (e.g. Cbz) is often removed with TMS-1 in DCM. This results in the diethyl thioacetal azetidine starting material.

Direct condensation of 3A with the thioacetal azetidine starting material affords 4B. The nitro group of 4B may be reduced to the amine (4C) via the methods discussed above in relation to Scheme 3, preferably by the Tin(II)chloride method ($SnCl_2$ in MeOH) or Zinc in MeOH/$H_2$O/formic acid (90:5:5). Reduction is preferably not via direct hydrogenation due to incompatibility of the thioacetal group. The amine is singly protected by a suitable amine protecting group, such as Alloc, by reaction with the corresponding chloroformate or acid chloride. The N-$Prot^N$ group of 4D is preferably a carbamate, such as N-Alloc, as these species favour single protection.

Selective unmasking of the thioacetal to the aldehyde results in spontaneous cyclisation of the B-ring, by attack thereon by the singly protected N10 position. Typically, un-masking is mediated by Mercury(II), for example $HgCl_2$ with $CaCO_3$ in acetonitrile:water. For dimeric 4D this provides d1A (for further reaction as per Scheme 1) and for monomeric 4D this provides m2A (for further reaction as per Scheme 2).

Dimeric or monomeric thioacetal 4B (as per Scheme 4) may be synthesised via an alternative route, illustrated in Scheme 5. This route generates the thioacetal in situ.

Scheme 5

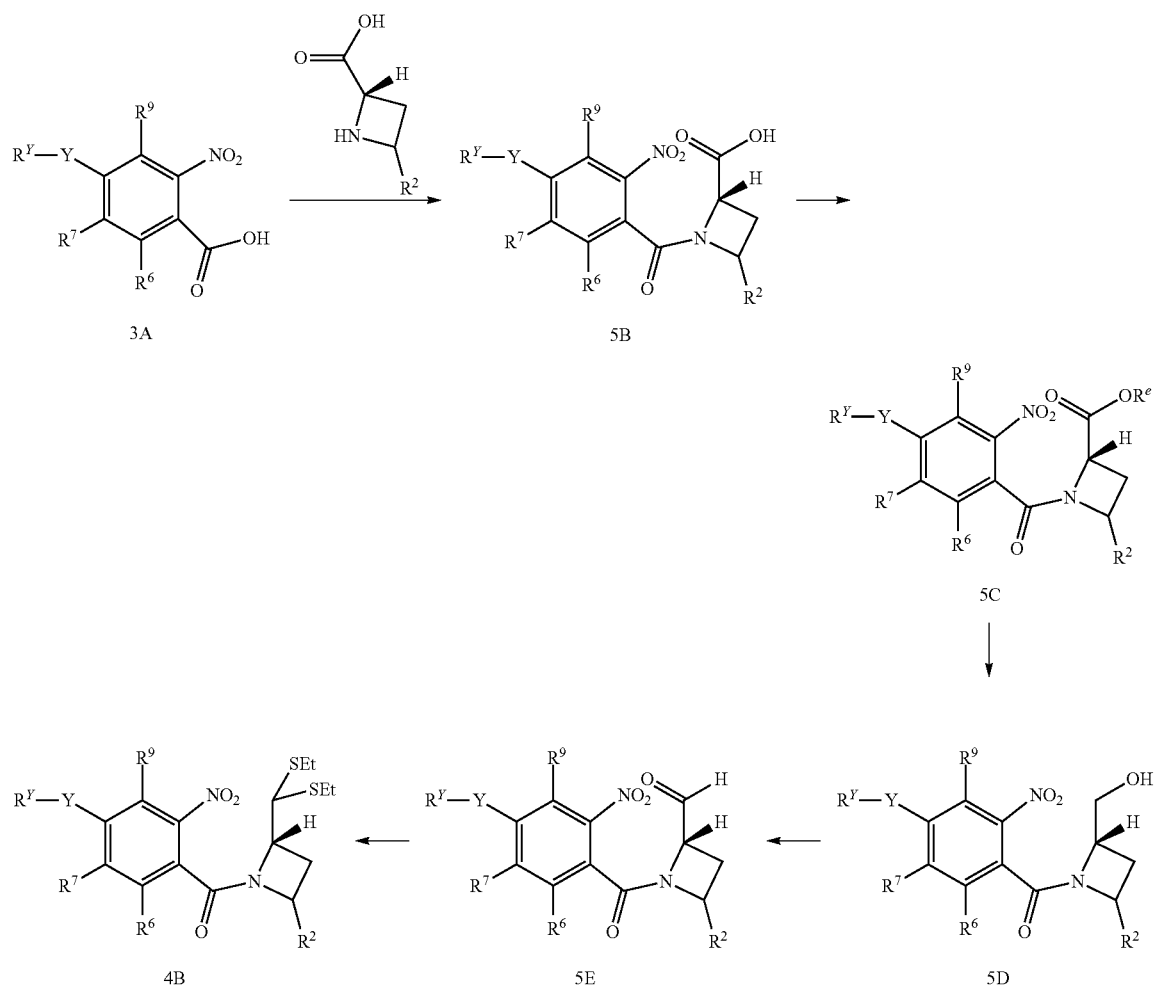

Synthetic strategies to achieve monomeric and dimeric 3A are discussed above with relation to Scheme 3. 3A is condensed with commercially available azetidine-2-carboxylic acid to afford 5B. The route from 5B to 4B follows a similar approach as the synthesis of the thioacetal azetidine starting material from azetidine-2-carboxylic (as discussed with relation to Scheme 4).

5C is reduced by a hydride reducing agent, typically by LiBH$_4$, to the secondary alcohol 5D. 5D is then reoxidised to the aldehyde (5E), often by a hypervalent iodine species (e.g. IBX or DMP). The thioacetal is generated in situ, preferably using EtSH under acidic conditions, to provide the compound 4B. This can be further reacted as per Scheme 4 to reach the desired ABD species.

Synthesis of Compounds of Formula I

A possible step in the synthesis of the compounds of the second aspect of the invention, particularly the compound of formula I, is illustrated in Scheme 6. This starts with two cyclised ABD monomers: m2A with a Prot$^N$ protected N10 position and m6A with a R$^L$ appended N10-nitrogen.

The compound of formula I may exist in equilibrium between the imine and the carbinolamine or carbinolamine ether form, depending on the solvent used (analogous to the equilibrium illustrated in Scheme 1 for Formula IV).

In some embodiments, Prot$^N$ may be equivalent to the R$^{30}$ substituent of formula I (described by option (d) i, ii and iii of the second aspect of the invention).

Scheme 6

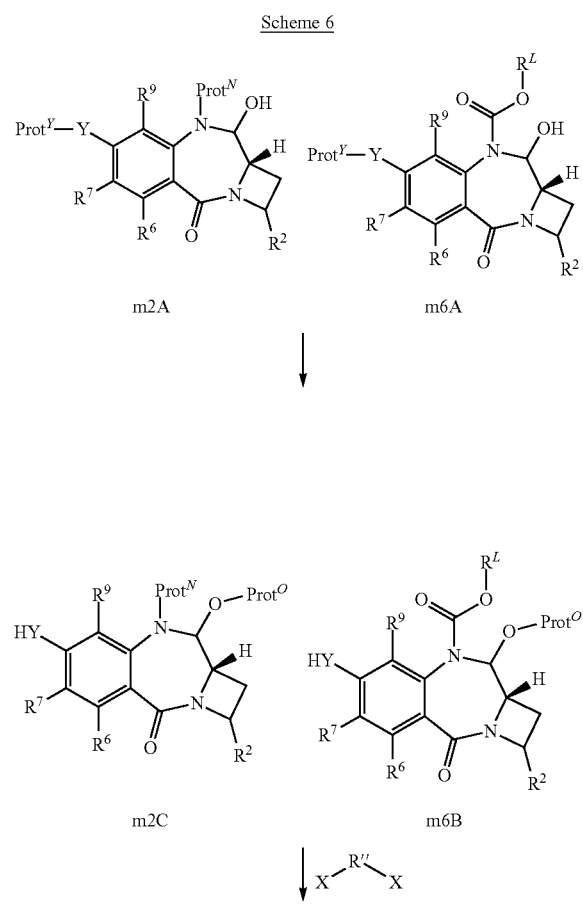

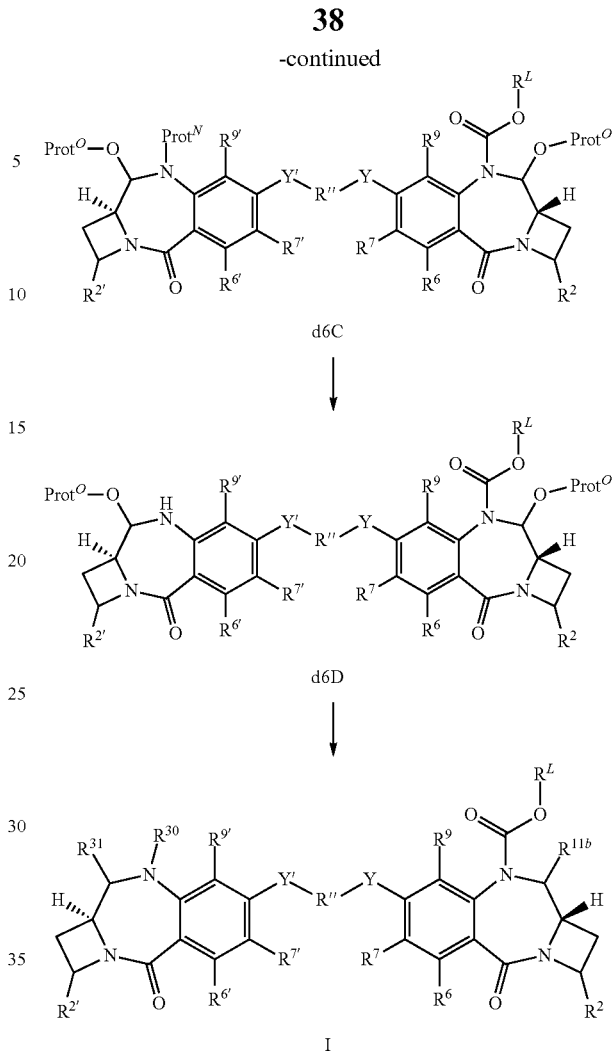

The m2A starting material may be prepared as per Schemes 3, 4, and 5. For compounds where Prot$^N$ is equivalent to the R$^{30}$ carbamate linker groups, then m2A is prepared via the isocyanate (i.e. the same route as m6A—discussed below).

m2A and m6A may be dimerised about the Y8 position with a dimer linker R", using a similar strategy as described in relation to Scheme 2. The C11 position alcohol is protected by Prot$^O$, where Prot$^O$ is preferably TBS and is introduced by reaction with TBS-Cl. The subsequent removal of the Prot$^Y$ group, where Prot$^Y$ is TIPS, may occur with LiOAc in DMF and water, to afford m2C and m6B respectively.

m2C and m6B are further reacted with R"(X)$_2$ to afford the dimer d6C. Typically, Y is O and X is a halogen (preferably Br). In this case, TBAI additive may drive a double Williamson ether synthesis to form the dimer. Alternative strategies for dimerisation are also known in the art, for example, via Mitsonobu etherification.

In some embodiments, the N10 protecting group is removed from the non-linker ABD to afford the asymmetric dimer d6D. Various deprotection strategies are discussed in relation to Scheme 1 and 2. In cases where Prot$^N$ is Alloc, then the deprotection may be carried out with palladium.

In other embodiments, the N10 protecting group is not removed. d6C is transformed directly to a compound of formula I by removal of Prot$^O$.

Removal of the C11 position alcohol protecting groups provides the asymmetrical compound of formula 1. If $Prot^O$ is TBS, the alcohol deprotection may occur concomitantly with the Alloc N10 position deprotection with palladium and pyrrolidine in DCM.

A possible synthesis of monomer m6A (required for Scheme 6) and an alternative route to the compounds of formula I are illustrated in Scheme 7.

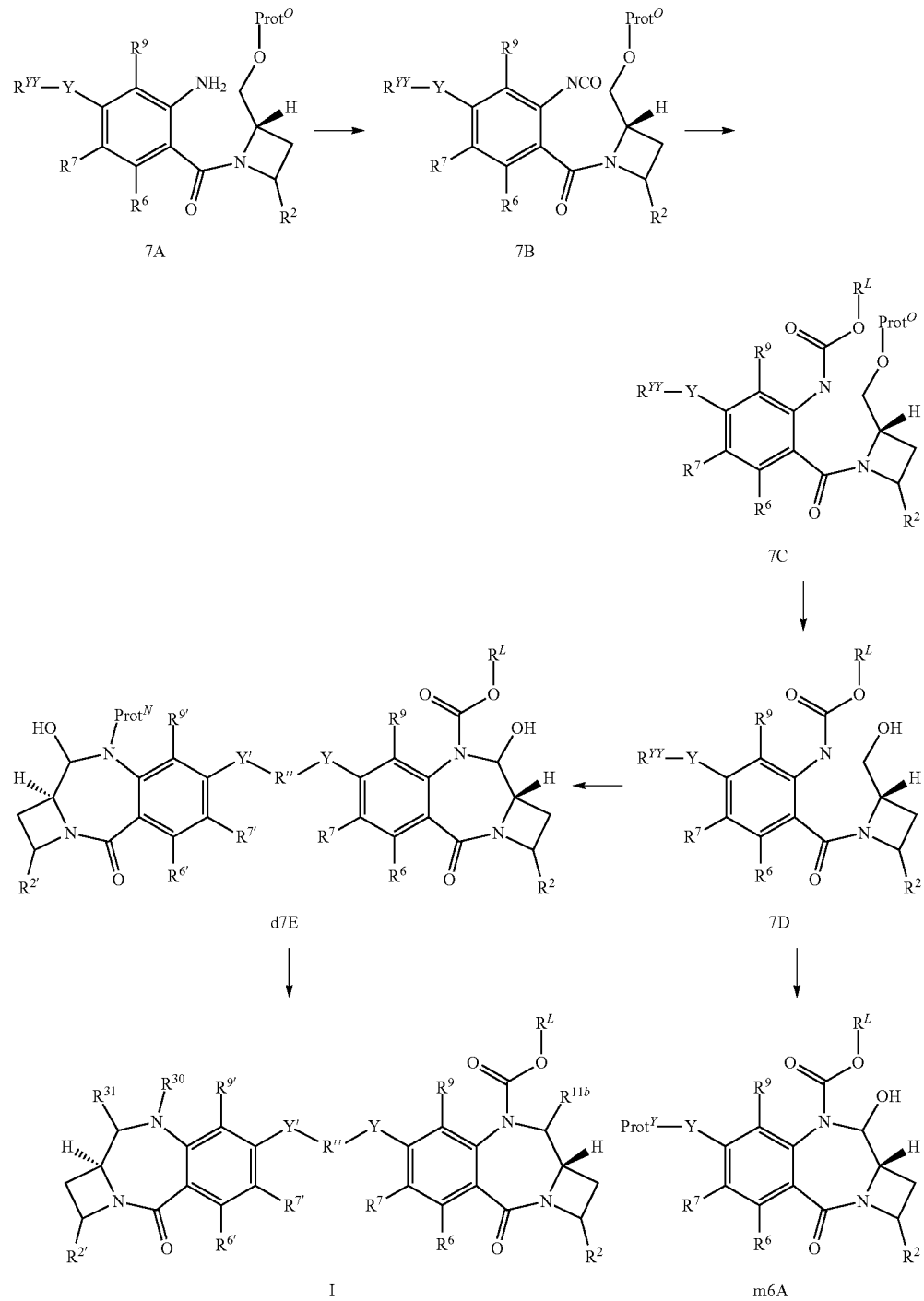

The compounds 7A, 7B, 7C and 70 may be dimeric (where the group $R^W$ represents R" connected to an ABD precursor singly protected at the N10 position) or monomeric (where the group $R^{YY}$ represents a suitable protecting group). Monomeric 7A is equivalent to monomeric 3C and can be synthesised via a similar route (as illustrated in Scheme 3).

The amine of 7A is transformed to isocyanate 7B. Strategies for isocyanate formation are detailed in the prior art (for example, WO 2005/023814). Typically, phosgene is used, preferably triphosgene under basic conditions; the solid triphosgene crystals are safer and easier to handle than toxic phosgene gas. The reaction should be carried out in an anhydrous and non-hydroxylic organic solvent, which is preferably non-polar. Suitable solvents include anhydrous DCM and anhydrous toluene. The reaction may be carried out at room temperature, and is conveniently monitored by infrared spectroscopy at about 2265 cm$^{-1}$.

The carbamate 7C is formed from the isocyanate via attack thereon by $R^L$—OH. The carbamate formation is often achieved via a one-pot-method, where the isocyanate is formed by triphosgene with TEA in DCM, and $R^L$—OH is added directly to the reaction mixture. This approach reduces the residence time of the isocyanate prior to carbamate formation, which lessens the chance of side reactions.

The Prot$^O$ protecting group is removed by a suitable method to provide the secondary alcohol 7D, typically under acidic conditions (e.g. Acetic acid in THF:Water solvent).

Oxidative ring closure of 7D via the aldehyde, or a functional equivalent, may be achieved by exposure to tetrapropylammoniumperruthenate (TPAP) in N-methyl-morpholine N-oxide (NMO) over molecular sieves, or by Swern oxidation (DMSO and oxalyl chloride), or preferably by Cu(I)/TEMPO radical oxidation (Tetrakisacetonitrile copper(I) triflate, 1-hydroxy-2,2,6,6-tetramethyl-piperidine (TEMPO), 1-methylimidazole and 2-(2-pyridyl)pyridine). This affords m6A (for further reaction in Scheme 6) for the monomeric 7D variant (i.e. where $R^{YY}$=Prot$^Y$), or affords d7E for the dimeric 7D variant (i.e. where $R^{YY}$=R" connected to a N10 protected ABD).

Removal of the nitrogen protecting group (Prot$^N$), typically Alloc removed with palladium, provides the asymmetrical compound of formula I.

An alternative route to the monomer m6A (Scheme 6) and the dimer d7E (Scheme 7) is illustrated in Scheme 8.

Scheme 8

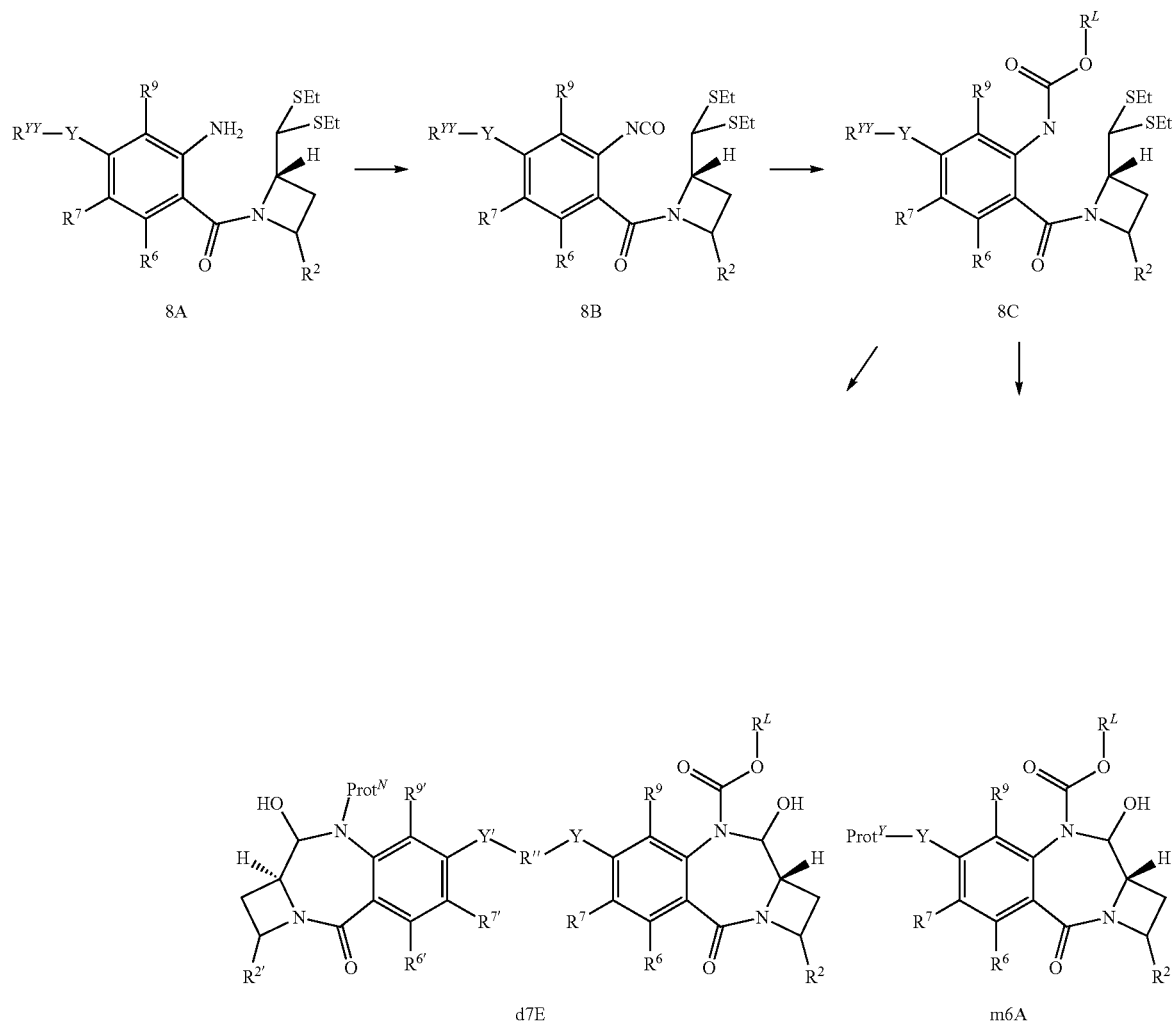

The compounds 8A, 8B and 8C may be dimeric (where the group R represents R" connected to an AD precursor singly protected at the N10 position) or monomeric (where the group $R^W$ represents a suitable protecting group, $Prot^Y$). 8A is transformed to isocyanate 8B, which in turn is reacted with $R^L$—OH to append $R^L$ by a carbamate. The preferred strategy is similar to that discussed in relation to Scheme 7.

Selective unmasking of the thioacetal 8C to the aldehyde results in spontaneous cyclisation of the B3-ring, by attack thereon by the singly protected N10 position. Typically, un-masking is mediated by Mercury(II), for example $HgCl_2$ with $CaCO_3$ in acetonitrile:water. The cyclisation provides monomeric m6A (from monomeric 8C) and dimeric d7E (from dimeric 8C). m6A may be reacted on as per Scheme 6, and d7E as per Scheme 7 to produce compounds of formula I.

The starting materials of Scheme 7 may be realised via a similar route to Scheme 3 (monomeric 3A to 3C) for monomeric 7A (i.e. where $R^{YY}$ is $Prot^Y$). Similarly, the starting materials of Scheme 8 may be realised via a similar route to Scheme 4 (monomeric 3A to 4C) for monomeric 8A (i.e. where $R^{YY}$ is $Prot^Y$).

A route to dimeric 7A and 8A (i.e. where $R^{YY}$ is R" connected to an ABD precursor singly protected at the N10 position) is illustrated in Scheme 9.

as described in Doronina et al., Nature Biotechnology, 2003, 21, 778-784). Briefly, antibodies (4-5 mg/mL) in PBS containing 50 mM sodium borate at pH 7.4 are reduced with tris(carboxyethyl)phosphine hydrochloride (TCEP) at 37° C. The progress of the reaction, which reduces interchain disulfides, is monitored by reaction with 5,5'-dithiobis(2-nitrobenzoic acid) and allowed to proceed until the desired level of thiols/mAb is achieved. The reduced antibody is then cooled to 0° C. and alkylated with 1.5 equivalents of maleimide drug-linker per antibody thiol. After 1 hour, the reaction is quenched by the addition of 5 equivalents of N-acetyl cysteine. Quenched drug-linker is removed by gel filtration over a PD-10 column. The ADC is then sterile-filtered through a 0.22 µm syringe filter. Protein concentration can be determined by spectral analysis at 280 nm and 329 nm, respectively, with correction for the contribution of drug absorbance at 280 nm. Size exclusion chromatography can be used to determine the extent of antibody aggregation, and RP-HPLC can be used to determine the levels of remaining NAC-quenched drug-linker.

Synthesis of Macrocyclic Embodiments

In some embodiments of the first, second and third aspects of the invention, the $R^7$ and $R^{7'}$ substituents may together Scheme 9

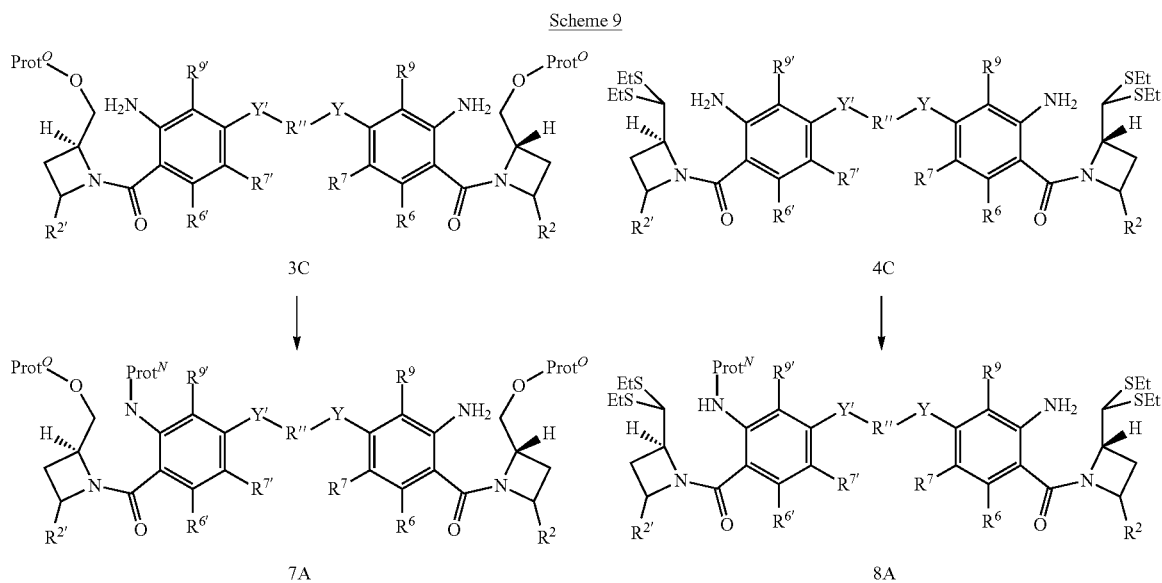

The dimeric variants of 3C and 4C are generated via the strategies discussed in Schemes 3, 4 and 5. 3C and 4C are protected at only one N10 position to yield the asymmetric ABD dimers 7A and 8A respectively. This is achieved by the addition of one equivalent of protecting reagent, typically allyl chloroformate when $Prot^N$ is Alloc, and subsequent purification to remove un-protected or doubly protected products.

Synthesis of Conjugates of Formula II

A possible step in the synthesis of the conjugates of the third aspect of the invention, particularly the constituent Drug Linker unit ($D^L$) of formula I, involves connection of the linker to a Ligand Unit, thereby converting the group $R^L$ (as per compounds of formula I) to the group $R^{LL}$ (as per compounds of formula I').

Conjugates can be prepared as previously described. Antibodies can be conjugated to the Drug Linker compound form a group which is: (i) —O—$(CH_2)_n$—O— where n is from 7 to 16, or (ii) —O—$(CH_2CH_2O)_m$— where m is from 2 to 5, to give a macrocyclic ABD dimer.

Various strategies may be employed to introduce a $R^7$-$R^{7'}$ linker, as illustrated in Scheme 10 below. Starting at d2D, where $R^7$ and $R^{7'}$ both represent —OR, the R group may be removed by addition of $BBr_3$ in DCM to reveal the alcohol. A substitution reaction of a dibromoalkane in base, such as 1,7-dribromoheptane with $K_2CO_3$, affords the macrocyclic product by attack thereon by both C7 position alcohols.

An alternative route starting at d2D involves substituting the C7 position alcohol with an n-bromoalk-1-ene. This provides two terminally unsaturated alkenyl chains, which can readily undergo ring-closing metathesis (RCM). For example, substitution may be achieved with 5-bromopent-1-ene and RCM with Grubs-II catalyst. Macrocyclisation via RCM is generally high yielding.

A preferred route to the macrocycle starts at dimeric 3A or an ester precursor, where $R^7$ and $R^{7'}$ both represent —OR. Removal of the R group and substitution by a dibromoalkane (using similar conditions as above) provides a macrocyclic compound. The ABD then may then be reached as per Schemes 3 or 4.

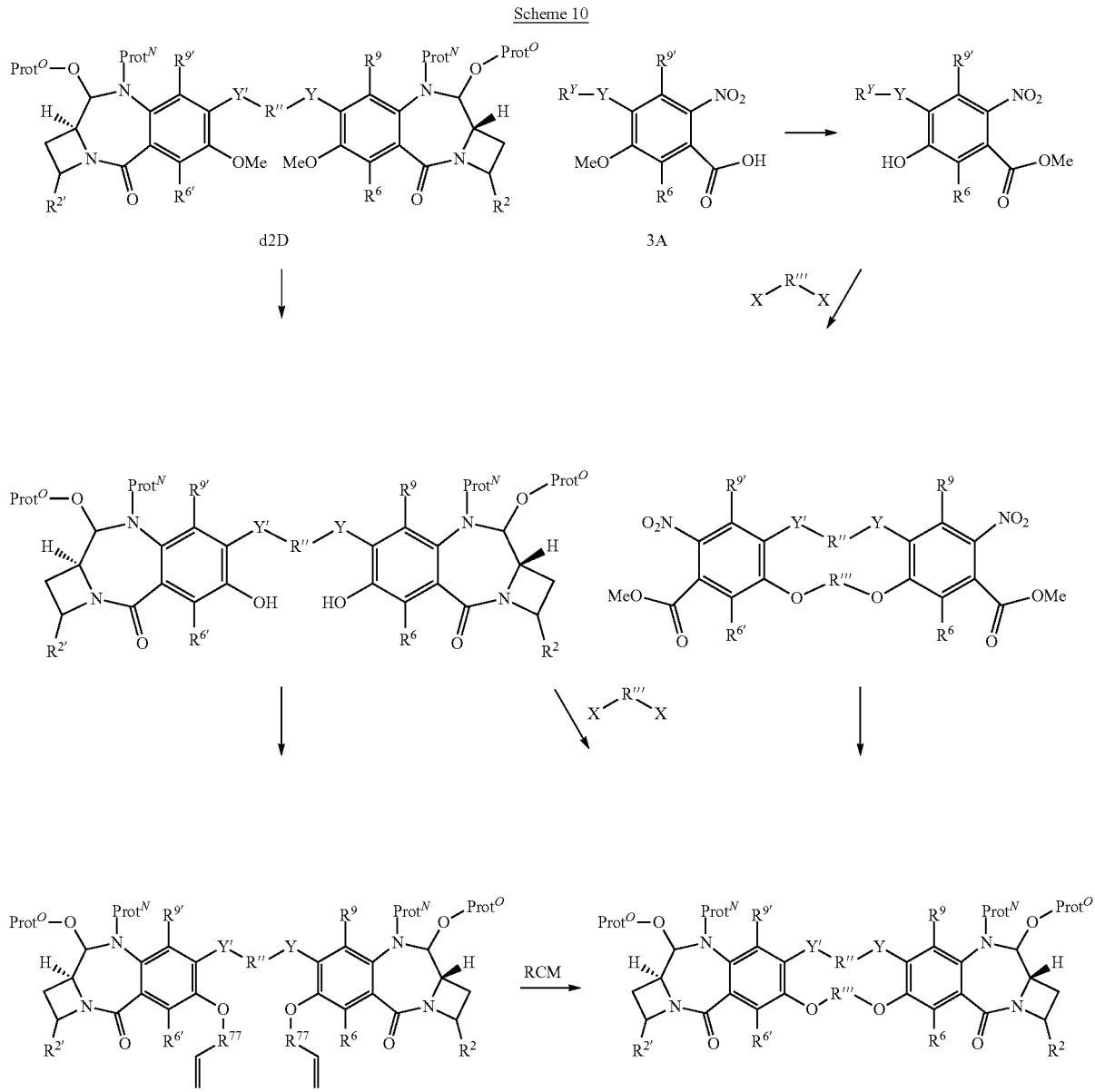

Scheme 10

The resulting product may be reacted on via Scheme 2 or Scheme 6 to achieve the compounds of formula IV and I respectively.

Further transformation details required to afford such macrocyclic products are available in the literature (Donnell, A. F., Zhang, Y., Stang, E. M., Wei, D. D., Tebben, A. J., Perez, H. L., Schroeder, G. M., Pan, C., Rao, C., Borzilleri, R. M., Vite, G. D., Gangwar, S., Macrocyclic pyrrolobenzodiazepine dimers as antibody-drug conjugate payloads, Bioorganic & Medicinal Chemistry Letters (2017), doi: https:H/doi.org/10.1016/j.bmcl.2017.10.028 and WO 2016/209951).

Synthesis of Secondary Amine Embodiments

Compounds where the N10-C11 group is —NH—CH$_2$— (i.e. secondary amines) may be synthesised by a modification of the above procedures. In particular, reductive amination of the compound 3B* can yield a modified version of m2A or d1A for use in the further steps:

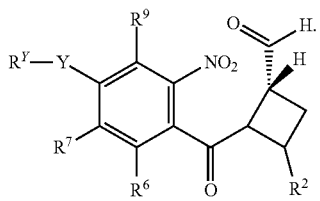

3B*

Compounds 3B* can be synthesised from a precursor alcohol by oxidation, the precursor alcohol being reachable by analogous steps to those used to synthesise 3B.

Synthesis of Drug Conjugates

Conjugates can be prepared as previously described. Antibodies can be conjugated to the Drug Linker compound as described in Doronina et al., Nature Biotechnology, 2003, 21, 778-784). Briefly, antibodies (4-5 mg/mL) in PBS containing 50 mM sodium borate at pH 7.4 are reduced with tris(carboxyethyl)phosphine hydrochloride (TCEP) at 37° C. The progress of the reaction, which reduces interchain disulfides, is monitored by reaction with 5,5'-dithiobis(2-nitrobenzoic acid) and allowed to proceed until the desired level of thiols/mAb is achieved. The reduced antibody is then cooled to 0° C. and alkylated with 1.5 equivalents of maleimide drug-linker per antibody thiol. After 1 hour, the reaction is quenched by the addition of 5 equivalents of N-acetyl cysteine. Quenched drug-linker is removed by gel filtration over a PD-10 column. The ADC is then sterile-filtered through a 0.22 μm syringe filter. Protein concentration can be determined by spectral analysis at 280 nm and 329 nm, respectively, with correction for the contribution of drug absorbance at 280 nm. Size exclusion chromatography can be used to determine the extent of antibody aggregation, and RP-HPLC can be used to determine the levels of remaining NAC-quenched drug-linker.

BRIEF DESCRIPTION OF THE FIGURES

FIG. 1 shows the effect on the growth of a tumour cell line when treated by a control or by a conjugate of the present invention.

FURTHER PREFERENCES

The following preferences may apply to all aspects of the invention as described above, or may relate to a single aspect. The preferences may be combined together in any combination.

$R^{6'}$ and $R^{9'}$ are selected from the same groups as $R^6$ and $R^9$ respectively. In some embodiments, $R^{6'}$, $R^{7'}$, $R^{9'}$, and Y' are the same as $R^6$, $R^7$, $R^9$, and Y respectively.

Dimer Link

In some embodiments, Y and Y' are both O.

In some embodiments, R" is a $C_{3-7}$ alkylene group with no substituents. In some of these embodiments, R" is a $C_3$, $C_5$ or $C_7$ alkylene. In particular, R" may be a $C_3$ or $C_5$ alkylene.

In other embodiments, R" is a group of formula:

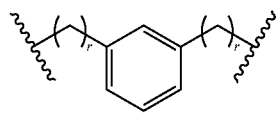

where r is 1 or 2.

The phenylene group may be replaced by a pyridylene group.

$R^6$ to $R^9$

In some embodiments, $R^9$ is H.

In some embodiments, $R^6$ is selected from H, OH, OR, SH, NH$_2$, nitro and halo, and may be selected from H or halo. In some of these embodiments $R^6$ is H.

In some embodiments, $R^7$ is selected from H, OH, OR, SH, SR, NH$_2$, NHR, NRR', and halo. In some of these embodiments $R^7$ is selected from H, OH and OR, where R is selected from optionally substituted $C_{1-7}$ alkyl, $C_{3-10}$ heterocyclyl and $C_{5-10}$ aryl groups. R may be more preferably a $C_{1-4}$ alkyl group, which may or may not be substituted. A substituent of interest is a $C_{5-6}$ aryl group (e.g. phenyl). Particularly preferred substituents at the 7-positions are OMe and OCH$_2$Ph. Other substituents of particular interest are dimethylamino (i.e. —NMe$_2$); —(OC$_2$H$_4$)$_q$OMe, where q is from 0 to 2; nitrogen-containing C heterocyclyls, including morpholino, piperidinyl and N-methyl-piperazinyl.

These embodiments and preferences apply to $R^{9'}$, $R^{6'}$ and $R^{7'}$ respectively.

In other embodiments, $R^7$ and $R^{7'}$ together form a group which is —O—(CH$_2$)$_n$—O—, where n is from 7 to 16. n may be at least 7, 8, 9, 10 or 11. N may be at most 16, 15, 14 or 13.

In other embodiments, $R^7$ and $R^{7'}$ together form a group which is —O—(CH$_2$CH$_2$O)$_m$—, where m is 2 to 5. m may be at least 2, 3 or 4. m may be at most 5, 4 or 3.

$R^{10}$, $R^{11}$, $R^{20}$, $R^{21}$ (Formula IV)

In some embodiments, $R^{10}$ and $R^{11}$ together form a double bond between the N and C atoms to which they are bound. In some of these embodiments, $R^{20}$ and $R^{21}$ together form a double bond between the N and C atoms to which they are bound. In other of these embodiments, $R^{20}$ and $R^{21}$ are both H.

In some embodiments, $R^{10}$ is H and $R^{11}$ is selected from OH and OR$^A$, where R$^A$ is $C_{1-4}$ alkyl. In some of these embodiments, $R^{20}$ is H and $R^{21}$ is selected from OH and OR$^B$, where R$^B$ is $C_{1-4}$ alkyl. In other of these embodiments, $R^{20}$ and $R^{21}$ are both H.

In some embodiments, $R^{10}$ and $R^{11}$ are both H. In some of these embodiments, $R^{20}$ and $R^{21}$ together form a double bond between the N and C atoms to which they are bound. In other of these embodiments, $R^{20}$ is H and $R^{21}$ is selected from OH and OR$^B$, where R$^B$ is $C_{1-4}$ alkyl.

In some embodiments, R$^A$ is methyl. In some embodiments, R$^B$ is methyl.

In some embodiments, only one of the pairs of $R^{10}$ and $R^{11}$ and $R^{20}$ and $R^{21}$ are both H. In other embodiments, neither of the pairs of $R^{10}$ and $R^{11}$ and $R^{20}$ and $R^{21}$ are both H.

In some embodiments, $R^{10}$, $R^{11}$, $R^{20}$ and $R^{21}$ are all H.

N10'-C11' (Formulae I and I*)

In some embodiments, $R^{30}$ and $R^{31}$ together form a double bond between the N and C atoms to which they are bound.

In some embodiments, $R^{30}$ is H and $R^{31}$ is selected from OH and $OR^B$, where $R^B$ is $O_{1-4}$ alkyl. In some of these embodiments, $R^B$ is methyl.

In some embodiments, $R^{30}$ is H and $R^{31}$ is H.

In some embodiments, $R^{31}$ is OH or $OR^B$, where $R^B$ is $C_{1-4}$ alkyl and $R^{30}$ is selected from:

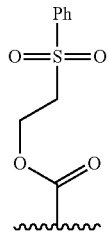 $R^{30a}$

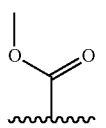 $R^{30b}$

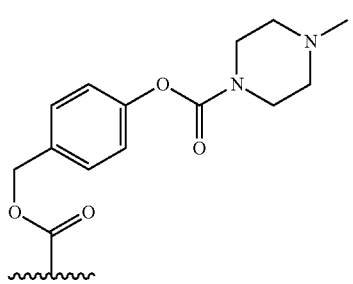 $R^{30c}$

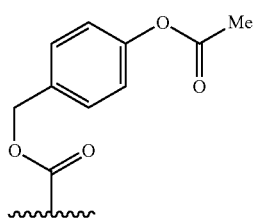 $R^{30d}$

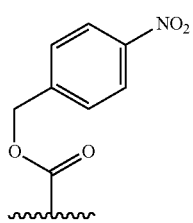 $R^{30e}$

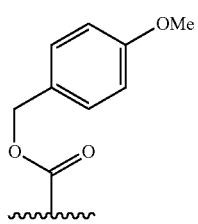 $R^{30f}$

-continued

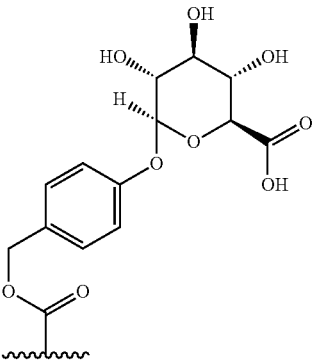 $R^{30g}$ $R^{30h}$

—C(=O)—X$_1$—NHC(=O)X$_2$—NH— represent a dipeptide. The amino acids in the dipeptide may be any combination of natural amino acids. The dipeptide may be the site of action for cathepsin-mediated cleavage.

In one embodiment, the dipeptide, —C(=O)—X$_1$—NHC(=O)X$_2$—NH—, is selected from:
-Phe-Lys-,
-Val-Ala-,
-Val-Lys-,
-Ala-Lys-,
-Val-Cit-,
-Phe-Cit-,
-Leu-Cit-,
-Ile-Cit-,
-Phe-Arg-,
-Trp-Cit-
where Cit is citrulline.

Preferably, the dipeptide, —C(=O)—X$_1$—NHC(=O)X$_2$—NH—, is selected from:
-Phe-Lys-,
-Val-Ala-,
-Val-Lys-,
-Ala-Lys-,
-Val-Cit-.

Most preferably, the dipeptide, —C(=O)—X$_1$—NHC(=O)X$_2$—NH—, is -Phe-Lys- or -Val-Ala-.

Other dipeptide combinations may be used, including those described by Dubowchik et al., *Bioconjugate Chemistry*, 2002, 13,855-869, which is incorporated herein by reference.

In one embodiment, the amino acid side chain is derivatised, where appropriate. For example, an amino group or carboxy group of an amino acid side chain may be derivatised.

In one embodiment, an amino group NH$_2$ of a side chain amino acid, such as lysine, is a derivatised form selected from the group consisting of NHR and NRR'.

In one embodiment, a carboxy group COOH of a side chain amino acid, such as aspartic acid, is a derivatised form selected from the group consisting of COOR, $CONH_2$, CONHR and CONRR'.

In one embodiment, the amino acid side chain is chemically protected, where appropriate. The side chain protecting group may be a group as discussed above. The present inventors have established that protected amino acid sequences are cleavable by enzymes. For example, it has been established that a dipeptide sequence comprising a Boc side chain-protected Lys residue is cleavable by cathepsin.

Protecting groups for the side chains of amino acids are well known in the art and are described in the Novabiochem Catalog. Additional protecting group strategies are set out in Protective Groups in Organic Synthesis, Greene and Wuts.

Possible side chain protecting groups are shown below for those amino acids having reactive side chain functionality:
Arg: Z, Mtr, Tos;
Asn: Trt, Xan;
Asp: Bzl, t-Bu;
Cys: Acm, Bzl, Bzl-OMe, Bzl-Me, Trt;
Glu: Bzl, t-Bu;
Gln: Trt, Xan;
His: Boc, Dnp, Tos, Trt;
Lys: Boc, Z—Cl, Fmoc, Z, Alloc;
Ser: Bzl, TBDMS, TBDPS;
Thr: Bz;
Trp: Boc;
Tyr: Bzl, Z, Z—Br.

In one embodiment, the side chain protection is selected to be orthogonal to a group provided as, or as part of, a capping group, where present. Thus, the removal of the side chain protecting group does not remove the capping group, or any protecting group functionality that is part of the capping group.

In other embodiments of the invention, the amino acids selected are those having no reactive side chain functionality. For example, the amino acids may be selected from: Ala, Gly, Ile, Leu, Met, Phe, Pro, and Val.

It is particularly preferred in the present invention, that if Q comprises a dipeptide, then —C(=O)—$X_1$—NHC(=O)$X_2$—NH— is the same dipeptide. An example of a preferred group is:

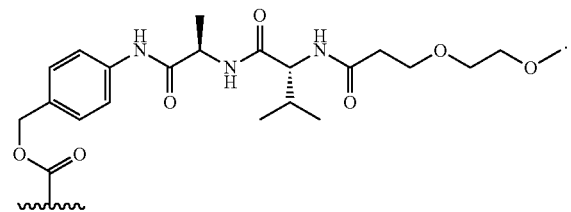 [SMILES: *C(=O)OCc1ccc(NC(=O)[C@@H](C)NC(=O)[C@H](NC(=O)CCOCCOC)C(C)C)cc1]

Other preferred $R^{30}$ groups include:

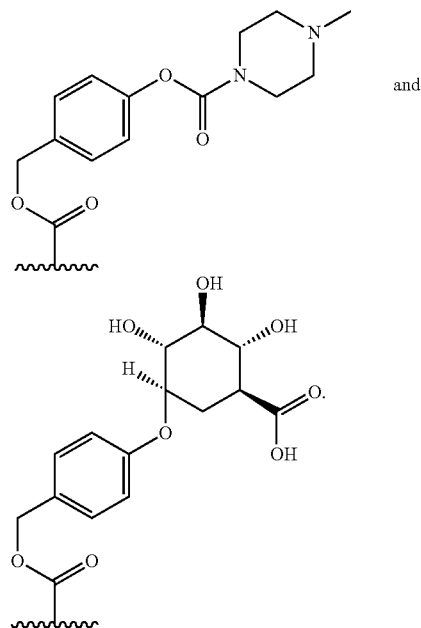

$R^{11b}$ (Formulae I and I*)

In some embodiments, $R^{11b}$ is OH.

In some embodiments, $R^{11b}$ is $OR^A$, where $R^A$ is $C_{1-4}$ alkyl. In some of these embodiments, $R^A$ is methyl.

Further Formulae

In some embodiments of the first aspect of the present invention are of formulae Va, IVb or IVc:

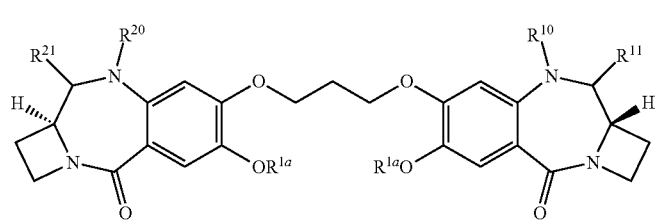

IVa

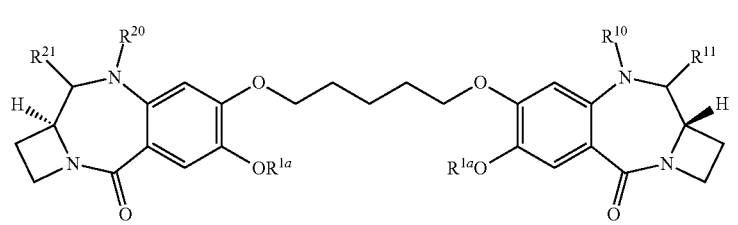

IVb

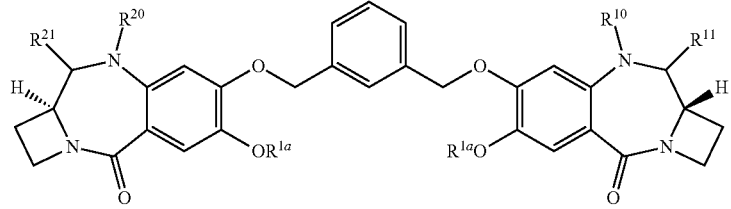
IVc
where R$^{1a}$ is selected from methyl and benzyl;
R$^{10}$, R$^{11}$, R$^{20}$ and R$^{21}$ are as defined above.
In some embodiments of the second aspect of the present invention are of formulae Ia, Ib or Ic:
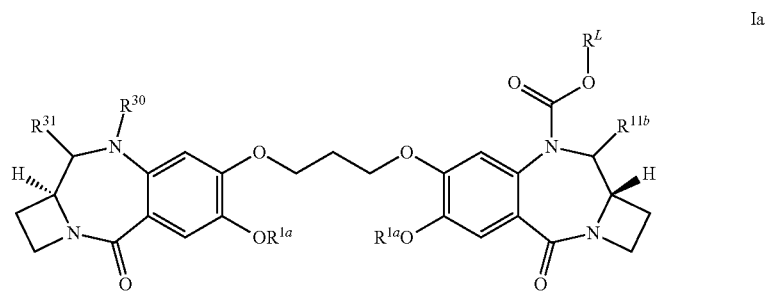
Ia
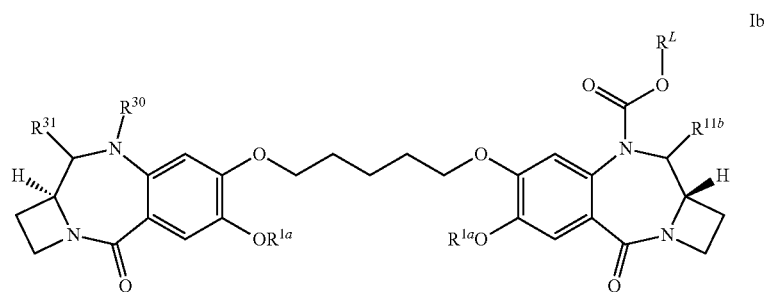
Ib
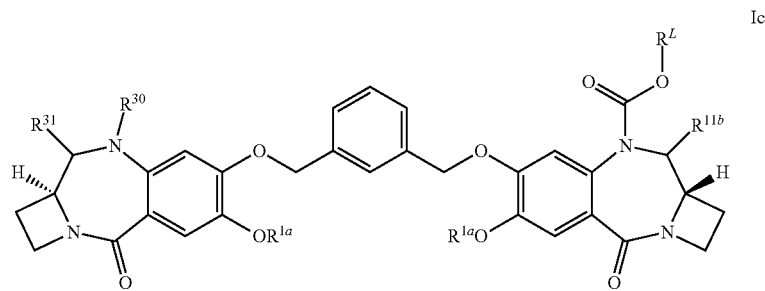
Ic where $R^{1a}$ is selected from methyl and benzyl;

$R^{30}$, $R^{31}$, $R^L$ an $R^{11b}$ are as defined above.

These embodiments and preferences also apply to the third aspect of the invention.

Linker ($R^L$)

In some embodiments, $R^L$ is a formula IIIa.

In some embodiments, $R^{LL}$ is a formula IIIa'.

$G^L$ $G^L$ may be selected from

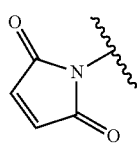 ($G^{L1-1}$)

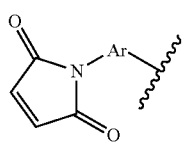 ($G^{L1-2}$)

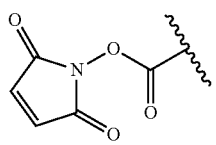 ($G^{L2}$)

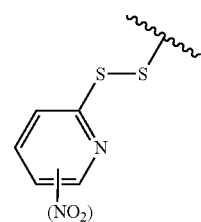 ($G^{L3-1}$)

where the $NO_2$ group is optional

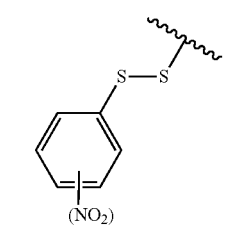 ($G^{L3-2}$)

where the $NO_2$ group is optional

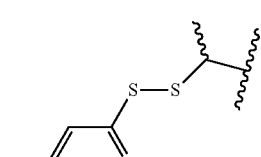 ($G^{L3-3}$)

where the $NO_2$ group is optional

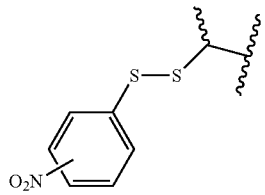 ($G^{L3-4}$)

where the $NO_2$ group is optional

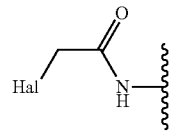 ($G^{L4}$)

Where Hal = I, Br, Cl

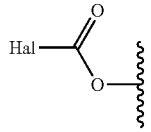 ($G^{L5}$)

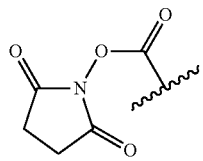 ($G^{L6}$)

 ($G^{L7}$)

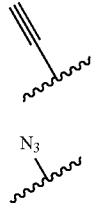 ($G^{L8}$)

($G^{L9}$)

where Ar represents a $C_{5-6}$ arylene group, e.g. phenylene.

In some embodiments, $G^L$ is selected from $G^{L1-1}$ and $G^{L1-2}$. In some of these embodiments, $G^L$ is $G^{L1-1}$.

$G^{LL}$ $G^{LL}$ ma be selected from:

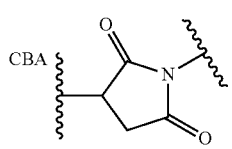 ($G^{LL1-1}$)

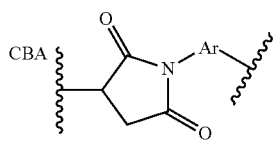 ($G^{LL1-2}$)

(G^{LL2}) 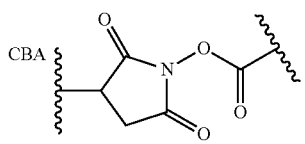

(G^{LL3-1}) 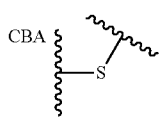

(G^{LL3-2}) 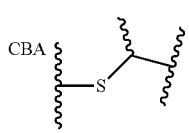

(G^{LL4}) 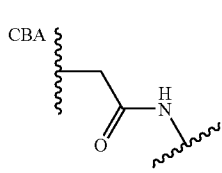

(G^{LL5}) 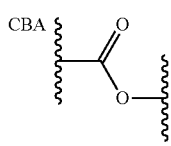

(G^{LL6}) 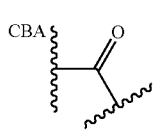

(G^{LL7}) 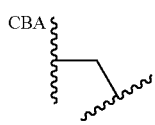

(G^{LL8-1}) 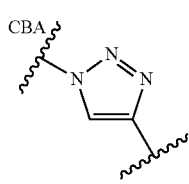

(G^{LL8-2}) 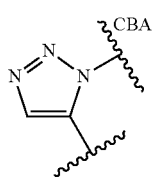

(G^{LL9-1}) 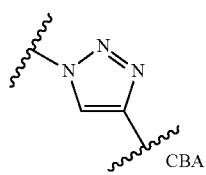

(G^{LL9-2}) 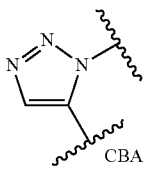

where Ar represents a $C_{5-6}$ arylene group, e.g. phenylene.

In some embodiments, $G^{LL}$ is selected from $G^{LL1-1}$ and $G^{LL1-2}$. In some of these embodiments, $G^{LL}$ is $G^{LL1-1}$.

X

X is:

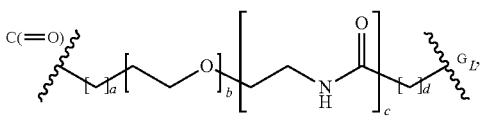

where a=0 to 5, b=0 to 16, c=0 or 1, d=0 to 5.

a may be 0, 1, 2, 3, 4 or 5. In some embodiments, a is 0 to 3. In some of these embodiments, a is 0 or 1. In further embodiments, a is 0.

b may be 0, 1, 2, 3, 4, 5, 6, 7, 8, 9, 10, 11, 12, 13, 14, 15 or 16. In some embodiments, b is 0 to 12. In some of these embodiments, b is 0 to 8, and may be 0, 2, 4 or 8.

c may be 0 or 1.

d may be 0, 1, 2, 3, 4 or 5. In some embodiments, d is 0 to 3. In some of these embodiments, d is 1 or 2. In further embodiments, d is 2.

In some embodiments of X, a is 0, c is 1 and d is 2, and b may be from 0 to 8. In some of these embodiments, b is 0, 4 or 8.

Q

In one embodiment, Q is an amino acid residue. The amino acid may a natural amino acids or a non-natural amino acid.

In one embodiment, Q is selected from: Phe, Lys, Val, Ala, Cit, Leu, Ile, Arg, and Trp, where Cit is citrulline.

In one embodiment, Q comprises a dipeptide residue. The amino acids in the dipeptide may be any combination of natural amino acids and non-natural amino acids. In some embodiments, the dipeptide comprises natural amino acids. Where the linker is a cathepsin labile linker, the dipeptide is the site of action for cathepsin-mediated cleavage. The dipeptide then is a recognition site for cathepsin.

In one embodiment, Q is selected from:
$^{CO}$-Phe-Lys-$^{NH}$,
$^{CO}$-Val-Ala-$^{NH}$,
$^{CO}$-Val-Lys-$^{NH}$,
$^{CO}$-Ala-Lys-$^{NH}$,
$^{CO}$-Val-Cit-$^{NH}$,
$^{CO}$-Phe-Cit-$^{NH}$,
$^{CO}$-Leu-Cit-$^{NH}$,
$^{CO}$-Ile-Cit-$^{NH}$,
$^{CO}$-Phe-Arg-$^{NH}$, and
$^{CO}$-Trp-Cit-$^{NH}$;
where Cit is citrulline.

Preferably, Q is Selected from:
$^{CO}$-Phe-Lys-$^{NH}$,
$^{CO}$-Val-Ala-$^{NH}$,
$^{CO}$-Val-Lys-$^{NH}$, $^{CO}$-Ala-Lys-$^{NH}$,
$^{CO}$-Val-Cit-$^{NH}$.

Most preferably, Q is selected from $^{CO}$-Phe-Lys-$^{NH}$, $^{CO}$-Val-Cit-$^{NH}$ and $^{CO}$-Val-Ala-$^{NH}$.

Other Dipeptide Combinations of Interest Include:
$^{CO}$-Gly-Gly-$^{NH}$,
$^{CO}$-Pro-Pro-$^{NH}$, and
$^{CO}$-Val-Glu-$^{NH}$.

Other dipeptide combinations may be used, including those described by Dubowchik et al., *Bioconjugate Chemistry*, 2002, 13,855-869, which is incorporated herein by reference.

In some embodiments, $Q^X$ is a tripeptide residue. The amino acids in the tripeptide may be any combination of natural amino acids and non-natural amino acids. In some embodiments, the tripeptide comprises natural amino acids. Where the linker is a cathepsin labile linker, the tripeptide is the site of action for cathepsin-mediated cleavage. The tripeptide then is a recognition site for cathepsin. Tripeptide linkers of particular interest are:
$^{CO}$-Glu-Val-Ala-$^{NH}$
$^{CO}$-Glu-Val-Cit-$^{NH}$
$^{CO}$-αGlu-Val-Ala-$^{NH}$
$^{CO}$-αGlu-Val-Cit-$^{NH}$ In one embodiment, the amino acid side chain is chemically protected, where appropriate. The side chain protecting group may be a group as discussed below. Protected amino acid sequences are cleavable by enzymes. For example, a dipeptide sequence comprising a Boc side chain-protected Lys residue is cleavable by cathepsin.

Protecting groups for the side chains of amino acids are well known in the art and are described in the Novabiochem Catalog, and as described above.

In some embodiments, $R^L$ is of formula IIIb.
In some embodiments, $R^{LL}$ is of formula IIIb'.
$R^{L1}$ and $R^{L2}$ are independently selected from H and methyl, or together with the carbon atom to which they are bound form a cyclopropylene or cyclobutylene group.
In some embodiments, both $R^{L1}$ and $R^{L2}$ are H.
In some embodiments, $R^{L1}$ is H and $R^{L2}$ is methyl.
In some embodiments, both $R^{L1}$ and $R^{L2}$ are methyl.
In some embodiments, $R^{L1}$ and $R^{L2}$ together with the carbon atom to which they are bound form a cyclopropylene group.
In some embodiments, $R^{L1}$ and $R^{L2}$ together with the carbon atom to which they are bound form a cyclobutylene group.

In the group IIIb, in some embodiments, e is 0. In other embodiments, e is 1 and the nitro group may be in any available position of the ring. In some of these embodiments, it is in the ortho position. In others of these embodiments, it is in the para position.

In one particular embodiment, the second aspect of the invention comprises a compound of formula Id:

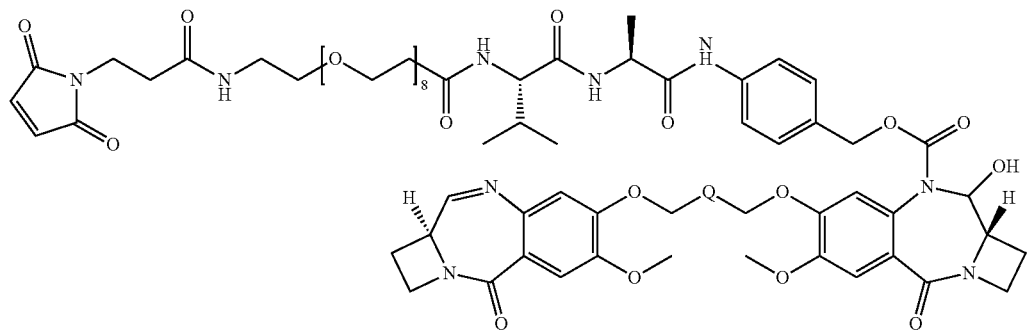

(Id)

where Q is selected from:
(a) —CH$_2$—;
(b) —C$_3$H$_6$—; and (c)

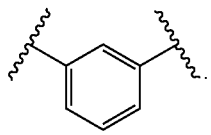

In one particular embodiment, the third aspect of the invention, the Drug linker (D$^L$) is of formula (Id'):

(I*d)

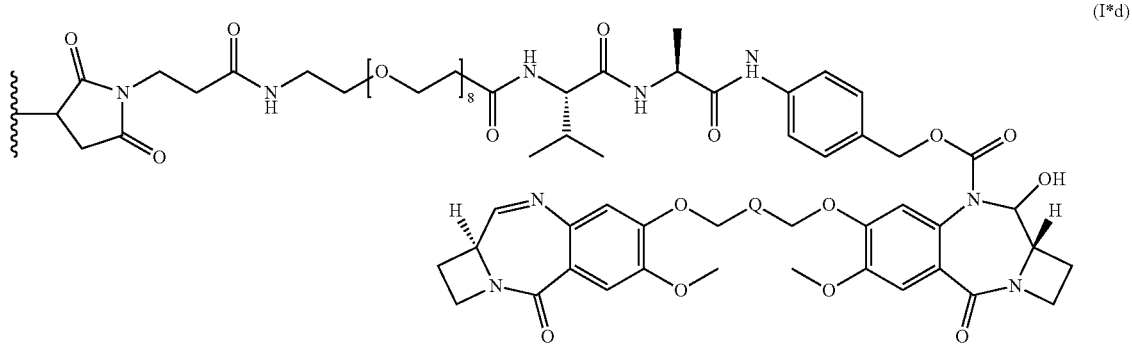

where Q is selected from:
(a) —CH$_2$—;
(b) —C$_3$H$_6$—; and (c)

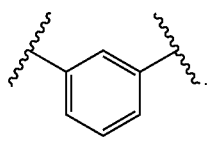

In some embodiments of the present invention, the C11 substituent may be in the following stereochemical arrangement relative to neighbouring groups:

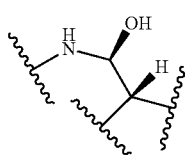

In other embodiments, the C11 substituent may be in the following stereochemical arrangement relative to neighbouring groups:

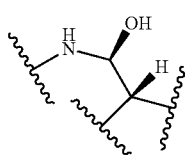

EXAMPLES

General Information

Manual flash chromatography was performed using Merck Kieselgel 60 F254 silica gel. Extraction and chromatography solvents were bought and used without further purification from Fisher Scientific, U.K. All chemicals were purchased from Aldrich, Lancaster or BDH. Automated flash chromatography was performed using a Biotage Isolera 1™ using gradient elution starting from either 88% hexane/EtOAc or 99.9% DCM/MeOH until all UV active components (detection at 214 and 254 nm) eluted from the column. The gradient was manually held whenever substantial elution of UV active material was observed. Fractions were checked for purity using thin-layer chromatography (TLC) using Merck Kieselgel 60 F254 silica gel, with fluorescent indicator on aluminium plates. Visualisation of TLC was achieved with UV light or iodine vapour unless otherwise stated. Extraction and chromatography solvents were bought and used without further purification from VWR U.K. All fine chemicals were purchased from Sigma-Aldrich or TCI Europe unless otherwise stated. Pegylated reagents were obtained from Quanta biodesign US via Stratech UK.

The LC/MS Conditions were as Follow:

Positive mode electrospray mass spectrometry was performed using a Waters Aquity H-class. Mobile phases used were solvent A (water with 0.1% formic acid) and solvent B (acetonitrile with 0.1% formic acid).

LCMS 3 min: initial composition was 5% B held over 0.25 min, then increase from 5% B to 100% B over a 2 min period. The composition was held for 0.50 min at 100% B, then returned to 5% B in 0.05 minutes and hold there for 0.05 min. Total gradient run time equals 3 min. Flow rate 0.8 mL/min. Detection was at 254 nm. Columns: Waters Acquity UPLC® BEH Shield RP18 1.7 μm 2.1×50 mm at 50° C. fitted with Waters Acquity UPLC® BEH Shield RP18 VanGuard Pre-column, 130A, 1.7 μm, 2.1 mm×5 mm.

LCMS 15 min: initial composition 5% B held over 1 min, then increase from 5% B to 100% B over a 9 min period. The composition was held for 2 min at 100% B, then returned to 5% B in 0.10 minutes and hold there for 3 min. Total gradient run time equals 15 min. Flow rate 0.6 mL/min. Wavelength detection range: 190 to 800 nm. Oven temperature: 50° C. Column: ACE Excel 2 C18-AR, 2μ, 3.0×100 mm.

Preparative HPLC:

Reverse-phase ultra-fast high-performance liquid chromatography (UFLC) was carried out on a Shimazdzu Prominence® machine using a Phenomenex® Gemini NX 5μ C18 column (at 50° C.) dimensions: 150×21.2 mm. Eluents used were solvent A (H₂O with 0.1% formic acid) and solvent B (CH₃CN with 0.1% formic acid). All UFLC experiments were performed with gradient conditions: Initial composition 13% B increased to 60% B over a 15 minute period then increased to 100% B over 2 minutes. The composition was held for 1 minute at 100% B, then returned to 13% B in 0.1 minute and held there for 1.9 minutes. The total duration of the gradient run was 20.0 minutes. Flow rate was 20.0 mL/minute and detection was at 254 and 280 nm.

Example 1

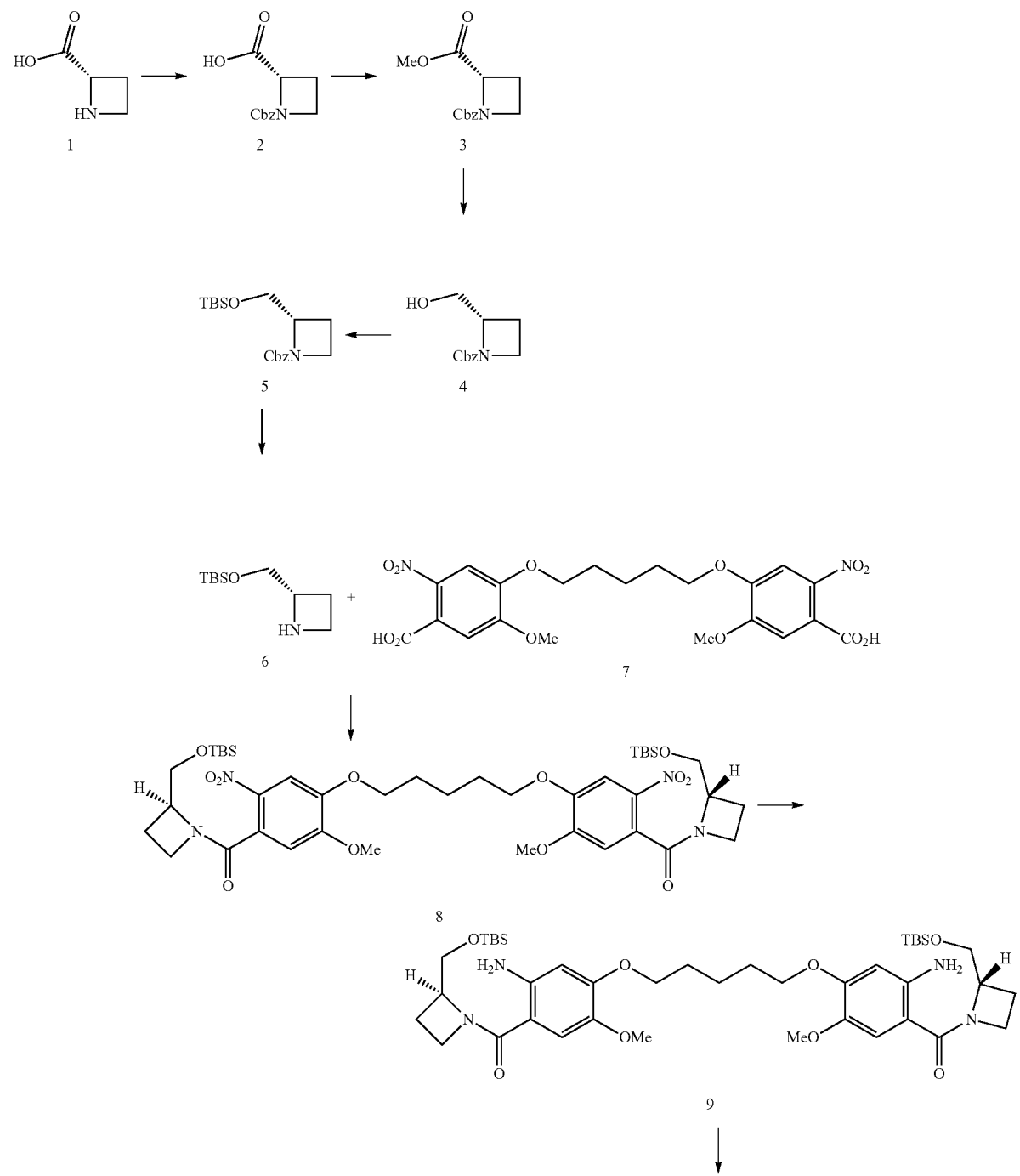

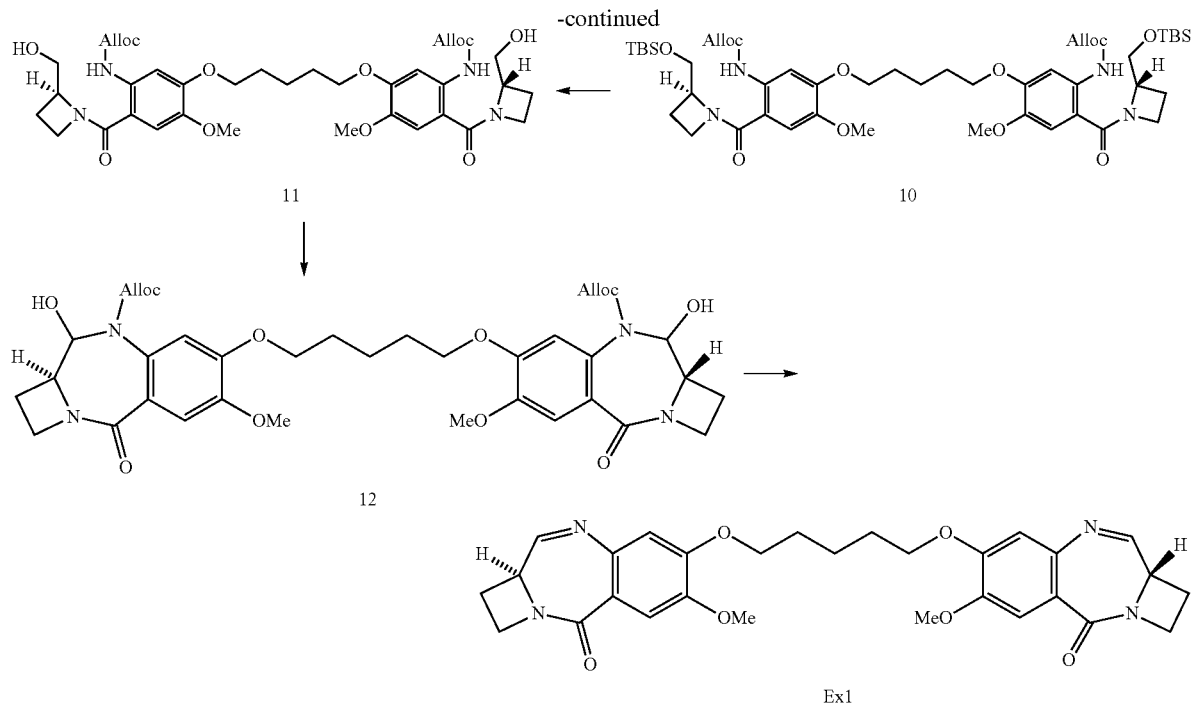

a) 1-((benzyloxy)carbonyl)azetidine-2-carboxylic Acid (2)

(2S)-Azetidine-2-carboxylic acid 1 (3 g, 29.674 mmol) and sodium bicarbonate (6.3 g, 75 mmol) were solubilised in $H_2O$ (25 mL, 1387.75 mmol) and N-(benzyloxycarbonyl) succinimide (8.5 g, 34 mmol) in THF (25 mL, 307 mmol, 100 mass %) were added dropwise. After stirring at room temperature for 12 h, the two phases were allowed to separate. The aqueous phase was washed with diethyl ether (50 mL), cooled in an ice bath, and then acidified to pH=2 with conc. HCl. The aqueous layer was extracted with ethyl acetate (2×50 mL) and the combined organic extracts were dried ($MgSO_4$) and the excess solvent evaporated in vacuo to give crude product as a clear oil. The crude material was used without purification in the next step. LCMS 3 min: $ES^+$=1.34 min, m/z 258.2 $[M+Na]^+$.

b) (1-benzyl 2-methyl (S)-azetidine-1,2-dicarboxylate (3)

In a dry round bottom flask, (2S)-1-benzyloxycarbonylazetidine-2-carboxylic acid 2 (6.98 g, 29.7 mmol) was solubilised in MeOH (65 mL) and sulfuric acid (3 mL) was added. The mixture was heated to reflux and left to stir overnight. The mixture was left to cool down to r.t. and quenched with $Net_3$ (to pH=7) before being stirred for 1 h. Methanol was removed in vacuo. The residue was taken up in EtOAc, washed with $H_2O$ and brine before being dried with $MgSO_4$ and filtered. The organics were removed in vacuo to give crude product 3 (8.004 g, 32.11 mmol) as a clear oil. LCMS 3 min: $ES^+$=1.53 min, m/z no ionisation c) Benzyl (S)-2-(hydroxymethyl)azetidine-1-carboxylate (4)

O1-benzyl O2-methyl (2S)-azetidine-1,2-dicarboxylate 3 (7.6 g, 30 mMol) was solubilised in THF (75 mL, 922 mmol), cooled to 0° C. and $LiBH_4$ (1 g, 45 mMol,) was added. The mixture was allowed to warm to r.t. and stirred for a further hour at which point the reaction is complete. The reaction mixture was cooled to 0° C. before being quench with $H_2O$ and 1M HCl. The volatiles were removed in vacuo. The residue was taken up in EtOAc and washed with brine (2×50 mL), dried with $MgSO_4$, filtered and the solvent removed by rotary evaporation under reduced pressure. Purification by silica gel column chromatography (Hex/EtOAc, 100% to 1:2) afforded product a 4 as a clear oil (4.076 g, 60% yield over 3 steps). LCMS 3 min: $ES^+$=1.36 min, m/z 222.3 $[M+H]^+$.

d) Benzyl (S)-2-(((tert-butyldimethylsilyl)oxy)methyl) azetidine-1-carboxylate (5)

Benzyl (2S)-2-(hydroxymethyl)azetidine-1-carboxylate 4 (4.0766 g, 18.425 mmol) was solubilised in dry $CH_2Cl_2$ (20 mL, 312.0 mmol) and the mixture was cooled to 0° C. before adding imidazole (2.508 g, 36.84 mmol) and TBS-Cl (4.16 g, 27.6 mmol). The mixture was allowed to warm to room temperature and left to stir. LCMS shows reaction was complete within 5 min. The organics were washed with sat. $NH_4Cl$, water, brine, dried with $MgSO_4$, filtered and the volatiles removed in vacuo. Purification by silica gel column chromatography (Hex/EtOAc, 100% to 9:1) afforded product a 5 (6.90 g, not completely dry, quantitative). LCMS 3 min: $ES^+$=2.15 min, m/z 336.9 $[M+H]^+$.

e) (S)-2-(((tert-butyldimethylsilyl)oxy)methyl)azetidine (6)

Palladium on carbon (10%) (100 mg, 0.93 mMol) was treated with EtOAc (5 mL) dropwise and the resulting slurry added to a suspension of 5 (6.9027 g, 20.57 mmol) in EtOH (100 mL) at room temperature in a Parr hydrogenation bottle. The reaction mixture was subjected to $H_2$ gas at 20 psi then the bottle was evacuated under vacuum (repeated 3 times). The bottle was then topped up to 38 psi $H_2$ and shaken for 1 hour. The pressure dropped to ~30 psi during this time and the bottle was topped up again to 40 psi and shaken for a further hour. No further decreases in pressure were observed and the reaction was deemed complete. This was confirmed by LC-MS. The mixture was filtered through celite and the filtrate evaporated in vacuo to provide the crude product 6 as a brown oil (3.761 g, 90% yield). LCMS 3 min: $ES^+$=1.70 min, m/z no ionisation.

f) ((S)-2-(((Tert-butyldimethylsilyl)oxy)methyl)azetidin-1-yl)(4-(6-(4-((2R)-2-(((tert-butyldimethylsilyl)oxy)methyl)cyclobutane-1-carbonyl)-2-methoxy-5-nitrophenoxy)hexyl)-5-methoxy-2-nitrophenyl)methanone (8)

DCC (3.8 g, 18 mmol) was added to a solution of 7 (3.9 g, 7.9 mMol) and HOBt (2.3 g, 17 mMol) in $CH_2Cl_2$ (200 mL) at 0° C. The cold bath was removed and the reaction was allowed to proceed for 30 min at room temperature, at which time a solution of 6 (3.65 g, 18 mMol) and triethylamine (3.2 mL, 23 mmol) in $CH_2Cl_2$ (200 mL) was added rapidly at −10° C. under argon The reaction mixture was allowed to stir at room temperature and monitored by LC/MS. After 2 min, the reaction was complete. The solids were removed by filtration over celite and the organic phase was washed with cold aqueous 0.1 M HCl until the pH was measured at 2. The organic phase was then washed with water, followed by saturated aqueous sodium bicarbonate, brine, dried with $MgSO_4$, filtered and vacced down under reduced pressure. Purification by silica gel column chromatography (Hex/EtOAc/$CH_2Cl_2$, 100% to 1:2:1) afforded product 8 (5.9 g, 87% yield). The product is contaminated with some mono-coupled product (impurity does not separate upon chromatography). LCMS 3 min: $ES^+$=2.35 min, m/z 862.2 $[M+H]^+$.

g) ((Pentane-1,5-diylbis(oxy))bis(2-amino-5-methoxy-4,1-phenylene))bis(((S)-2-(((tert-butyldimethylsilyl)oxy)methyl)azetidin-1-yl)methanone) (9)

Zinc (4.65 g, 71.1 mmol) was slowly added to a solution of 8 (2.45 g, 2.85 mmol) in a mixture of MeOH/$H_2O$/formic acid 90:5:5 (66 mL). The resulting exotherm was controlled using an ice bath to maintain the temperature of the reaction mixture below 40° C. Upon completion, the solids were removed by filtration over celite and the organic phase was washed with water and brine before being dried with $MgSO_4$, filtered and the volatiles removed under reduced pressure. Crude material 9 (2.28 g, quantitative) was used as such in the next step. LCMS 3 min: $ES^+$=2.32 min, m/z 802.3 $[M+H]^+$.

h) Diallyl ((pentane-1,5-diylbis(oxy))bis(6-((S)-2-(((tert-butyldimethylsilyl)oxy)methyl)azetidine-1-carbonyl)-4-methoxy-3,1-phenylene))dicarbamate (10)

Compound 9 (2.23 g, 2.78 mmol) was solubilised in $CH_2Cl_2$ (50 mL) under an argon atmosphere. The mixture was cooled to −78° C. before pyridine (0.99 mL, 12.3 mMol) and allyl chloroformate (0.738 mL, 2.49 mmol) were added. The reaction was left to stir at −78° C. for 10 min before being allowed to warm up to room temp. After 15 min the reaction was complete. The organics were washed with sat. $CuSO_4$, $H_2O$, brine before being dried with $MgSO_4$, filtered and the volatiles removed under reduced pressure. Crude product 10 (1.47 g, 1.52 mMol, quantitative) was used as such in the next step. LCMS 3 min: $ES^+$=2.53 min, m/z 970.3 $[M+H]^+$.

i) Diallyl ((pentane-1,5-diylbis(oxy))bis(6-((S)-2-(hydroxymethyl)azetidine-1-carbonyl)-4-methoxy-3,1-phenylene))dicarbamate (11)

Compound 10 (1.47 g, 1.52 mMol) was solubilised in a 3:1:1 mixture of $H_2O$/THF/acetic acid (16 mL) and the reaction was left to stir over the weekend. The mixture was extracted with $CH_2Cl_2$ and washed with sat. $NaHCO_3$, $H_2O$ and brine before being dried with $MgSO_4$, filtered and the volatiles removed under reduced pressure. Purification by silica gel column chromatography (Hex/EtOAc, 100% to 1:1) afforded product 11 (859 mg, 76.5% Yield) as a clear oil. LCMS 3 min: $ES^+$=1.75 min, m/z 742.0 $[M+H]^+$.

j) Diallyl 7,7'-(pentane-1,5-diylbis(oxy))(10aS,10a'S)-bis(10-hydroxy-6-methoxy-4-oxo-1,2,10,10a-tetrahydroazeto[1,2-a]benzo[e][1,4]diazepine-9(4H)-carboxylate) (12)

Compound 11 (850 mg, 1.14 mMol) was solubilised in $CH_2Cl_2$ (60 mL). 1-hydroxy-2,2,6,6-tetramethyl-piperidine; 1-methylimidazole; 2-(2-pyridyl)pyridine (0.7 mL, 1140 mmol, 0.2 mMl/L) and tetrakisacetonitrile copper(I) triflate (55 mg, 0.145 mMol) were subsequently added ant the mixture stirred at 35° C. with 2 balloon of air pressing in. The reaction was left to stir overnight before being vacuumed to dryness in a rotary evaporator. Purification by silica gel column chromatography ($CHCl_3$/MeOH, 100% to 95:5) afforded product 12 (346 g, 0.47 mMol, 41% yield). LCMS 3 min: $ES^+$=1.48 min, m/z 737.9 $[M+H]^+$.

k) (10aS,10a'S)-7,7'-(pentane-1,5-diylbis(oxy))bis(6-methoxy-1,10a-dihydroazeto[1,2-a]benzo[e][1,4]diazepin-4(2H)-one) (Ex1)

Compound 12 (335 mg, 0.45 mmol) was solubilised in $CH_2Cl_2$ (20 mL) in a flask under Argon. Pyrrolidine (650 μL, 7.8 mMol) and Pd(PPh$_3$)$_4$ (50 mg, 0.004 mMol) were subsequently added and the mixture left to stir at r.t until complete. The organics were washed with sat. $NH_4Cl$, $H_2O$ and brine before being dried with $MgSO_4$, filtered and the volatiles removed under reduced pressure. Purification by isolera chromatography ($CH_2Cl_2$/($CH_2Cl_2$+10% MeOH) 92:7 to 10:90. Two fractions containing the product were isolate but with insufficient purity. The fractions were combined and repurified by manual chromatography and pure product Ex1 was isolated (146 mg, 0.27 mMol, 24% yield).

LCMS 3 min: $ES^+$=1.32 min, m/z 533.8 $[M+H]^+$. LCMS 15 min: $ES^+$=4.83 min, m/z 533.9 $[M+H]^+$.

69
Example 2
70
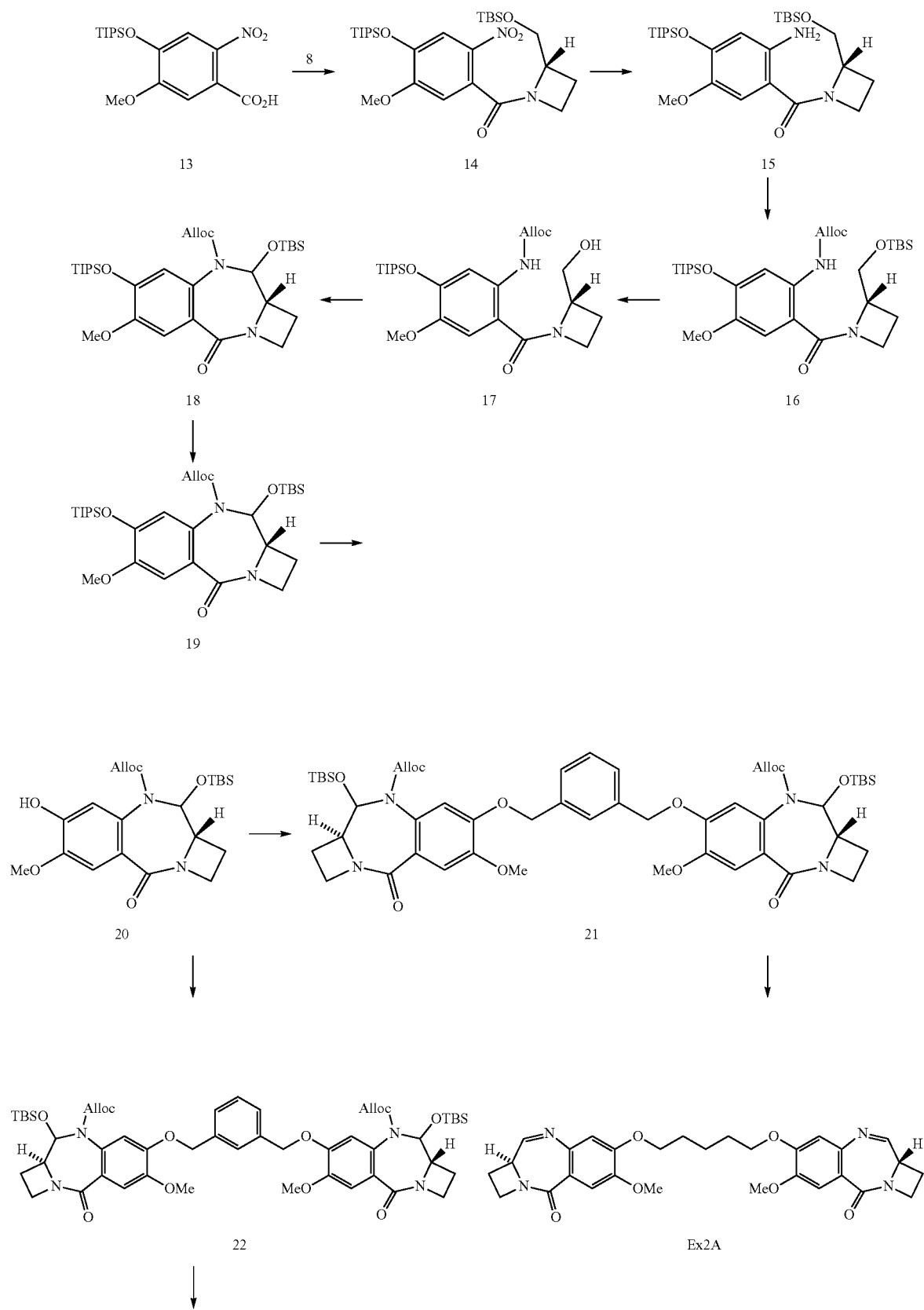

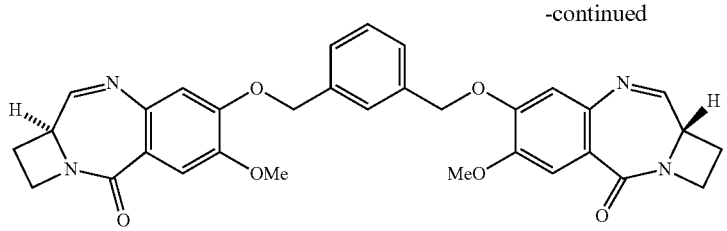

Ex2B a) ((S)-(2-(((tert-butyldimethylsilyl)oxy)methyl) azetidin-1-yl)(5-methoxy-2-nitro-4-((triisopropylsilyl)oxy)phenyl)methanone (13)

DCC (4.021 g, 19.49 mmol) was added to a solution of 5-methoxy-2-nitro-4-triisopropylsilyloxy-benzoic acid 13 (6 g, 16.24 mmol), and HOPO (1.984 g, 17.86 mMol) in $CH_2Cl_2$ (100 mL) at 0° C. The cold bath was removed and the reaction was allowed to proceed for 30 min at room temperature, at which time a solution of [(2S)-azetidin-2-yl]methoxy-tert-butyl-dimethyl-silane 6 (3.761 g, 18.68 mmol) and triethylamine (3.39 mL, 33.5 mmol) in $CH_2Cl_2$ (100 mL) was added rapidly at −10° C. under argon The reaction mixture was allowed to stir at room temperature and monitored by LC/MS. After 2 min, the reaction was complete. The solids were removed by filtration over celite and the organic phase was washed with cold aqueous 0.1 M HCl until the pH was measured at 2. The organic phase was then washed with water, followed by saturated aqueous sodium bicarbonate, brine, dried with $MgSO_4$, filtered and vacced down under reduced pressure.

Purification by silica gel column chromatography (Hex/EtOAc, 100% to 1:1) afforded product 14 (8.6737 g, 96.63% yield). LCMS 3 min: $ES^+$=2.44 min, m/z 554.2 $[M+H]^{·+}$.

b) (S)-(2-amino-5-methoxy-4-((triisopropylsilyl)oxy)phenyl)(2-(((tert-butyldimethylsilyl)oxy)methyl)azetidin-1-yl)methanone (15)

Zinc (10 g, 152.9 mMol) was slowly added to a solution of 14 (8.6737 g, 15.69 mMol) in a mixture of $MeOH/H_2O$/formic acid 90:5:5 (200 mL). The resulting exotherm was controlled using an ice bath to maintain the temperature of the reaction mixture below 40° C. Upon completion, the solids were removed by filtration over celite and the organic phase was washed with water and brine before being dried with $MgSO_4$, filtered and the volatiles removed under reduced pressure. Crude material 15 (7.6343 g, 14.6 mMol, 93.05% yield) was used as such in the next step. LCMS 3 min: $ES^+$=2.42 min, m/z 524.4 $[M+H]^{·+}$.

c) allyl (S)-(2-(2-(((tert-butyldimethylsilyl)oxy)methyl)azetidine-1-carbonyl)-4-methoxy-5-((triisopropylsilyl)oxy)phenyl)carbamate (16)

Compound 15 (7.6343 g, 14.60 mMol) was solubilised in $CH_2Cl_2$ (100 mL) under an argon atmosphere. The mixture was cooled to −78° C. before pyridine (2.6 mL, 32 mMol) and allyl chloroformate (1.7 mL, 16 mMol) were added. The reaction was left to stir at −78° C. for 10 min before being allowed to warm up to room temp. After 15 min the reaction was complete. The organics were washed with sat. $CuSO_4$, $H_2O$, brine before being dried with $MgSO_4$, filtered and the volatiles removed under reduced pressure. Crude product 16 (8.9129 g, 14.69 mMol, quantitative) was used as such in the next step. LCMS 3 min: $ES^+$=2.53 min, m/z 608.2 $[M+H]^+$.

d) Allyl (S)-(2-(2-(hydroxymethyl)azetidine-1-carbonyl)-4-methoxy-5-((triisopropylsilyl)oxy)phenyl)carbamate (17)

Compound 16 (8.9129 g, 14.69 mMol) was solubilised in a 3:1:1 mixture of $H_2O$/THF/acetic acid (80 mL) and the reaction was left to stir over the weekend. The mixture was extracted with $CH_2Cl_2$ and washed with sat. $NaHCO_3$, $H_2O$ and brine before being dried with $MgSO_4$, filtered and the volatiles removed under reduced pressure. Purification by silica gel column chromatography (Hex/EtOAc, 100% to 1:1) afforded product 17 (5.5572 g, 76.80% yield) as a clear oil. LCMS 3 min: $ES^+$=1.97 min. m/z 494.0 $[M+H]^+$.

e) Allyl (10aS)-10-hydroxy-6-methoxy-4-oxo-7-((triisopropylsilyl)oxy)-1,2,10,10a-tetrahydroazeto[1,2-a]benzo[e][1,4]diazepine-9(4H)-carboxylate (18)

Compound 17 (5.5572 g, 11.28 mMol) was solubilised in $CH_2Cl_2$ (40 mL). 1-hydroxy-2,2,6,6-tetramethyl-piperidine; 1-methylimidazole; 2-(2-pyridyl)pyridine (6 mL, 1 mMol) and tetrakisacetonitrile copper(I) triflate (425 mg, 1.1279 mMol) were subsequently added ant the mixture stirred at 35° C. with 2 balloon of air pressing in. The reaction was left to stir overnight before being vacuumed to dryness in a rotary evaporator. Purification by silica gel column chromatography ($CHCl_3$/MeOH, 100% to 97:3) afforded product 18 (5.3835 g, 10.97 mMol, 97.27% yield) as a light orange foam. LCMS 3 min: $ES^+$=2.00 min, m/z 491.8 $[M+H]^{·+}$.

f) Allyl (10aS)-10-((tert-butyldimethylsilyl)oxy)-6-methoxy-4-oxo-7-((triisopropylsilyl)oxy)-1,2,10,10a-tetrahydroazeto[1,2-a]benzo[e][1,4]diazepine-9(4H)-carboxylate (19)

Compound 18 (5.3835 g, 10.97 mMol) was solubilised in $CH_2Cl_2$ (50 mL) and the mixture was cooled to −78° C. 2,6-Lutidine (2.55 mL, 21.9 mMol) and TBS-OTf (3.78 mL, 16.4 mMol) were subsequently added. The mixture was left for 10 min before removing the cooling bath and allowing to warm to r.t. The organics were washed with, $H_2O$ and brine before being dried with $MgSO_4$, filtered and the volatiles removed under reduced pressure. Purification by silica gel column chromatography ($CHCl_3$/MeOH, 100% to 95:5) afforded product 19 (6.8532 g, quantitative). LCMS 3 min: $ES^+$=2.47 min, m/z 606.0 $[M+H]^{·+}$.

g) Allyl (10aS)-10-((tert-butyldimethylsilyl)oxy)-7-hydroxy-6-methoxy-4-oxo-1,2,10,10a-tetrahydroazeto[1,2-a]benzo[e][1,4]diazepine-9(4H)-carboxylate (20)

Compound 19 (6.8 g, 14 mMol) was solubilised in DMF (10 mL). $LiOAc·2H_2O$ (1.4 g, 14 mmMl) and $H_2O$ (3 mL or as much as possible) were added. When the solution becomes clear again, add a few drops of water. Keep repeating the process until the reaction is complete. The organics were diluted with $CHCl_3$ and washed with a citric acid solution (pH=3), $H_2O$ and brine before being dried with $MgSO_4$, filtered and the volatiles removed under reduced pressure. Purification by silica gel column chromatography ($CHCl_3$/MeOH, 100% to 95:5) afforded product 20 (5.2885 g, 11.79 mMol, 85% yield) as a yellow oil. LCMS 3 min: $ES^+$=1.86 min, m/z 449.8 $[M+H]^+$.

h) Diallyl 7,7'-(propane-1,3-diylbis(oxy))(10aS,10a'S)-bis(10-((tert-butyldimethylsilyl)oxy)-6-methoxy-4-oxo-1,2,10,10a-tetrahydroazeto[1,2-a]benzo[e][1,4]diazepine-9(4H)-carboxylate) (21)

1,3-Dibromopropane (204.9 mg, 1.015 mMol) and compound 20 (1 g, 2.030 mMol) were solubilised in $CH_2Cl_2$ (50 mL) under an argon atmosphere. $K_2CO_3$ (280 mg, 2.026 mMol) and TBAI (149 mg, 0.2 mMol) were subsequently added and the mixture was allowed to stir at 40° C. until complete. The mixture was left to stir overnight but the reaction does not go to completion instead an impurity formed. The organics were washed with $H_2O$ and brine before being dried with $MgSO_4$, filtered and the volatiles removed under reduced pressure. Purification by silica gel column chromatography ($CHCl_3$/MeOH, 100% to 97:3) afforded product 21 (482 mg, 0.471 mMol, 46.50% yield), contaminated with an inseparable impurity (r.t=9.95 min on LCMS 15 min). LCMS 15 min: $ES^+$=9.86 min, m/z 938.3 $[M+H]^{·+}$.

i) (10aS,10a'S)-7,7'-(propane-1,3-diylbis(oxy))bis(6-methoxy-1,10a-dihydroazeto[1,2-a]benzo[e][1,4]diazepin-4(2H)-one) (Ex2A)

Compound 21 (482 mg, 0.5143 mMol) was solubilised in $CH_2Cl_2$ (20 mL) in a flask under argon. Pyrrolidine (786 µL, 9.44 mMol) and $Pd(PPh_3)_4$ (54 mg, 0.046 mMol) were subsequently added and the mixture left to stir at r.t until complete. The organics were washed with sat. $NH_4Cl$, $H_2O$ and brine before being dried with $MgSO_4$, filtered and the volatiles removed under reduced pressure. Purification by isolera chromatography ($CH_2Cl_2$/($CH_2Cl_2$+10% MeOH) 98:2 to 30:70. Two fractions containing the product were isolated but with insufficient purity. The fractions were combined and repurified by isolera chromatography (same solvent system) and pure product Ex2A was isolated (35.1 mg, 0.135 mMol, 13.5% yield). LCMS 3 min: $ES^+$=1.23 min, m/z 505.8 $[M+H]^{·+}$.

j) Diallyl 7,7'-((1,3-phenylenebis(methylene))bis(oxy))(10aS,10a'S)-bis(10-((tert-butyldimethylsilyl)oxy)-6-methoxy-4-oxo-1,2,10,10a-tetrahydroazeto[1,2-a]benzo[e][1,4]diazepine-9(4H)-carboxylate) (22)

1,3-Bis(bromomethyl)benzene (267.9 mg, 1.011 mMol) and compound 20 (1 g, 2.030 mMol) were solubilised in DMF (5 mL) under an argon atmosphere. $K_2CO_3$ (280 mg, 2.026 mMol) and TBAI (749 mg, 2.027 mMol) were subsequently added and the mixture was allowed to stir at 40° C. until complete. The mixture was left to stir overnight but the reaction did not go to completion and an impurity formed. The mixture was diluted with $CH_2Cl_2$ and washed with $H_2O$ and brine before being dried with $MgSO_4$, filtered and the volatiles removed under reduced pressure. Purification by silica gel column chromatography ($CHCl_3$/MeOH, 100% to 97:3) afforded product 22 (467 mg, 0.43 mMol, 42.47% yield)+398 mg of mixed fractions. LCMS 3 min: $ES^+$=2.30 min, m/z 1000.5 $[M+H]^{·+}$.

k) (10aS,10a'S)-7,7'-((1,3-phenylenebis(methylene))bis(oxy))bis(6-methoxy-1,10a-dihydroazeto[1,2-a]benzo[e][1,4]diazepin-4(2H)-one) (Ex2B)

Compound 22 (455 mg, 0.419 mMol) was solubilised in $CH_2Cl_2$ (20 mL) in a flask under Argon. Pyrrolidine (600 µL, 7.2 mMol) and $Pd(PPh_3)_4$ (48 mg, 0.041 mMol) were subsequently added and the mixture left to stir at r.t until complete. The organics were washed with sat. $NH_4Cl$, $H_2O$ and brine before being dried with $MgSO_4$, filtered and the volatiles removed under reduced pressure. Purification by isolera chromatography ($CH_2Cl_2$/($CH_2Cl_2$+10% MeOH) 98:2 to 30:70. Two fractions containing the product were isolate but with insufficient purity. The fractions were combined and repurified by isolera chromatography (same solvent system) and pure product Ex2B was isolated (214.5 mg, 0.378 mMol, 90.5% yield) as a white solid. LCMS 3 min: $ES^+$=1.38 min, m/z 567.8 $[M+H]^{·+}$.

Example 3

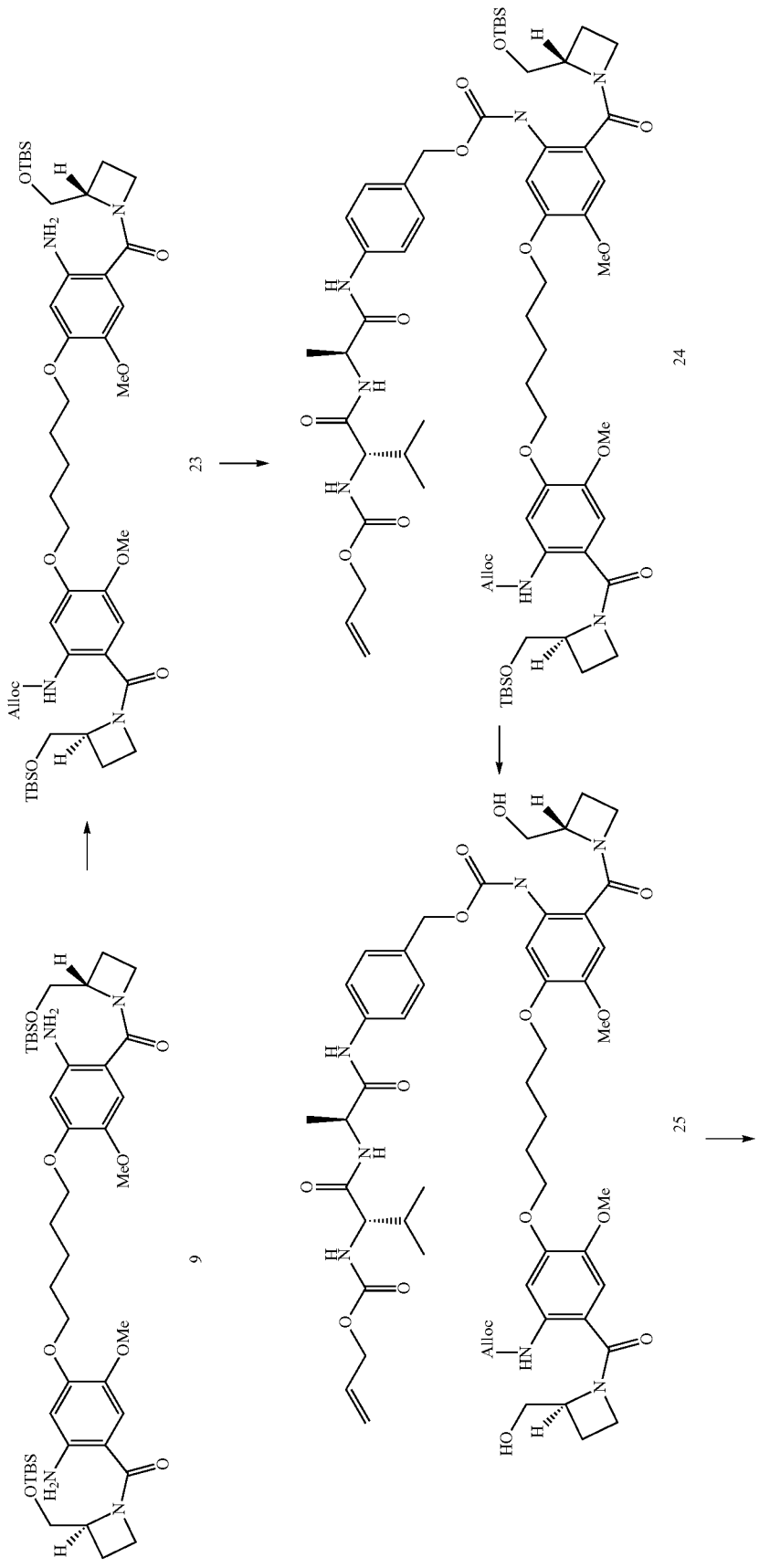

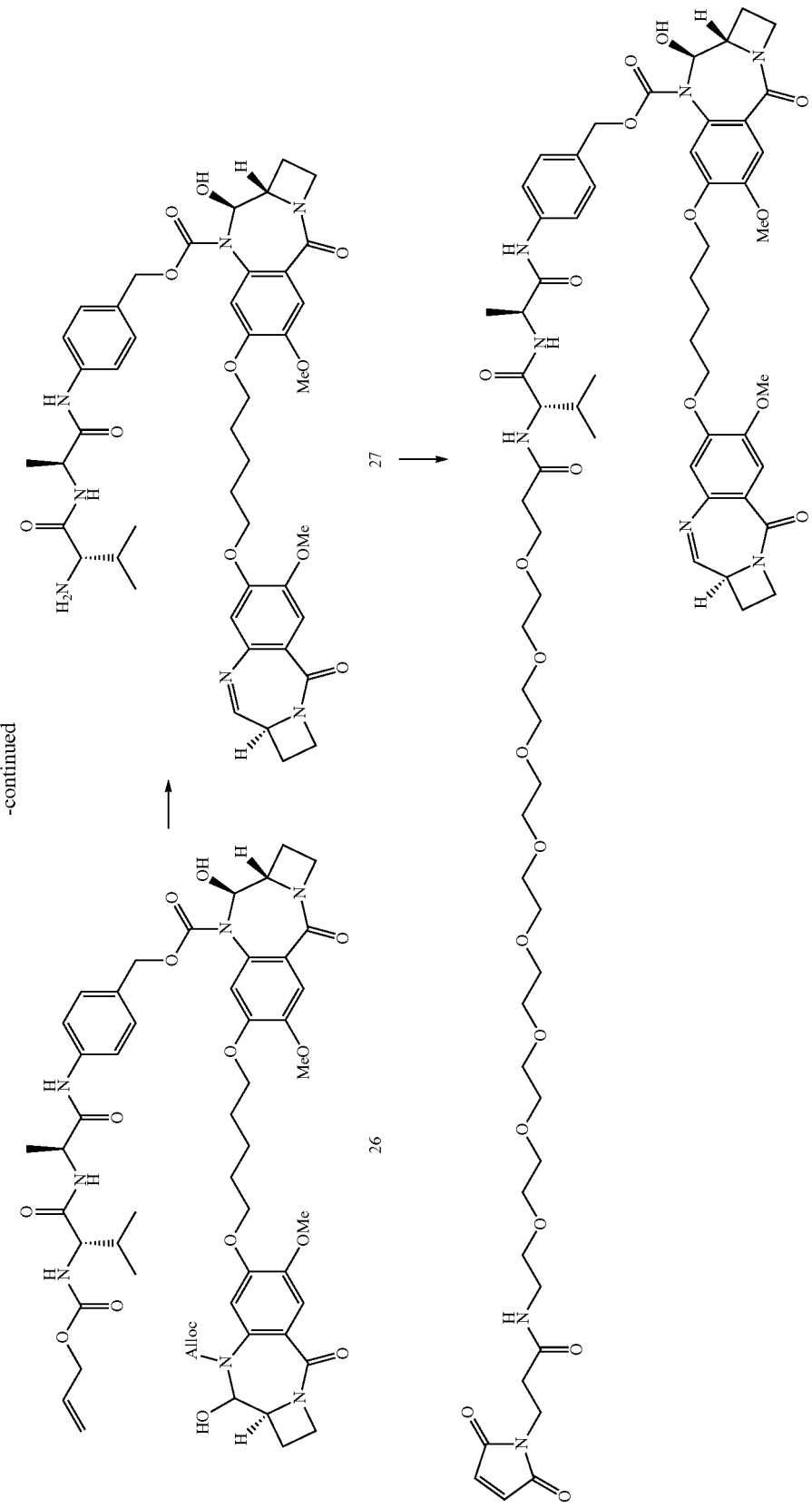

a) Allyl (5-((5-(5-amino-4-((S)-2-(((tert-butyldim-ethylsilyl)oxy)methyl)azetidine-1-carbonyl)-2-methoxyphenoxy)pentyl)oxy)-2-((S)-2-(((tert-butyldimethylsilyl)oxy)methyl)azetidine-1-carbonyl)-4-methoxyphenyl)carbamate (23)

Compound 9 (1.192 g, 1.488 mMol) was solubilised in $CH_2Cl_2$ (250 mL) under an argon atmosphere. The mixture was cooled to −78° C. before pyridine (0.241 mL, 2.98 mMol) and allyl chloroformate (0.158 mL, 1.484 mMol) were added. The reaction was left to stir at −78° C. for 10 min before being allowed to warm up to room temp. After 15 min the reaction was complete. The organics were washed with sat. $CuSO_4$, $H_2O$, brine before being dried with $MgSO_4$, filtered and the volatiles removed under reduced pressure. Purification by silica gel column chromatography ($CHCl_3$/MeOH) afforded a mixture of mono and bis-alloc which was purified further with a second column (Hex/EtOAc) to give pure product 23 (499.2 g, 37.9% yield out of 50% possible). LCMS 3 min: $ES^+$=2.41 min, m/z 886.6 $[M+H]^{.+}$.

b) Allyl (5-((5-(5-(((((4-((S)-2-((S)-2-(((allyloxy)carbonyl)amino)-3-methylbutanamido)propanamido)benzyl)oxy)carbonyl)amino)-4-((S)-2-(((tert-butyldimethylsilyl)oxy)methyl)azetidine-1-carbonyl)-2-methoxyphenoxy)pentyl)oxy)-2-((S)-2-(((tert-butyldimethylsilyl)oxy)methyl)azetidine-1-carbonyl)-4-methoxyphenyl)carbamate (24)

Triphosgene (68.8 mg, 0.232 mMol) was added in one portion to a mixture of 23 (620 mg, 0.7 mMol) and TEA (203 µL, 1.46 mMol) in $CH_2Cl_2$ (50 mL) at 0° C. The ice bath was removed, and after 15 min, Alloc-Val-Ala-PAB-OH (275 mg, 0.728 mMol) was added in one portion as a fine powder, followed by more TEA (73 µL, 0.524 mMol,) and Dibutyltin dilaurate (39.6 µL, 0.07 mMol). The reaction mixture was allowed to stir at 37° C. for 4 h, followed by stirring at room temperature overnight. The organics were washed with $H_2O$, sat. $NH_4Cl$ and brine before being dried with $MgSO_4$, filtered and the volatiles removed under reduced pressure. Purification by silica gel column chromatography ($CHCl_3$/MeOH) to give pure product 24 (414 g, 45.9% yield). LCMS 3 min: $ES^+$=2.43 min, m/z 1289.5 $[M+H]^{.+}$.

c) Allyl (5-((5-(5-(((((4-((S)-2-((S)-2-(((allyloxy)carbonyl)amino)-3-methylbutanamido)propanamido)benzyl)oxy)carbonyl)amino)-4-((S)-2-(hydroxymethyl)azetidine-1-carbonyl)-2-methoxyphenoxy)pentyl)oxy)-2-((S)-2-(hydroxymethyl)azetidine-1-carbonyl)-4-methoxyphenyl)carbamate (25)

Compound 24 (414 mg, 0.32 mMol) was solubilised in a 3:1:1 mixture of $H_2O$/THF/acetic acid (10 mL) and the reaction was left to stir over the weekend. The mixture was extracted with $CH_2Cl_2$ and washed with sat. $NaHCO_3$, $H_2O$ and brine before being dried with $MgSO_4$, filtered and the volatiles removed under reduced pressure. Purification by silica gel column chromatography ($CHCl_3$/MeOH, 100% to 94:6) afforded product 25 (326 mg, 95.7% Yield). LCMS 3 min: $ES^+$=1.80 min, m/z 1060.1 $[M+H]^{.+}$.

d) Allyl (10aS)-7-((5-(((10S,10aS)-9-(((4-((S)-2-((S)-2-(((allyloxy)carbonyl)amino)-3-methylbutanamido)propanamido)benzyl)oxy)carbonyl)-10-hydroxy-6-methoxy-4-oxo-1,2,4,9,10,10a-hexahydroazeto[1,2-a]benzo[e][1,4]diazepin-7-yl)oxy)pentyl)oxy)-10-hydroxy-6-methoxy-4-oxo-1,2,10,10a-tetrahydroazeto[1,2-a]benzo[e][1,4]diazepine-9(4H)-carboxylate (26)

Compound 25 (202.4 mg, 0.3 mMol) was solubilised in $CH_2Cl_2$ (20 mL). 1-hydroxy-2,2,6,6-tetramethyl-piperidine; 1-methylimidazole; 2-(2-pyridyl)pyridine (0.4 mL, 0.03 mMol) and tetrakisacetonitrile copper(I) triflate (11 mg, 0.03 mMol) were subsequently added ant the mixture stirred at 35° C. with 2 balloon of air pressing in. The reaction was left to stir overnight before being vacuumed to dryness in a rotary evaporator. Purification by silica gel column chromatography ($CHCl_3$/MeOH, 100% to 97:3) afforded product 26 (313 mg, 0.19 mMol, 64.5% yield). LCMS 3 min: $ES^+$=1.59 min, m/z 1057.1 $[M+H]^{.+}$.

e) 4-((S)-2-((S)-2-amino-3-methylbutanamido)propanamido)benzyl (10S,10aS)-10-hydroxy-6-methoxy-7-((5-(((S)-6-methoxy-4-oxo-1,2,4,10a-tetrahydroazeto[1,2-a]benzo[e][1,4]diazepin-7-yl)oxy)pentyl)oxy)-4-oxo-1,2,10,10a-tetrahydroazeto[1,2-a]benzo[e][1,4]diazepine-9(4H)-carboxylate) (27)

Compound 26 (195 mg, 0.184 mMol) was solubilised in $CH_2Cl_2$ (10 mL) in a flask under Argon. Pyrrolidine (262 µL, 3.15 mMol) and Pd(PPh$_3$)$_4$ (21 mg, 0.018 mMol) were subsequently added and the mixture left to stir at r.t until complete. The organics were washed with sat. $NH_4Cl$, $H_2O$ and brine before being dried with $MgSO_4$, filtered and the volatiles removed under reduced pressure. Purification by isolera chromatography ($CH_2Cl_2$/($CH_2Cl_2$+10% MeOH) 98:2 to 30:70 gave product 27 (141 mg, 0.16 mMol, 87.7% yield). LCMS 3 min: $ES^+$=1.23 min, m/z 870.9 $[M+H]^{.+}$.

f) 4-((2S,5S)-37-(2,5-Dioxo-2,5-dihydro-1H-pyrrol-1-yl)-5-isopropyl-2-methyl-4,7,35-trioxo-10,13,16,19,22,25,28,31-octaoxa-3,6,34-triazaheptatriacontanamido)benzyl (10S,10aS)-10-hydroxy-6-methoxy-7-((5-(((S)-6-methoxy-4-oxo-1,2,4,10a-tetrahydroazeto[1,2-a]benzo[e][1,4]diazepin-7-yl)oxy)pentyl)oxy)-4-oxo-1,2,10,10a-tetrahydroazeto[1,2-a]benzo[e][1,4]diazepine-9(4H)-carboxylate (Ex3)

The reaction was conducted in a glovebox. Compound 27 (70 mg, 0.080 mMol) was solubilised in $CH_2Cl_2$ (10 mL) in a flask under argon at room temperature. Mal-dPEG$_8$-OH (50 mg, 0.084 mMol) and EDCI.HCl (15.4 mg, 0.080 mMol) were added and the mixture was stirred until completion. The organics were washed with $H_2O$ and brine before being dried with $MgSO_4$, filtered and the volatiles removed under reduced pressure. Purification by isolera chromatography ($CH_2Cl_2$/($CH_2Cl_2$+10% MeOH) 98:2 to 30:70 gave an impure product. Further purification by reverse phase isolera gave pure Ex3 (4 mg, 0.027 mMol, 3.4% yield) plus some unclean fractions (22 mg). LCMS 3 min: $ES^+$=1.51 min, m/z 1445.6 $[M+H]^{.+}$.

Example 4

ConjA (Her2-Ex3)
A 10 mM solution of Tris(2-carboxyethyl)phosphine (TCEP) in phosphate-buffered saline pH 7.4 (PBS) was added (50 molar equivalent/antibody, 7.6 micromoles, 762.7 µL) to a 20.8 mL solution of tratuzumab (22.9 mg, 153 nanomoles) in reduction buffer containing 30 mM histidine/ histidine HCl, 30 mM arginine, pH 6.8 and 1 mM ethylene-diaminetetraacetic acid (EDTA) and a final antibody concentration of 1.1 mg/mL. The reduction mixture was allowed to react at 37° C. for 2 hours (or until full reduction is observed by UHPLC) in an orbital shaker with gentle (60 rpm) shaking. The reduced antibody solution was buffer exchanged (to remove all the excess reducing agent), via spin filter centrifugation, into a conjugation buffer containing 30 mM histidine/histidine HCl, 30 mM arginine and 1 mM EDTA for a final antibody concentration of 1.1 mg/mL. Ex3 was added as a DMSO solution (12.5 molar equivalent/ antibody, 1.9 micromoles, in 2.1 mL DMSO) to 18.6 mL of this reduced antibody solution (20.5 mg, 136 nanomoles) for a 10% (v/v) final DMSO concentration. The solution was mixed for 17 hours at room temperature, then the conjugation was quenched by addition of N-acetyl cysteine (8.5 micromoles, 68 µL at 100 mM), then purified via spin filter centrifugation using a 15 mL Amicon Ultracell 30 KDa MWCO spin filter, sterile-filtered and analysed.

UHPLC analysis on a Shimadzu Prominence system using a Thermo Scientific MAbPac 50 mm×2.1 mm column eluting with a gradient of water and acetonitrile on a reduced sample of ConjA at 214 nm and 330 nm (SG3931 specific) shows a mixture of unconjugated light chains, light chains attached to a single molecule of SG3931, unconjugated heavy chains and heavy chains attached to up to three molecules of SG3931, consistent with a drug-per-antibody ratio (DAR) of 7.32 molecules of SG3931 per antibody.

UHPLC analysis on a Shimadzu Prominence system using a Tosoh Bioscience TSKgel SuperSW mAb HTP 4 µm 4.6×150 mm column (with a 4 µm 3.0×20 mm guard column) eluting with 0.3 mL/minute sterile-filtered SEC buffer containing 200 mM potassium phosphate pH 6.95, 250 mM potassium chloride and 10% isopropanol (v/v) on a sample of ConjA at 280 nm shows a monomer purity of 94.2%. UHPLC SEC analysis gives a concentration of final ConjA at 1.29 mg/mL in 5.8 mL, obtained mass of ConjA is 7.5 mg (37% yield).

Example 5—Cytoxicity Assay

The potency of the molecules were measured via in vitro cytotox assays in the carcinoma cell line NCI-N87.

Solid material was dissolved in DMSO to a 2 mM stock solution, from which eight serial dilutions were made at a 1:10 ratio in DMSO and stored at −20° C. until use.

Adherent NCI-N87 cells were washed with D-PBS and detached with Trypsin-EDTA, cell density and viability were then determined in duplicate by Trypan blue exclusion assay using an automated cell counter (LUNA-II™). Cell suspension was diluted to 1×10$^5$ cells/ml in growth media (RPMI 1640 with Glutamax+10% (v/v) HyClone™ Fetal Bovine Serum) and vortexed before dispensing 2 mL per well into sterile 3 mL polypropylene plates. Warhead dilutions were then dispensed into the appropriate wells at 10 µl/well and mixed by repeat pipetting. For control wells 10 µl of DMSO was dispensed onto 2 mL cell suspension, and thoroughly mixed. 100 µl of each sample was then aliquoted into 2 replicate wells of a sterile flat 96-well microplate and incubated in a 37° C. CO$_2$-gassed (5%) incubator. At the end of the incubation period time (7 days), cell viability was measured by CellTiter 96 Aqueous One (MTS) assay, which was dispensed at 20 µl/well and incubated for 4 hours at 37° C., 5% CO$_2$. Plates were then read on an EnVision Multi-label Plate Reader (Perkin Elmer) using absorbance at 490 nm.

Cell survival percentage was calculated from the mean absorbance of the 2 replicate wells for each sample, compared to the mean absorbance in the two control wells treated with DMSO only (100%). The IC$_{50}$ was determined by fitting each data set to sigmoidal dose-response curves with a variable slope using the non-linear curve fit algorithm on the GraphPad Prism software (San Diego, CA).

All the experiments in this report were carried out and tested in three independent experiments. Data are reported as the mean of the three independent replicates.

|       | IC$_{50}$ (nM) |
|-------|----------------|
| Ex2A  | 70.11          |
| Ex1   | 2.202          |
| Ex2B  | 4.035          |

Example 6—ADC Cytoxicity Assay

The concentration and viability of cells from a subconfluent (80-90% confluency) T75 flask are measured by trypan blue staining and counted using the LUNA-II™ Automated Cell Counter. Cells were diluted to 2×10$^5$/ml, dispensed (50 µl per well) into 96-well flat-bottom plates.

A stock solution (1 ml) of the test antibody drug conjugate (ADC) (20 µg/ml) was made by dilution of filter-sterilised ADC into cell culture medium. A set of 8×10-fold dilutions of stock ADC were made in a 24-well plate by serial transfer of 100 µl into 900 µl of cell culture medium. ADC dilution was dispensed (50 µl per well) into 4 replicate wells of the 96-well plate, containing 50 µl cell suspension seeded the previously. Control wells received 50 µl cell culture medium. The 96-well plate containing cells and ADCs was incubated at 37C in a CO$_2$-gassed incubator for the exposure time.

At the end of the incubation period, cell viability was measured by MTS assay. MTS (Promega) was dispensed (20 µl per well) into each well and incubated for 4 hours at 37° C. in the CO$_2$-gassed incubator. Well absorbance was measured at 490 nm. Percentage cell survival was calculated from the mean absorbance in the 4 ADC-treated wells compared to the mean absorbance in the 4 control untreated wells (100%). IC$_{50}$ was determined from the dose-response data using GraphPad Prism using the non-linear curve fit algorithm: sigmoidal dose-response curve with variable slope.

ADC incubation times were 4 days with MDA-MB-468 and 7 days for NCI-N87. MDA-MB-468 and NCI-N87 were cultured in RPMI 1640 with Glutamax+10% (v/v) HyClone™ Fetal Bovine Serum.

The EC$_{50}$ values were determined by fitting data to a sigmoidal dose-response curve with variable slope using GraphPad Prism software v6.05 (GraphPad, San Diego, CA).

|       | EC$_{50}$ (µg/ml) | |
|-------|---------|------------|
|       | NCI-N87 | MDA-MB-468 |
| ConjA | 0.002285 | 15.71     |

Example 7—Xenograft Testing

NCI-N87 Xenografted Mice

Female severe combined immune-deficient mice (Fox Chase SCID®, C.B-17/lcr-Prkdcscid, Charles River) were eight weeks old with a body weight (BW) range of 16.5 to 21.6 grams on Day 1 of the study. The animals were fed ad libitum water (reverse osmosis, 1 ppm Cl), and NIH 31 Modified and Irradiated Lab Diet® consisting of 18.0% crude protein, 5.0% crude fat, and 5.0% crude fibre. The mice were housed on irradiated Enricho'cobs™ Laboratory Animal Bedding in static micro-isolators on a 12-hour light cycle at 20-22° C. (68-72° F.) and 40-60% humidity. CR Discovery Services specifically complies with the recommendations of the Guide for Care and Use of Laboratory Animals with respect to restraint, husbandry, surgical procedures, feed and fluid regulation, and veterinary care. The animal care and use program at CR Discovery Services is accredited by the Association for Assessment and Accreditation of Laboratory Animal Care International (AAALAC), which assures compliance with accepted standards for the care and use of laboratory animals.

Tumour Cell Culture

Human NCI-N87 gastric carcinoma lymphoma cells were cultured in RPMI-1640 medium supplemented with 10% fetal bovine serum, 2 mM glutamine, 100 units/mL penicillin G sodium, 100 µg/mL streptomycin sulfate and 25 µg/mL gentamicin. The cells were grown in tissue culture flasks in a humidified incubator at 37° C., in an atmosphere of 5% $CO_2$ and 95% air.

In Vivo Implantation and Tumour Growth

The NCI-N87 cells used for implantation were harvested during log phase growth and Re-suspended in phosphate buffered saline (PBS) containing 50% Matrigel™ (BD Biosciences). On the day of tumour implant, each test mouse was injected subcutaneously in the right flank with $1 \times 10^7$ cells (0.1 mL cell suspension), and tumour growth was monitored as the average size approached the target range of 100 to 150 mm³. Fourteen days later, designated as Day 1 of the study, mice were sorted according to calculated tumour size into groups each consisting of ten animals with individual tumour volumes ranging from 108 to 144 mm³ and group mean tumour volumes of 115 mm³.

Tumours were measured in two dimensions using calipers, and volume was calculated using the formula:

$$\text{Tumour Volume (mm}^3) = \frac{w^2 \times l}{2}$$

where w=width and l=length, in mm, of the tumour. Tumour weight may be estimated with the assumption that 1 mg is equivalent to 1 mm³ of tumour volume.

Treatment

Treatment began on Day 1 in groups of 10 mice (n=10) with established subcutaneous NCI-N87 tumours (108-144 mm³). ConjA (4 mg/kg) was administered intravenously once on Day 1 (qd×1). A vehicle-treated group served as the control group for efficacy analysis. Tumours were measured twice per week until the study was ended on Day 79. Each mouse was euthanized when its tumour reached the endpoint volume of 800 mm³ or on the final day, whichever came first. The time to endpoint (TTE) was calculated for each mouse.

The results are illustrated in FIG. 1 which shows the change in normalised tumour growth (■—control; ◆—ConjA).

Endpoint and Tumor Growth Delay (TGD) Analysis

Tumors were measured using calipers twice per week, and each animal was euthanized when its tumor reached the endpoint volume of 800 mm³ or at the end of the study (Day 79), whichever came first. Animals that exited the study for tumor volume endpoint were documented as euthanized for tumor progression (TP), with the date of euthanasia. The time to endpoint (TTE) for analysis was calculated for each mouse by the following equation:

$$TTE = \frac{\log_{10}(\text{endpoint volume}) - b}{m}$$

where TTE is expressed in days, endpoint volume is expressed in mm³, b is the intercept, and m is the slope of the line obtained by linear regression of a log-transformed tumor growth data set. The data set consisted of the first observation that exceeded the endpoint volume used in analysis and the three consecutive observations that immediately preceded the attainment of this endpoint volume. The calculated TTE is usually less than the TP date, the day on which the animal was euthanized for tumor size. Animals with tumors that did not reach the endpoint volume were assigned a TTE value equal to the last day of the study (Day 79). In instances in which the log-transformed calculated TTE preceded the day prior to reaching endpoint or exceeded the day of reaching tumor volume endpoint, a linear interpolation was performed to approximate the TTE. Any animal classified as having died from NTR (non-treatment-related) causes due to accident (NTRa) or due to unknown etiology (NTRu) were excluded from TTE calculations (and all further analyses). Animals classified as TR (treatment-related) deaths or NTRm (non-treatment-related death due to metastasis) were assigned a TTE value equal to the day of death. Treatment outcome was evaluated from tumor growth delay (TGD), which is defined as the increase in the median time to endpoint (TTE) in a treatment group compared to the control group:

$$TGD = T - C,$$

expressed in days, or as a percentage of the median TTE of the control group:

$$\% \, TGD = \frac{T - C}{C} \times 100$$

where:
T=median TTE for a treatment group, and
C=median TTE for the designated control group.

Tumour Growth Inhibition

Tumor growth inhibition (TGI) analysis evaluates the difference in median tumor volumes (MTVs) of treated and control mice. For this study, the endpoint for determining TGI was Day 19, which was the last day that all evaluable control mice remained in the study. The MTV (n), the median tumor volume for the number of animals, n, on the day of TGI analysis, was determined for each group. Percent tumor growth inhibition (% TGI) was defined as the difference between the MTV of the designated control group and the MTV of the drug-treated group, expressed as a percentage of the MTV of the control group:

$$\% \ TGI = \left( \frac{MTV_{control} - MTV_{drug-treated}}{MTV_{control}} \right) \times 100 = [1 - (MTV_{drug-treated} / MTV_{control})] \times 100$$

The data set for TGI analysis included all animals in a group, except those that died due to treatment-related (TR) or non-treatment-related (NTR) causes prior to the day of TGI analysis.

MTV and Criteria for Regression Responses

Treatment efficacy may be determined from the tumor volumes of animals remaining in the study on the last day. The MTV (n) was defined as the median tumor volume on the last day of the study in the number of animals remaining (n) whose tumors had not attained the endpoint volume. Treatment efficacy may also be determined from the incidence and magnitude of regression responses observed during the study. Treatment may cause partial regression (PR) or complete regression (CR) of the tumor in an animal. In a PR response, the tumor volume was 50% or less of its Day 1 volume for three consecutive measurements during the course of the study, and equal to or greater than 13.5 mm³ for one or more of these three measurements. In a CR response, the tumor volume was less than 13.5 mm³ for three consecutive measurements during the course of the study. Animals were scored only once during the study for a PR or CR event and only as CR if both PR and CR criteria were satisfied. An animal with a CR response at the termination of a study was additionally classified as a tumor-free survivor (TFS). Animals were monitored for regression responses.

Toxicity

Animals were weighed daily on Days 1-5, then twice per week until the completion of the study. The mice were observed frequently for overt signs of any adverse, treatment-related (TR) side effects, and clinical signs were recorded when observed. Individual body weight was monitored as per protocol, and any animal with weight loss exceeding 30% for one measurement or exceeding 25% for three consecutive measurements was euthanized as a TR death. Group mean body weight loss was also monitored according to CR Discovery Services protocol. Acceptable toxicity was defined as a group mean body weight (BW) loss of less than 20% during the study and no more than 10% TR deaths. Dosing was suspended in any group where mean weight loss exceeded acceptable limits. If group mean body weight recovered to acceptable levels, then dosing was modified to lower levels and/or reduced frequency then resumed. Deaths were classified as TR if it was attributable to treatment side effects as evidenced by clinical signs and/or necropsy. A TR classification was also assigned to deaths by unknown causes during the dosing period or within 14 days of the last dose. A death was classified as non-treatment-related (NTR) if there was no evidence that death was related to treatment side effects. NTR deaths are further categorized as follows: NTRa describes deaths due to accidents or human error; NTRm is assigned to deaths thought to result from tumor dissemination by invasion and/or metastasis based on necropsy results; NTRu describes deaths of unknown causes that lack available evidence of death related to metastasis, tumor progression, accident or human error. It should be noted that treatment side effects cannot be excluded from deaths classified as NTRu.

Statistical and Graphical Analyses

GraphPad Prism 8.0 for Windows was used for all statistical analysis and graphical presentations. Study groups experiencing toxicity beyond acceptable limits (>20% group mean body weight loss or greater than 10% treatment-related deaths) or having fewer than five evaluable observations, were not included in the statistical analysis. The logrank test was employed to assess the significance of the difference between the overall survival experiences of two groups. The logrank test analyzes the individual TTEs for all animals in a group, except those lost to the study due to NTR death. Statistical analyses of the differences between Day 19 median tumor volumes (MTVs) of control and treated groups were accomplished using the Mann-Whitney U-test. For statistical analyses, two-tailed tests were conducted at significance level P=0.05. Prism summarizes test results as not significant (ns) at P>0.05, significant (symbolized by "*") at 0.01<P≤0.05, very significant ("") at 0.001<P≤0.01, and extremely significant ("*") at P ≤ 0.001. Because tests of statistical significance do not provide an estimate of the magnitude of the difference between groups, all levels of significance were described as either significant or not significant within the text of this report.

|  |  | n | Median TTE | T-C | % TGD | MTV (n), Day 79 |
|---|---|---|---|---|---|---|
| Vehicle | — | 10 | 24.8 | — | — | 466 (10) |
| ConjA | 4 mg/kg | 10 | 79.0 | 54.2 | 219 | 32 (9) |

|  | PR | CR | TFS | BW Nadir | TR | NTRm | NTR |
|---|---|---|---|---|---|---|---|
| Vehicle | 0 | 0 | 0 | −2.0 (2) | 0 | 0 | 0 |
| ConjA | 6 | 4 | 0 | −1.9 (2) | 0 | 0 | 0 |

The Day 19 MTV(10) for animals treated with ConjA was 32 mm³, or a significant 93% TGI (P<0.001, Mann-Whitney). Nine animals survived the study and the assigned median TTE was 79.0 days; this represents the maximally possible, significant 219% TGD (P<0.001, logrank). The MTV(9) on Day 79 was 320 mm³ and there were six PRs and four CRs.

All documents and other references mentioned above are herein incorporated by reference.

STATEMENTS OF INVENTION

1. A compound of formula IV:

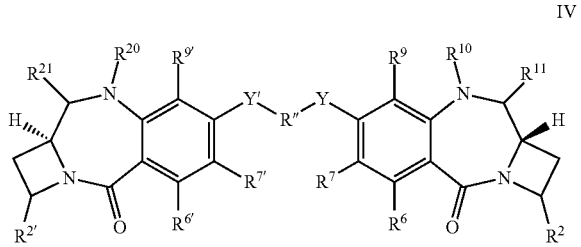

and salts and solvates thereof, wherein:
$R^2$ and $R^{2'}$ are H;
$R^6$ and $R^9$ are independently selected from H, R, OH, OR, SH, SR, $NH_2$, NHR, NRR', nitro, $Me_3Sn$ and halo;

where R and R' are independently selected from optionally substituted $C_{1-12}$ alkyl, $C_{3-20}$ heterocyclyl and $C_{5-20}$ aryl groups;
either
(a) $R^7$ is selected from H, R, OH, OR, SH, SR, $NH_2$, NHR, NRR', nitro, $Me_3Sn$ and halo; $R^{7'}$ is selected from H, R, OH, OR, SH, SR, $NH_2$, NHR, NRR', nitro, $Me_3Sn$ and halo; or
(b) $R^7$ and $R^{7'}$ together form a group which is: (i) $-O-(CH_2)_n-O-$, where n is from 7 to 16; or (ii) $-O-(CH_2CH_2O)_m-$, where m is 2 to 5;
R" is a $C_{3-12}$ alkylene group, which chain may be interrupted by one or more heteroatoms, e.g. O, S, $NR^{N2}$ (where $R^{N2}$ is H or $C_{1-4}$ alkyl), and/or aromatic rings, e.g. benzene or pyridine;
Y and Y' are selected from O, S, or NH;
$R^{6'}$ and $R^{9'}$ are selected from the same groups as $R^6$, and $R^9$ respectively;
either
(i-a) $R^{10}$ and $R^{11}$ together form a double bond between the N and C atoms to which they are bound; or
(i-b) $R^{10}$ is H and $R^{11}$ is selected from OH and $OR^A$, where $R^A$ is $C_{1-4}$ alkyl; or
(i-c) $R^{10}$ and $R^{11}$ are both H; either
(ii-a) $R^{20}$ and $R^{21}$ together form a double bond between the N and C atoms to which they are bound; or
(ii-b) $R^{20}$ is H and $R^{21}$ is selected from OH and $OR^B$, where $R^B$ is $C_{1-4}$ alkyl; or
(ii-c) $R^{20}$ and $R^{21}$ are both H.

2. A compound according to statement 1, wherein both Y and Y' are O.

3. A compound according to either statement 1 or statement 2, wherein R" is $C_{3-7}$ alkylene.

4. A compound according to either statement 1 or statement 2, wherein R" is a group of formula:

where r is 1 or 2.

5. A compound according to any one of statements 1 to 4, wherein $R^9$ is H.

6. A compound according to any one of statements 1 to 5, wherein $R^6$ is H.

7. A compound according to any one of statements 1 to 6, wherein $R^7$ is selected from H, OH and OR and $R^{7'}$ is selected from H, OH and OR 8. A compound according to statement 7, wherein $R^7$ is a $C_{1-4}$ alkyloxy group and $R^{7'}$ is a $C_{1-4}$ alkyloxy group.

9. A compound according to any one of statements 1 to 8, wherein $R^{2'}$ is the same as $R^2$, $R^{6'}$ is the same group as $R^6$, $R^{7'}$ is the same group as $R^7$, $R^{9'}$ is the same group as $R^9$ and Y' is the same group as Y.

10. A compound according to any one of statements 1 to 9, wherein $R^{10}$ and $R^{11}$ together form a double bond between the N and C atoms to which they are bound.

11. A compound according to any one of statements 1 to 9, wherein $R^{10}$ is H and $R^{11}$ is selected from OH and $OR^A$.

12. A compound according to statement 11, wherein $R^A$ is methyl.

13. A compound according to any one of statements 1 to 9, wherein $R^{10}$ and $R^{11}$ are both H.

14. A compound according to any one of statements 1 to 13, wherein $R^{20}$ and $R^{21}$ together form a double bond between the N and C atoms to which they are bound.

15. A compound according to any one of statements 1 to 13, wherein $R^{20}$ is H and $R^{21}$ is selected from OH and $OR^B$.

16. A compound according to statement 14, wherein $R^B$ is methyl.

17. A compound according to any one of statements 1 to 13, wherein $R^{20}$ and $R^{21}$ are both H.

18. A compound according to statement 1 which is of formulae IVa, IVb or IVc:

where $R^{1a}$ is selected from methyl and benzyl.

19. A compound of formula I:

and salts and solvates thereof, wherein:
Y, Y', R", $R^2$, $R^{2'}$, $R^6$, $R^{6'}$, $R^7$, $R^{7'}$, $R^9$ and $R^{9'}$ are as defined in any one of statements 1 to 18;
$R^{11b}$ is selected from OH, $OR^A$, where $R^A$ is $C_{1-4}$ alkyl; and $R^L$ is a linker for connection to a cell binding agent, which is selected from:

(iiia):

[Structure IIIa: benzyl group connected to NH-Q-X-$G^L$ with wavy bond]

IIIa wherein

Q is:

[Structure: C(=O) wavy bond to NH-$Q^X$-C(=O) wavy bond, with NH label]

where $Q^X$ is such that Q is an amino-acid residue, a dipeptide residue or a tripeptide residue;

X is:

[Structure: C(=O) wavy bond-[CH_2]_a-[O]_b-[CH_2CH_2]-NH-C(=O)-[ ]_d wavy bond $G^L$]

where a=0 to 5, b=0 to 16, c=0 or 1, d=0 to 5;

$G^L$ is a linker for connecting to a Ligand Unit; and (iiib):

[Structure IIIb: $R^{L1}$, $R^{L2}$ on carbon connected to S-S-pyridyl with $[NO_2]_e$]

IIIb where $R^{L1}$ and $R^{L2}$ are independently selected from H and methyl, or together with the carbon atom to which they are bound form a cyclopropylene or cyclobutylene group;

and e is 0 or 1;

either:
(a) $R^{30}$ and $R^{31}$ together form a double bond between the N and C atoms to which they are bound; or
(b) $R^{30}$ is H and $R^{31}$ is selected from OH and $OR^B$, where $R^B$ is $C_{1-4}$ alkyl; or
(c) $R^{30}$ and $R^{31}$ are both H; or (d) $R^{31}$ is OH or $OR^B$, where $R^B$ is $C_{1-4}$ alkyl and $R^{30}$ is selected from:

(i)

[Structure: Ph-S(=O)(=O)-CH_2CH_2-O-C(=O)-* ]

(ii)

[Structure: Me-O-CH_2CH_2-O-C(=O)-* ]

(iii)

[Structure: 4-$R^Z$-benzyl-O-C(=O)-* ]

where $R^Z$ is selected from:

[Structure: *-O-C(=O)-N-piperazine-N-Me ]

(z-i);

(z-ii) OC(=O)CH_3;

(z-iii) NO_2;

(z-iv) OMe;

(z-v) glucoronide;

(z-vi) NH—C(=O)—X_1—NHC(=O)X_2—NH—C(=O)—$R^{ZC}$, where —C(=O)—X_1—NH— and —C(=O)—X_2—NH— represent natural amino acid residues and $R^{ZC}$ is selected from Me, OMe, CH_2CH_2OMe, and (CH_2CH_2O)_2Me.

20. A compound according to statement 19, wherein $R^{30}$ and $R^{31}$ together form a double bond between the N and C atoms to which they are bound.

21. A compound according to statement 19, wherein $R^{30}$ is H and $R^{31}$ is selected from OH and $OR^B$, where $R^B$ is $C_{1-4}$ alkyl.

22. A compound according to statement 19, wherein $R^{30}$ and $R^{31}$ are both H.

23. The compound according to statement 19, wherein $R^{31}$ is OH or $OR^A$ and $R^{30}$ is selected from:

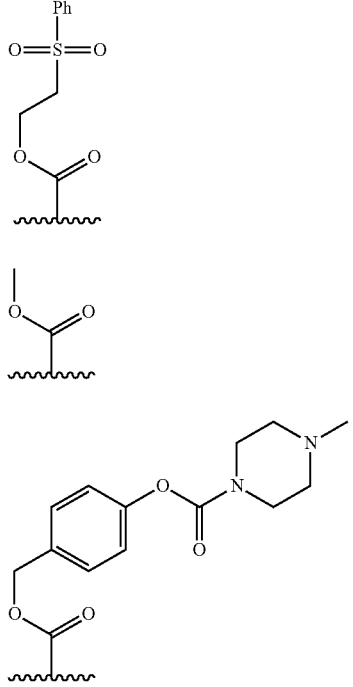

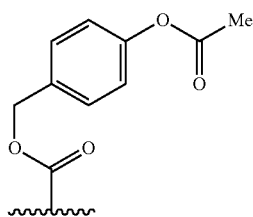

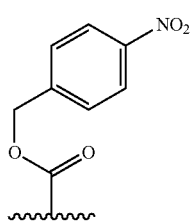

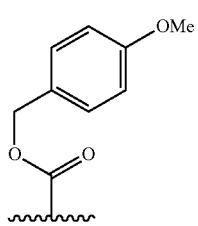

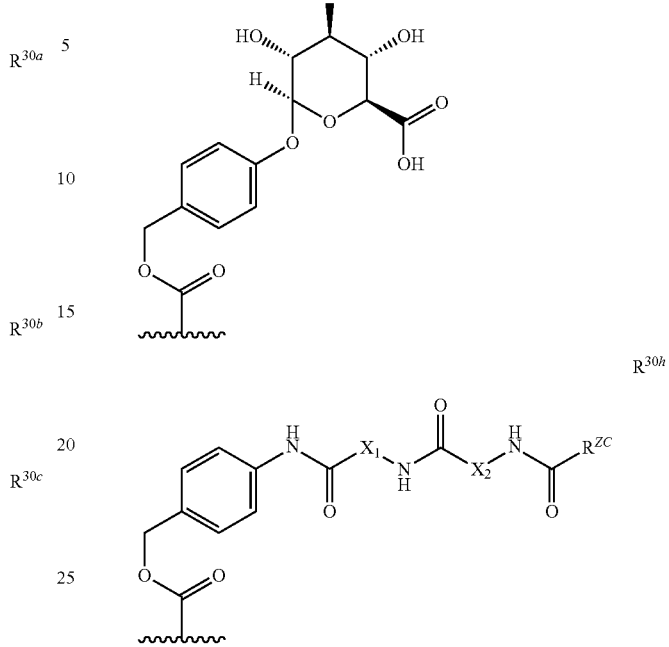

24. The compound according to statement 23, wherein —C(=O)—$X_1$—NHC(=O)$X_2$—NH—, is selected from: -Phe-Lys-, -Val-Ala-, -Val-Lys-, -Ala-Lys-, and -Val-Cit-.

25. The compound according to statement 23, wherein —C(=O)—$X_1$—NHC(=O)$X_2$—NH—, is selected from: -Phe-Lys-, and -Val-Ala-.

26. The compound according to any one of statements 23 to 25 wherein $R^{ZC}$ is selected from $CH_2CH_2OMe$, and $(CH_2CH_2O)_2Me$.

27. The compound according to statement 26 wherein $R^{ZC}$ is $(CH_2CH_2O)_2Me$.

28. A compound according to statement 19, which is of formulae Ia, Ib or Ic:

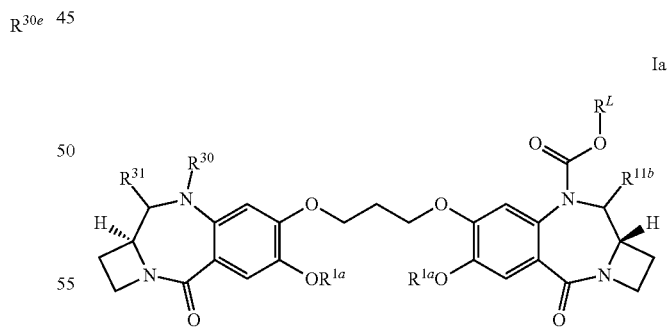

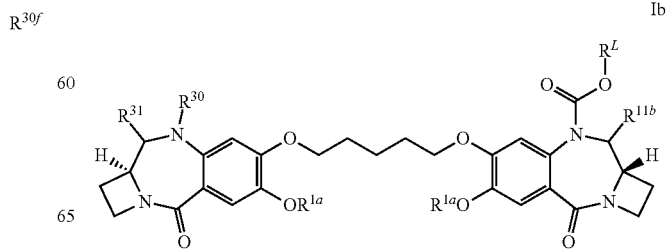

-continued

Ic

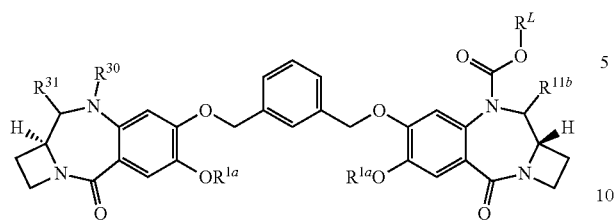

where $R^{1a}$ is selected from methyl and benzyl.

29. A compound according to any one of statements 19 to 28, wherein $R^{11b}$ is OH.

30. A compound according to any one of statements 19 to 29, wherein $R^{11b}$ is $OR^A$, where $R^A$ is $C_{1-4}$ alkyl.

31. A compound according to statement 30, wherein $R^A$ is methyl.

32. A compound according to any one of statements 19 to 31, wherein $R^L$ is of formula IIIa, and Q is an amino acid residue selected from Phe, Lys, Val, Ala, Cit, Leu, Ile, Arg, and Trp.

33. A compound according to any one of statements 19 to 31, wherein $R^L$ is of formula IIIa, and Q is a dipeptide residue selected from:
$^{CO}$-Phe-Lys-$^{NH}$,
$^{CO}$-Val-Ala-$^{NH}$,
$^{CO}$-Val-Lys-$^{NH}$,
$^{CO}$-Ala-Lys-$^{NH}$,
$^{CO}$-Val-Cit-$^{NH}$,
$^{CO}$-Phe-Cit-$^{NH}$,
$^{CO}$-Leu-Cit-$^{NH}$,
$^{CO}$-Ile-Cit-$^{NH}$,
$^{CO}$-Phe-Arg-$^{NH}$, and
$^{CO}$-Trp-Cit-$^{NH}$.

34. A compound according to statement 33, wherein Q is selected from $^{CO}$-Phe-Lys-$^{NH}$, $^{CO}$-Val-Cit-$^{NH}$ and $^{CO}$-Val-Ala-$^{NH}$.

35. A compound according to any one of statements 19 to 31, wherein $R^L$ is of formula IIIa, and Q is a tripeptide residue selected from:
$^{CO}$-Glu-Val-Ala-$^{NH}$,
$^{CO}$-Glu-Val-Cit-$^{NH}$,
$^{CO}$-αGlu-Val-Ala-$^{NH}$, and
$^{CO}$-αGlu-Val-Cit-$^{NH}$.

36. A compound according to any one of statements 19 to 35, wherein $R^L$ is of formula IIIa and a is 0 to 3.

37. A compound according to statement 36, wherein a is 0.

38. A compound according to any one of statements 19 to 37, wherein $R^L$ is of formula IIIa and b is 0 to 12.

39. A compound according to statement 38, wherein b is 0 to 8.

40. A compound according to any one of statements 19 to 39, wherein $R^L$ is of formula IIIa and d is 0 to 3.

41. A compound according to statement 38, wherein d is 2.

42. A compound according to any one of statements 19 to 35, wherein $R^L$ is of formula IIIa and, a is 0, c is 1 and d is 2, and b is from 0 to 8.

43. A compound according to statement 42, wherein b is 0, 4 or 8.

44. A compound according to any one of statements 19 to 43 wherein $R^L$ is of formula IIIa and $G^L$ is selected from:

(G$^{L1-1}$)

(G$^{L1-2}$)

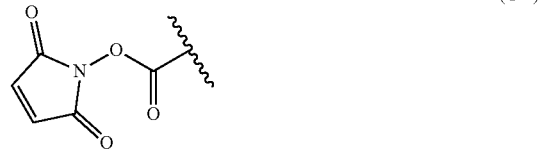

(G$^{L2}$)

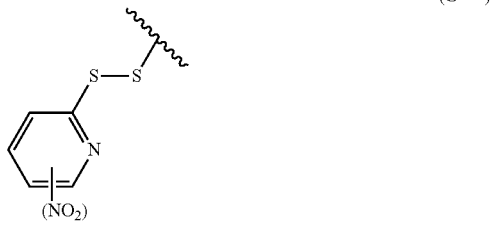

(G$^{L3-1}$)

where the NO$_2$ group is optional

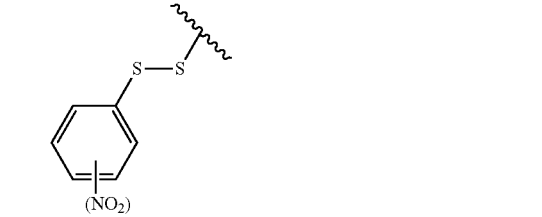

(G$^{L3-2}$)

where the NO$_2$ group is optional

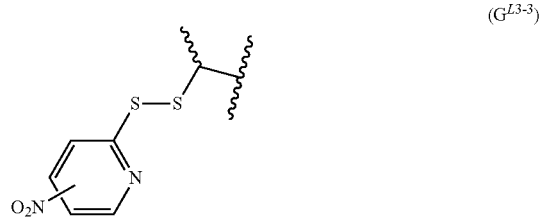

(G$^{L3-3}$)

where the NO$_2$ group is optional

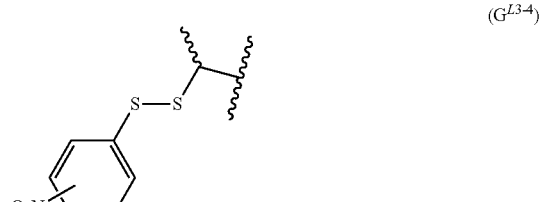

(G$^{L3-4}$)

where the NO$_2$ group is optional

-continued (G^{L4}) 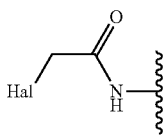

Where Hal = I, Br, Cl (G^{L5}) 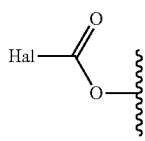

(G^{L6}) 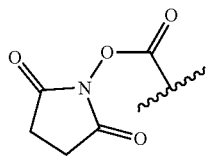

(G^{L7}) 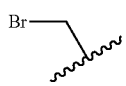

(G^{L8})

(G^{L9})

where Ar represents a $C_{5-6}$ arylene group.

45. A compound according to statement 44, wherein Ar is a phenylene group.

46. A compound according to either statement 44 or statement 45, wherein $G^L$ is selected from $G^{L1-1}$ and $G^{L1-2}$.

47. A compound according to statement 46, wherein $G^L$ is $G^{L1-1}$.

48. A compound according to any one of statements 19 to 31, wherein $R^L$ is of formula IIIb, and both $R^{L1}$ and $R^{L2}$ are H.

49. A compound according to any one of statements 19 to 31, wherein $R^L$ is of formula IIIb, $R^{L1}$ is H and $R^{L2}$ is methyl.

50. A compound according to any one of statements 19 to 31, wherein $R^L$ is of formula IIIb, and both $R^{L1}$ and $R^{L2}$ are methyl.

51. A compound according to any one of statements 19 to 31, wherein $R^L$ is of formula IIIb, and, $R^{L1}$ and $R^{L2}$ together with the carbon atom to which they are bound form a cyclopropylene group.

52. A compound according to any one of statements 19 to 31, wherein $R^L$ is of formula IIIb, and, $R^{L1}$ and $R^{L2}$ together with the carbon atom to which they are bound form a cyclobutylene group.

53. A compound according to any one of statements 19 to 31 and 48 to 52, wherein $R^L$ is of formula IIIb, and e is 0.

54. A compound according to any one of statements 19 to 31 and 48 to 52, wherein $R^L$ is of formula IIIb, and e is 1.

55. A compound according to statement 54, wherein the nitro group is in the para position.

56. A compound according to statement 19, wherein the compound is of formula Id:

(Id)

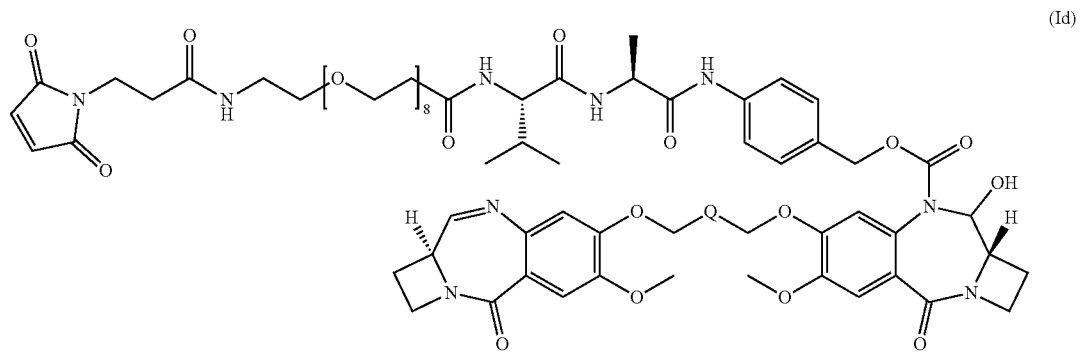

where Q is selected from:
(a) —CH$_2$—;
(b) —C$_3$H$_6$—; and

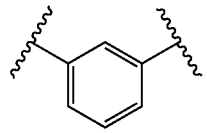
(c)

57. A conjugate of formula II:

L-(D$^L$)$_p$ (II)

wherein L is a Ligand unit (i.e., a targeting agent), D$^L$ is a Drug Linker unit of formula I':

I*

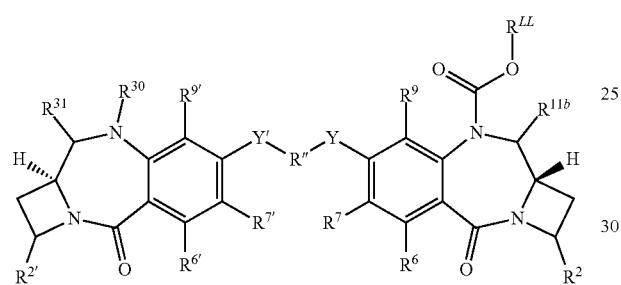

wherein:
Y, Y', R", R$^2$, R$^{2'}$, R$^6$, R$^{6'}$, R$^7$, R$^{7'}$, R$^9$ and R$^{9'}$ are as defined in any one of statements 1 to 18;
R$^{11b}$, R$^{30}$ and R$^{31}$ are as defined in any one of statements 19 to 27 and 29 to 31;
R$^{LL}$ is a linker for connection to a cell binding agent, which is selected from:
(iiia):

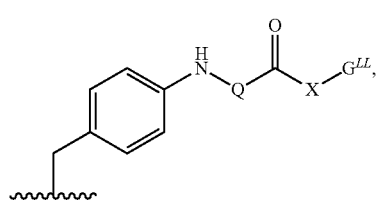
IIIa' where Q and X are as defined in any one of statements 19 and 32 to 43 and G$^{LL}$ is a linker connected to a Ligand Unit; and
(iiib):

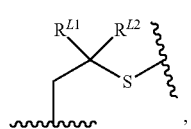
IIIb' where R$^{L1}$ and R$^{L2}$ are as defined in any one of statements 19 and 48 to 52;

wherein p is an integer of from 1 to 20.

58. A conjugate according to statement 57, wherein G$^{LL}$ is selected from:

(G$^{LL1-1}$)

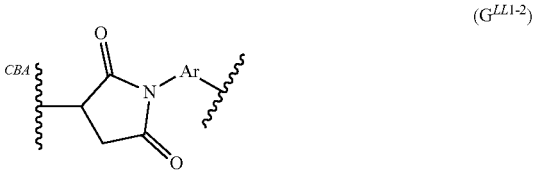
(G$^{LL1-2}$)

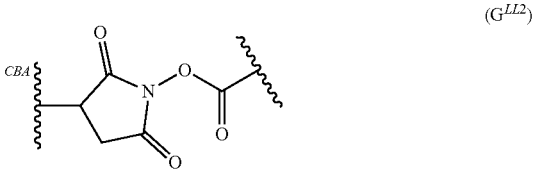
(G$^{LL2}$)

(G$^{LL3-1}$)

(G$^{LL3-2}$)

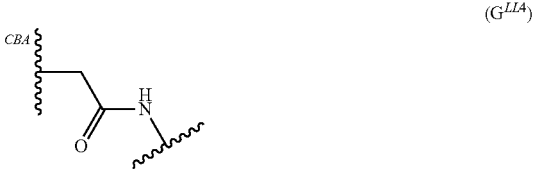
(G$^{LL4}$)

(G$^{LL5}$)

(G$^{LL6}$)

(G$^{LL7}$)

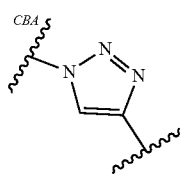 (G^{LL8-1})

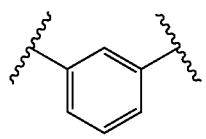 (G^{LL8-2})

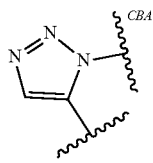 (G^{LL9-1})

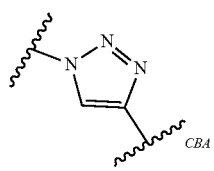 (G^{LL9-2})

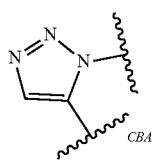

where r represents a $C_{5-6}$ arylene group.

59. A conjugate according to statement 58, wherein Ar is a phenylene group.

60. A conjugate according to either statement 58 or statement 59, wherein $G^{LL}$ is selected from $G^{LL1-1}$ and $G^{LL1-2}$.

61. A conjugate according to statement 60, wherein $G^{LL}$ is $G^{LL}$-11.

62. A conjugate according to statement 57, wherein $D^L$ is of formula (Id'):

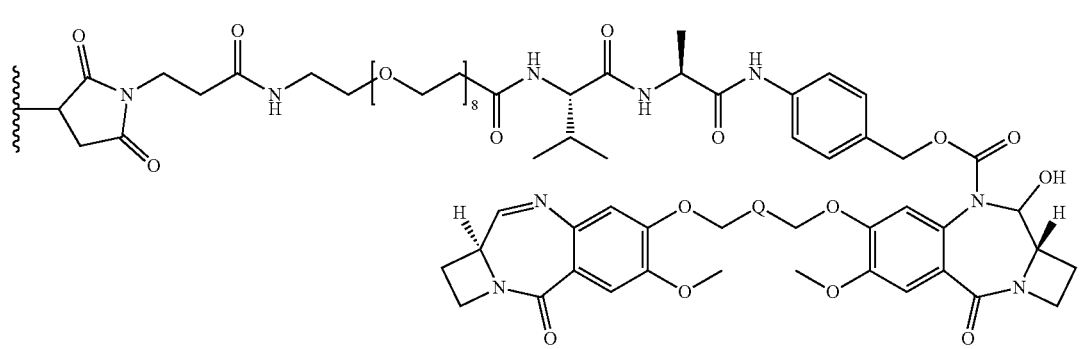 (I*d)

where Q is selected from:
(a) —$CH_2$—;
(b) —$C_3H_6$—; and
(c)

63. A conjugate according to any one of statements 57 to 62, wherein the Ligand Unit is an antibody or an active fragment thereof.

64. The conjugate according to statement 63, wherein the antibody or antibody fragment is an antibody or antibody fragment for a tumour-associated antigen.

65. The conjugate according to statement 64, wherein the antibody or antibody fragment is an antibody which binds to one or more tumor-associated antigens or cell-surface receptors selected from (1)-(88):

(1) BMPR1B;
(2) E16;
(3) STEAP1;
(4) 0772P;
(5) MPF;
(6) Napi3b;
(7) Sema 5b;
(8) PSCA hlg;
(9) ETBR;
(10) MSG783;
(11) STEAP2;
(12) TrpM4;
(13) CRIPTO;
(14) CD21;
(15) CD79b;
(16) FcRH2;
(17) HER2;
(18) NCA;
(19) MDP;
(20) IL20R-alpha;
(21) Brevican;
(22) EphB2R;
(23) ASLG659;
(24) PSCA;
(25) GEDA;
(26) BAFF-R;
(27) CD22;
(28) CD79a;
(29) CXCR5;
(30) HLA-DOB;
(31) P2X5;

(32) CD72;
(33) LY64;
(34) FcRH1;
(35) IRTA2;
(36) TENB2;
(37) PSMA-FOLH1;
(38) SST;
(38.1) SSTR2;
(38.2) SSTR5;
(38.3) SSTR1;
(38.4)SSTR3;
(38.5) SSTR4;
(39) ITGAV;
(40) ITGB6;
(41) CEACAM5;
(42) MET;
(43) MUC1;
(44) CA9;
(45) EGFRvIII;
(46) CD33;
(47) CD19;
(48) IL2RA;
(49) AXL;
(50) CD30-TNFRSF8;
(51) BCMA-TNFRSF17;
(52) CT Ags-CTA;
(53) CD174 (Lewis Y)-FUT3;
(54) CLEC14A;
(55) GRP78-HSPA5;
(56) CD70;
(57) Stem Cell specific antigens;
(58) ASG-5;
(59) ENPP3;
(60) PRR4;
(61) GCC-GUCY2C;
(62) Liv-1-SLC39A6;
(63) 5T4;
(64) CD56-NCMA1;
(65) CanAg;
(66) FOLR1;
(67) GPNMB;
(68) TIM-1-HAVCR1;
(69) RG-1/Prostate tumor target Mindin-Mindin/RG-1;
(70) B7-H4-VTCN1;
(71) PTK7;
(72) CD37;
(73) CD138-SDC1;
(74) CD74;
(75) Claudins-CLs;
(76) EGFR;
(77) Her3;
(78) RON-MST1R;
(79) EPHA2;
(80) CD20-MS4A1;
(81) Tenascin C-TNC;
(82) FAP;
(83) DKK-1;
(84) CD52;
(85) CS1-SLAMF7;
(86) Endoglin-ENG;
(87) Annexin A1-ANXA1;
(88) V-CAM (CD106)-VCAM1;
(89) ASCT2 (SLC1A5).

66. The conjugate of any one of statements 63 to 65 wherein the antibody or antibody fragment is a cysteine-engineered antibody.

67. The conjugate according to any one of statements 57 to 66 wherein p is an integer from 1 to 8.

68. The conjugate according to statement 67, wherein p is 1, 2, 3, or 4.

69. A composition comprising a mixture of conjugates according to any one of statements 57 to 68, wherein the average p in the mixture of conjugate compounds is about 1 to about 8.

70. The conjugate according to any one of statements 57 to 68, for use in therapy.

71. A pharmaceutical composition comprising the conjugate of any one of statements 57 to 68, and a pharmaceutically acceptable diluent, carrier or excipient.

72. The conjugate according to any one of statements 57 to 68 or the pharmaceutical composition according to statement 71, for use in the treatment of a proliferative disease in a subject.

73. The conjugate for use according to statement 72, wherein the disease treated is cancer.

74. Use of a conjugate according to any one of statements 57 to 68 or the pharmaceutical composition according to statement 71 in a method of medical treatment.

75. A method of medical treatment comprising administering to a patient the pharmaceutical composition of statement 71.

76. The method of statement 75 wherein the method of medical treatment is for treating cancer.

77. The method of statement 76, wherein the patient is administered a chemotherapeutic agent, in combination with the conjugate.

78. Use of a conjugate according to any one of statements 57 to 68 in a method of manufacture of a medicament for the treatment of a proliferative disease.

79. A method of treating a mammal having a proliferative disease, comprising administering an effective amount of a conjugate according to any one of statements 57 to 68 or the pharmaceutical composition according to statement 71.

The invention claimed is:

1. A compound of formula IV:

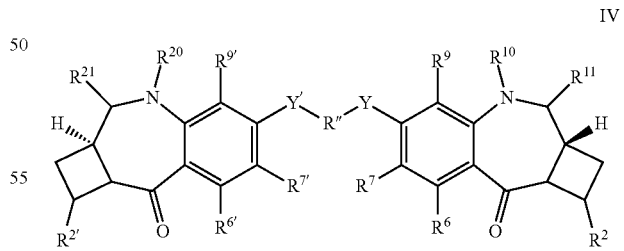

IV or a pharmaceutically acceptable salt thereof, wherein:

$R^2$ and $R^{2'}$ are H;

$R^6$ and $R^9$ are independently selected from H, R, OH, OR, SH, SR, $NH_2$, NHR, NRR', nitro, $Me_3Sn$ and halo;

where R and R' are independently selected from $C_{1-12}$ alkyl, $C_{3-20}$ heterocyclyl and $C_{6-10}$ carboaryl groups, and $C_{5-14}$ heteroaryl groups;

either
(a) $R^7$ is selected from H, R, OH, OR, SH, SR, $NH_2$, NHR, NRR', nitro, $Me_3Sn$ and halo;
$R^{7'}$ is selected from H, R, OH, OR, SH, SR, $NH_2$, NHR, NRR', nitro, $Me_3Sn$ and halo; or
(b) $R^7$ and $R^{7'}$ together form a group which is: (i) —O—$(CH_2)_n$—O—, where n is from 7 to 16; or
(ii) —O—$(CH_2CH_2O)_m$—, where m is 2 to 5;
R" is a $C_{3-12}$ alkylene group, which chain may be interrupted by one or more heteroatoms,
selected from O, S, $NR^{N2}$, where $R^{N2}$ is H or $C_{1-4}$ alkyl, and/or by aromatic rings;
selected from benzene or pyridine;
Y and Y' are selected from O, S, or NH;

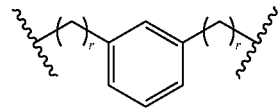

where r is 1 or 2; and/or
d) $R^{6'}$ is the same group as $R^6$, $R^{7'}$ is the same group as $R^7$, $R^{9'}$ is the same group as $R^9$ and Y' is the same group as Y.

3. A compound according to claim 1, wherein $R^9$ is H, $R^6$ is H, $R^7$ and $R^{7'}$ are independently a $C_{1-4}$ alkyloxy group.

4. A compound according to claim 1, which is of formulae IVa, IVb or IVc:

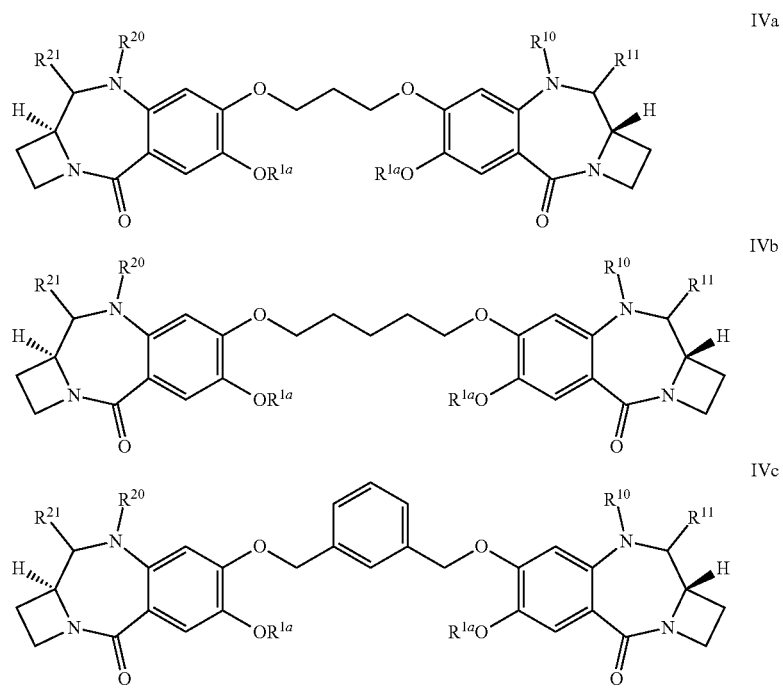

$R^{6'}$ and $R^{9'}$ are selected from the same groups as $R^6$, and $R^9$ respectively;
either
(i-a) $R^{10}$ and $R^{11}$ together form a double bond between the N and C atoms to which they are bound; or
(i-b) $R^{10}$ is H and $R^{11}$ is selected from OH and $OR^A$, where $R^A$ is $C_{1-4}$ alkyl; or
(i-c) $R^{10}$ and $R^{11}$ are both H;
either
(ii-a) $R^{20}$ and $R^{21}$ together form a double bond between the N and C atoms to which they are bound; or
(ii-b) $R^{20}$ is H and $R^{21}$ is selected from OH and ORB, where RB is $C_{1-4}$ alkyl; or
(ii-c) $R^{20}$ and $R^{21}$ are both H.

2. A compound according to claim 1, wherein:
a) both Y and Y' are O; and/or
b) R" is $C_{3-7}$ alkylene; or
c) R" is a group of formula:

where $R^{1a}$ is selected from methyl and benzyl.

5. A compound of formula I:

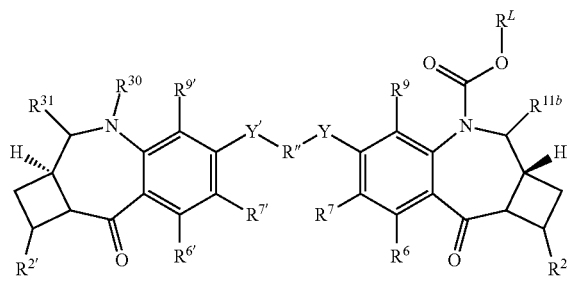

or a pharmaceutically acceptable salt thereof, wherein:

Y and Y' are selected from O, S, or NH;

R'' is a $C_{3-12}$ alkylene group, which chain may be interrupted by one or more heteroatoms selected from O, S, $NR^{N2}$, where $R^{N2}$ is H or $C_{1-4}$ alkyl, and/or by aromatic rings selected from benzene or pyridine;

$R^2$ and $R^{2'}$ are H;

$R^6$ and $R^9$ are independently selected from H, R, OH, OR, SH, SR, $NH_2$, NHR, NRR', nitro, $Me_3Sn$ and halo; where R and R' are independently selected from $C_{1-12}$ alkyl, $C_{3-20}$ heterocyclyl, $C_{6-10}$ carboaryl groups, and $C_{5-14}$ heteroaryl groups;

either (a) $R^7$ is selected from H, R, OH, OR, SH, SR, $NH_2$, NHR, NRR', nitro, $Me_3Sn$ and halo;

$R^{7'}$ is selected from H, R, OH, OR, SH, SR, $NH_2$, NHR, NRR', nitro, $Me_3Sn$ and halo; or (b) $R^7$ and $R^{7'}$ together form a group which is: (i) —O—$(CH_2)_n$—O—, where n is from 7 to 16; or
(ii) —O—$(CH_2CH_2O)_m$—, where m is 2 to 5;

$R^{6'}$ and $R^{9'}$ are selected from the same groups as $R^6$ and $R^9$ respectively;

$R^{11b}$ is selected from OH, $OR^A$, where $R^A$ is $C_{1-4}$ alkyl; and $R^L$ is a linker for connection to a cell binding agent, which is selected from:

(iiia):

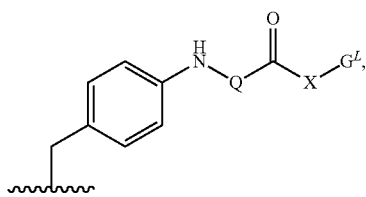

wherein

Q is:

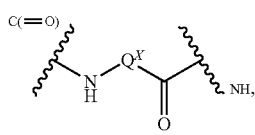

where $Q^X$ is such that Q is an amino-acid residue, a dipeptide residue or a tripeptide residue;

X is:

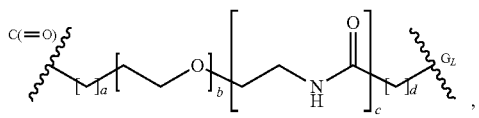

where a=0 to 5, b=0 to 16, c=0 or 1, d=0 to 5;

$G^L$ is a linker for connecting to a Ligand Unit; and (iiib):

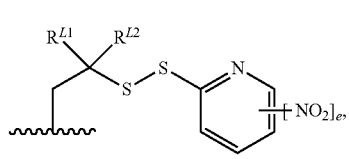

where $R^{L1}$ and $R^{L2}$ are independently selected from H and methyl, or together with the carbon atom to which they are bound form a cyclopropylene or cyclobutylene group;

and e is 0 or 1;

either:

(a) $R^{30}$ and $R^{31}$ together form a double bond between the N and C atoms to which they are bound; or (b) $R^{30}$ is H and $R^{31}$ is selected from OH and ORB, where RB is $C_{1-4}$ alkyl, (c) $R^{30}$ and $R^{31}$ are both H; or (d) $R^{31}$ is OH or ORB, where RB is $C_{1-4}$ alkyl and $R^{30}$ is selected from:

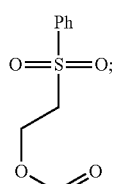

(i)

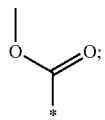

(ii)

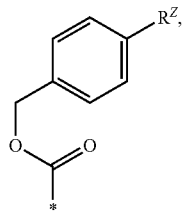

(iii)

where $R^Z$ is selected from:

(z-i)

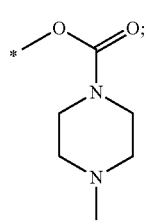

(z-ii) OC(=O) CH$_3$;
(z-iii) NO$_2$;
(z-iv) OMe;
(z-v) glucoronide;
(z-vi) NH—C(=O)—X$_1$—NHC(=O) X$_2$—NH—C(=O)—R$^{ZC}$, where —C(=O)—X$_1$—NH— and —C(=O)—X$_2$—NH— represent natural amino acid residues and R$^{ZC}$ is selected from Me, OMe, CH$_2$CH$_2$OMe, and (CH$_2$CH$_2$O)$_2$Me.

6. A compound according to claim 5, wherein R$^{30}$ and R$^{31}$ together form a double bond between the N and C atoms to which they are bound.

7. A compound according to claim 5, which is of formula Ia, Ib or Ic:

Ia

Ib

Ic where R$^{1a}$ is selected from methyl and benzyl.

8. A compound according to claim 5, wherein R$^L$ is of formula IIIa, and Q is a dipeptide residue selected from:
$^{CO}$-Phe-Lys-$^{NH}$,
$^{CO}$-Val-Ala-$^{NH}$,
$^{CO}$-Val-Lys-$^{NH}$,
$^{CO}$-Ala-Lys-$^{NH}$,
$^{CO}$-Val-Cit-$^{NH}$,
$^{CO}$-Phe-Cit-$^{NH}$,
$^{CO}$-Leu-Cit-$^{NH}$,
$^{CO}$-Ile-Cit-$^{NH}$,
$^{CO}$-Phe-Arg-$^{NH}$, and
$^{CO}$-Trp-Cit-$^{NH}$.

9. A compound according to claim 5, wherein R$^L$ is of formula IIIa and, a is 0, c is 1 and d is 2, and b is from 0 to 8.

10. A compound according to claim 9, wherein b is 0, 4 or 8.

11. A compound according to claim 5, wherein R$^L$ is of formula IIIa and G$^L$ is selected from:

(G$^{L1-1}$)

-continued (G$^{L1-2}$)

(G$^{L2}$)

-continued

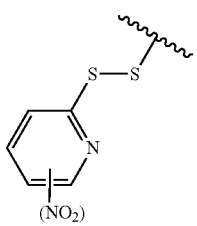 (G^{L3-1})

where the NO₂ group is optional

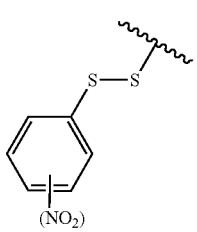 (G^{L3-2})

where the NO₂ group is optional

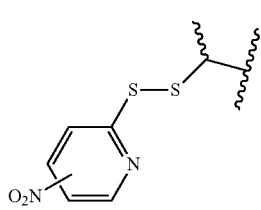 (G^{L3-3})

where the NO₂ group is optional

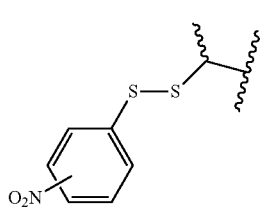 (G^{L3-4})

where the NO₂ group is optional

-continued

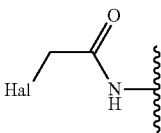 (G^{L4})

Where Hal = I, Br, Cl

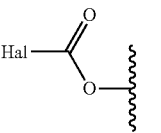 (G^{L5})

Where Hal = I, Br, Cl

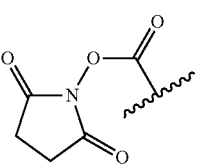 (G^{L6})

 (G^{L7})

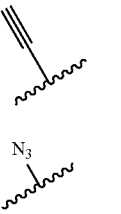 (G^{L8})

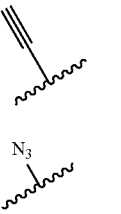 (G^{L9})

where Ar represents a phenylene group.

12. A compound according to claim 11, wherein $G^L$ is $G^{L1-1}$.

13. A compound according to claim 5, wherein the compound is of formula Id:

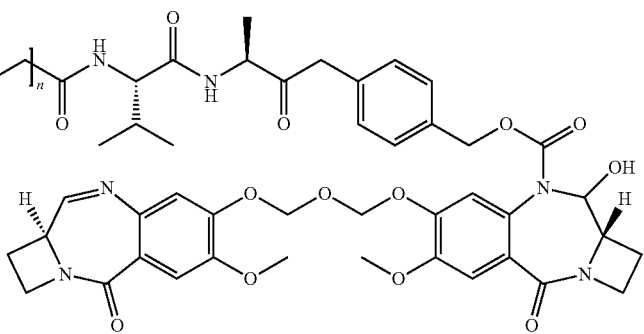 (Id)

where Q is selected from:
(a) —CH$_2$—;
(b) —C$_3$H$_6$—; and
(c)

[structure: meta-substituted phenyl with two wavy-line attachment points]

14. A conjugate of formula II:

$$L\text{-}(D^L)_p \quad \text{(II)}$$

wherein L is a Ligand unit (optionally a targeting agent, D$^L$ is a Drug Linker unit of formula I':

[structure I*: PBD dimer with substituents R$^{30}$, R$^{31}$, R$^{9'}$, R$^9$, R$^{11b}$, R$^{LL}$, Y', Y, R", R$^{7'}$, R$^7$, R$^{6'}$, R$^6$, R$^{2'}$, R$^2$]

wherein:
R$^2$ and R$^{2'}$ are H;
R$^6$ and R$^9$ are independently selected from H, R, OH, OR, SH, SR, NH$_2$, NHR, NRR', nitro, Me$_3$Sn and halo;
where R and R' are independently selected from C$_{1-12}$ alkyl, C$_{3-20}$ heterocyclyl, C$_{6-10}$ carboaryl groups, and C$_{5-14}$ heteroaryl groups;
either
(a) R$^7$ is selected from H, R, OH, OR, SH, SR, NH$_2$, NHR, NRR', nitro, Me$_3$Sn and halo;
R$^{7'}$ is selected from H, R, OH, OR, SH, SR, NH$_2$, NHR, NRR', nitro, Me$_3$Sn and halo; or
(b) R$^7$ and R$^{7'}$ together form a group which is: (i) —O—(CH$_2$)$_n$—O—, where n is from 7 to 16; or
(ii) —O—(CH$_2$CH$_2$O)$_m$—, where m is 2 to 5;
R" is a C$_{3-12}$ alkylene group, which chain may be interrupted by one or more heteroatoms;
selected from O, S, NR$^{N2}$, where R$^{N2}$ is H or C$_{1-4}$ alkyl, and/or by aromatic rings;
selected from benzene or pyridine;
Y and Y' are selected from O, S, or NH;
R$^{6'}$ and R$^{9'}$ are selected from the same groups as R$^6$, and R$^9$ respectively;
R$^{11b}$ is selected from OH, OR$^A$, where R$^A$ is C$_{1-4}$ alkyl;
either:
(a) R$^{30}$ and R$^{31}$ together form a double bond between the N and C atoms to which they are bound; or
(b) R$^{30}$ is H and R$^{31}$ is selected from OH and ORB, where RB is C$_{1-4}$ alkyl; or
(c) R$^{30}$ and R$^{31}$ are both H; or
(d) R$^{31}$ is OH or ORB, where RB is C$_{1-4}$ alkyl and R$^{30}$ is selected from:

(i) [structure: Ph-S(=O)$_2$-CH$_2$CH$_2$-O-C(=O)-O-*]

(ii) [structure: Me-O-C(=O)-O-*]

(iii) [structure: para-R$^Z$-substituted benzyl-O-C(=O)-O-*]

where R$^Z$ is selected from:

(z-i) [structure: *-O-C(=O)-N(piperazine)-N-CH$_3$]

(z-ii) OC(=O) CH$_3$;
(z-iii) NO$_2$;
(z-iv) OMe;
(z-v) glucoronide;
(z-vi) NH—C(=O)—X$_1$—NHC(=O) X$_2$—NH—C(=O)—R$^{ZC}$, where —C(=O)—X$_1$—NH— and —C(=O)—X$_2$—NH— represent natural amino acid residues and R$^{ZC}$ is selected from Me, OMe, CH$_2$CH$_2$OMe, and (CH$_2$CH$_2$O)$_2$Me;

R$^{LL}$ is a linker for connection to a cell binding agent, which is selected from:

(iiia'):

[structure IIIa': para-substituted benzyl-NH-Q-C(=O)-O-X-G$^{LL}$, with wavy bond at benzyl]

where Q is:

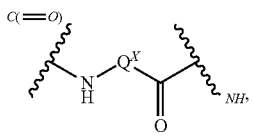

where $Q^X$ is such that Q is an amino-acid residue, a dipeptide residue or a tripeptide residue:

X is:

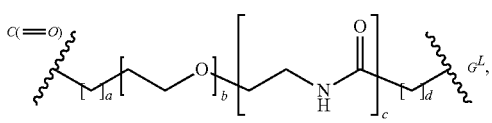

where a=0 to 5, b=0 to 16, c=0 or 1, d=0 to 5; and $G^{LL}$ is a linker connected to a Ligand Unit; and (iiib'):

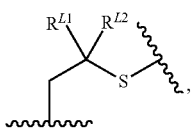
IIIb' where $R^{L1}$ and $R^{L2}$ are independently selected from H and methyl, or together with the carbon atom to which they are bound form a cyclopropylene or cyclobutylene group;

wherein p is an integer of from 1 to 20.

15. A conjugate according to claim 14, wherein $G^{LL}$ is selected from:

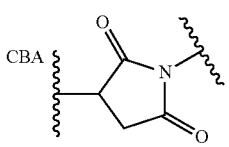
($G^{LL1-1}$)

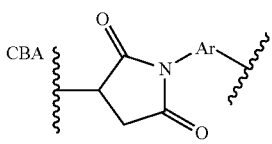
($G^{LL1-2}$)

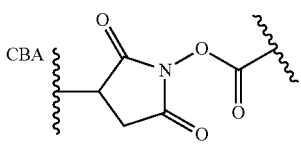
($G^{LL2}$)

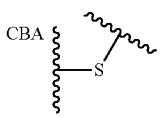
($G^{LL3-1}$)

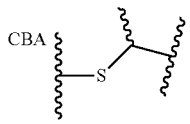
($G^{LL3-2}$)

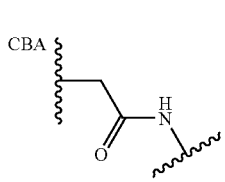
($G^{LL4}$)

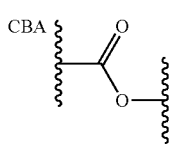
($G^{LL5}$)

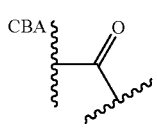
($G^{LL6}$)

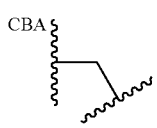
($G^{LL7}$)

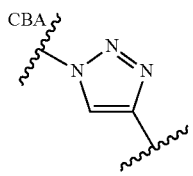
($G^{LL8-1}$)

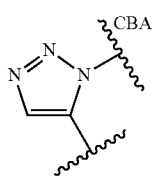
($G^{LL8-2}$)

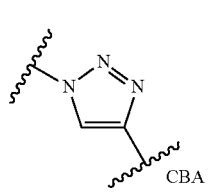
($G^{LL9-1}$)

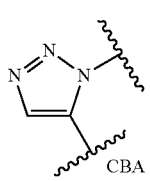
($G^{LL9-2}$)

where Ar represents a phenylene group.

16. A conjugate according to claim 14, wherein DL is of formula (Id'):

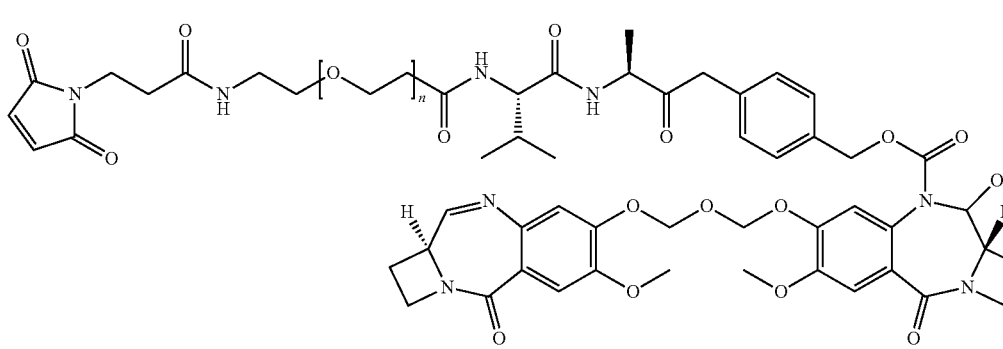

where Q is selected from:
(a) —$CH_2$—;
(b) —$C_3H_6$—; and
(c)

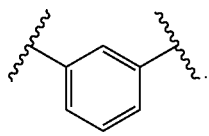 [SMILES: *c1cccc(*)c1]

17. A composition comprising a mixture of conjugates according to claim 14, wherein the average p in the mixture of conjugates is about 1 to about 8.

18. A pharmaceutical composition comprising the conjugate of claim 14, and a pharmaceutically acceptable diluent, carrier or excipient.

19. A method of treating cancer in a subject comprising administering to a patient the pharmaceutical composition of claim 18, wherein the cancer is gastric carcinoma or metastatic adenocarcinoma of the breast.

\* \* \* \* \*